US008062856B2

(12) United States Patent
Ghosh et al.

(10) Patent No.: US 8,062,856 B2
(45) Date of Patent: *Nov. 22, 2011

(54) SYSTEM FOR CELL-BASED SCREENING

(75) Inventors: Richik Ghosh, Cranberry Township, PA (US); Robbin DeBiasio, Pittsburgh, PA (US); Prem Janardhan, Dubai (AE)

(73) Assignee: Cellomics, Inc., Pittsburgh, PA (US)

( * ) Notice: Subject to any disclaimer, the term of this patent is extended or adjusted under 35 U.S.C. 154(b) by 970 days.

This patent is subject to a terminal disclaimer.

(21) Appl. No.: 11/229,382

(22) Filed: Sep. 16, 2005

(65) Prior Publication Data

US 2006/0014137 A1    Jan. 19, 2006

Related U.S. Application Data

(63) Continuation of application No. 09/716,732, filed on Nov. 20, 2000, now Pat. No. 6,986,993, which is a continuation of application No. 09/632,552, filed on Aug. 4, 2000, now abandoned.

(60) Provisional application No. 60/147,443, filed on Aug. 5, 1999, provisional application No. 60/176,589, filed on Jan. 18, 2000, provisional application No. 60/205,696, filed on May 19, 2000.

(51) Int. Cl.
*G01N 33/53* (2006.01)
*G01N 33/543* (2006.01)

(52) U.S. Cl. ........ 435/7.21; 435/7.1; 436/501; 436/506; 436/518; 422/50; 422/61; 530/300; 530/350; 424/9.1

(58) Field of Classification Search .................. 435/7.11, 435/258.7; 436/501, 43, 172
See application file for complete search history.

(56) References Cited

U.S. PATENT DOCUMENTS

| | | | |
|---|---|---|---|
| 4,762,701 A | 8/1988 | Horan et al. | |
| 4,783,401 A | 11/1988 | Horan et al. | |
| 4,859,584 A | 8/1989 | Horan et al. | |
| 5,401,629 A | 3/1995 | Harpold et al. | |
| 5,436,128 A | 7/1995 | Harpold et al. | |
| 5,491,084 A | 2/1996 | Chalfie et al. | |
| 5,599,681 A | 2/1997 | Epstein et al. | |
| 5,989,835 A | 11/1999 | Dunlay et al. | |
| 6,103,479 A | 8/2000 | Taylor | |
| 6,416,959 B1 | 7/2002 | Giuliano | |
| 6,573,039 B1 | 6/2003 | Dunlay | |
| 6,620,591 B1 | 9/2003 | Dunlay | |
| 6,671,624 B1 | 12/2003 | Dunlay | |
| 6,716,588 B2 | 4/2004 | Sammak | |
| 6,727,071 B1 | 4/2004 | Dunlay | |
| 6,759,206 B1 | 7/2004 | Rubin | |
| 6,875,578 B2 | 4/2005 | Giuliano | |
| 6,902,883 B2 | 6/2005 | Dunlay | |
| 2004/0009539 A1 | 1/2004 | Dunlay | |
| 2004/0063162 A1 | 4/2004 | Ghosh | |
| 2004/0101912 A1 | 5/2004 | Rubin | |

FOREIGN PATENT DOCUMENTS

| | | |
|---|---|---|
| WO | WO 95/21191 | 8/1995 |
| WO | WO 96/09598 | 3/1996 |
| WO | WO 96/23898 | 8/1996 |
| WO | WO 96/27675 | 9/1996 |
| WO | WO 97/43732 | 11/1997 |
| WO | WO 98/38490 | 9/1998 |
| WO | WO 00/03246 | 3/2000 |
| WO | WO 00/17643 | 3/2000 |
| WO | WO 00/26408 | 5/2000 |
| WO | WO 00/50872 | 8/2000 |
| WO | WO 00/70342 | 11/2000 |
| WO | WO 00/79241 | 12/2000 |
| WO | WO 01/11340 | 2/2001 |
| WO | WO 01/11341 | 2/2001 |
| WO | WO 01/35072 | 5/2001 |
| WO | WO 01/42786 | 6/2001 |

OTHER PUBLICATIONS

Baldwin, (1996), Annu Rev Immunol, 14:649-683.
Barak et al., (1997), J. Biol. Chem., 272(44):27497-27500.
Barber et al., (1996), Neuroscience Letters, 207:17-20.
Beggs (1997), J. of Biomolec. Screening, 2(2):71-78.
Bislang et al., (1999), J. Neuroscience Methods, 92:75-85.
Bright et al., (1987), J. Cell Biol., 104:1019-1033.
Bright et al., (1989), J. Cell. Physiol., 141:410-419.
Bright et al., (1989), Methods in Cell Biology, 30:157-192.
Bright et al., (1996), Cytometry, 24:226-233.
Brugmans et al., (1983), Cytometry, 3:(4), pp. 262-268.
Cellomics, Inc., (2000 ) "Neurite Outgrowth," http://www.cellomics.com/html/products/neurite_outgrowth.htm, 2000, pp. 1-3.
Chalfie et al., (1994), Science, 263:802-805.
Chow et al., (1997) Science, 278:1638-1641.
Cohen, (1997), Biochemical J., 326:1-16.
Coso et al., (1995) Cell, 81:1137-1146.
Cubitt et al., (1995), Trends in Biochemical Science, 20:448-455.
Daaka et al., (1998), J. Biol. Chem., 273(2):685-688.
Davis et al., (1995), Dev. Biology, 170:726-729.
DeBiasio et al., (1996), Mol. Biol. Cell, 7:1259-1282.
Denk et al., (1990), Science, 248:73-76.
Deprez et al., (1997), J. Biol. Chem., 272(28):17269-17275.
Ding et al., (1998), J. Biol. Chem., 273(44):28897-28905.
Ellenberg et al., (1997), J. Cell Biol., 138(6):1193-1206.
Farkas et al., (1993), Annu. Rev. Physiol., 55:785-817.
Federov et al., 11994), J. Mol. Biol., 241:480-482.
Firestone et al., (1991), Cytometry, 12:195-206.
Gerrittsen et al., (1997), J. of Fluorescence, 7(1)11-15.
Giuliano et al., (1987), Anal. Biochem., 167:362-371.
Giuliano et al., (1990), Optical Microscopy for Biology, pp. 543-557.
Giuliano et al., (1995), Annu. Rev. of Biophysics and Biomolecular Structure, 24:405-434.
Giuliano et al., (1995), Curr. Op. Cell Biol., 7:4-12.
Giuliano et al., 11995), Methods in Neuroscience, 27:1-16.

(Continued)

Primary Examiner — Lisa V Cook
(74) Attorney, Agent, or Firm — McDonnell Boehnen Hulbert & Berghoff LLP

(57) ABSTRACT

The present invention provides systems, methods, screens, reagents and kits for optical system analysis of cells to rapidly determine the distribution, environment, or activity of fluorescently labeled reporter molecules in cells for the purpose of screening large numbers of compounds for those that specifically affect neurite outgrowth.

16 Claims, 31 Drawing Sheets

OTHER PUBLICATIONS

Giuliano, (1996), Cell Motil. Cytoskel., 35:237-253.
Go et al., (1997), Analytical Biochemistry, 247:210-215.
Goldman et al., (1995), Experimental Cell Research, 221:311-319.
Gonzales et al., (1987), Digital Image Processing, pp. 391-448.
Gough et al., (1993), J. Cell Biol., 121(5):1095-1107.
Graham et al., (1973), Virology, 52:456-467.
Gratton et al., (1994), Proc. of the Microscopical Society of America, pp. 154-155.
Groen et al., (1985), Cytometry, 6:81-91.
Hahn et al., (1992), Nature, 359:736-738.
Hahn et al., (1993), Fluorescent and Luminescent Probes for Biological Activity, pp. 349-359.
Hall et al., (1997), Proc. Nat. Acad. Sci., 94:4733-4738.
Hall et al., (1999), J Biol Chem., 274(1):376-383.
Han et al., (1995), Biochim. Biophys. Acta, 1265:224-227.
Harms et al., (1984), Cytometry, 5:236-243.
Harootunian et al., (1993), Mol. Biol. of the Cell, 4:993-1002.
Heim et al., (1996), Curr. Biol., 6:178-182.
Hoey et al., (1998), Curr Opin Genet Dev., 8:582-587.
Htun et al., (1996), Proc. Natl. Acad. Sci., 93:4845-4850.
Hu et al., (1995), FEBS Letters, 369:331-334.
Jaaro et al., (1997), Proc. Natl. Acad. Sci. U.S.A., 94:3742-3747.
Johnson et al., (1998), Cell, 85:149-158.
Kaech et al., (1996), Neuron., 17:1189-1199.
Kaether et al., (1995), FEBS Letters, 369:267-271.
Kessler et al., (1991), Spectrochimica Acta, 47A(2):187-192.
Keβler et al., (1996), FEBS Letters, 395:225-227.
Kislauskis et al., (1994), J. Cell Biol., 127(2):441-451.
Kittler et al., (1985), Computer Vision, Graphics, and Image Processing, 30:125-147.
Kolega et al., (1993), BioImaging, 1:136-150.
Kuo et al., (1999), Annu Rev Immunol., 17:149-187.
Lakowicz et al., (1992), Anal. Biochem., 202:316-330.
Lambrechts et al., (1995), Eur. J. Biochem., 230:281-286.
Lee et al., (1996), Biochemistry, 35:6010-6019.
Lee et al., (1997), Biochemistry, 36:2701-2708.
Liang et al., (1997), J. of Molec. Biol., 274:291-302.
Liu et al., (1998), Curr Opin Immunol., 10:271-278.
Martinez-Zaguilan et al., (1996), Am. J. Physiol., 270:C1438-C1446.
Masuda et al., (1998), Cell Signal., 10(9):599-611.
McCaffrey et al., (1996), J. Biomolec. Screening, 1(4):187-190.
McCann et al., (1997), Proc. Natl. Acad. Sci., 94:5679-5684.
McNeil, (1989), Methods in Cell Biology, 29:153-173.
Morise et al., (1974), Biochemistry, 13(12):2656-2662.
Olson et al., (1995), J. Cell Biol., 130(3):639-650.
Palm et al., (1997), Nat. Struct. Biol., 4(5):361-365.
Paolillo et al., (1999), J Biol Chem., 274(10):6546-6552.
Presley et al., (1997), Nature, 389:81-85.
Proffitt et al., (1996), Cytometry, 24:204-213.
Ramakers et al., (1998), Developmental Brain Research, 108:205-216.
Rao et al., (1997), Annu Rev Immunol., 15:707-747.
Ridler et al., (1978), IEEE Trans. Systems, Man, and Cybernetics, 8:630-632.
Rizzuto et al., (1995), Curr. Biology, 5(6):635-642.
Russ, (1992), The Image Processing Handbook, CRC Press Inc., 225-275.
Schaeffer et al., (1999), Mol Cell Biol., 19(4):2435-2444.
Self et al., (1995), Methods in Enzymology, 256:3-10.
Shimoura et al., (1988), J. of Biochemistry, 251:405-410.
Southwick et al., (1990), Cytometry, 11:418-430.
Strehlow et al., (1998), J. Biol. Chem., 273(43):28049-28056.
Sutoh, (1982), Biochemistry, 21:3654-3661.
Tanaka et al., (1995), Methods in Enzymology, 256:41-49.
Taylor et al., (1992), American Scientist, 80:322-335.
Taylor et al., (1994), J. Biol. Chem., 269(1):308-318.
Taylor et al., (1996), Intl. Soc. for Optical Engineering, 2678: 15-27.
Thomas et al., (1979) Biochemistry, 18(11):2210-2218.
Tibbles et al. (1999), Cell Mol Life Sci., 55:1230-1254.
Tsien, (1989), Methods in Cell Biology, 30:127-156.
Tyagi et al., (1996), Nat. Biotechnol., 14:303-308.
Waggoner et al., (1996), Hum. Pathol., 27:494-502.
Walker et al., (1993), J. Biol. Chem. 268:19552-19558.
Ward et al., (1980), Photochem. Photobiol., 31:611-615.
Welch et al., (1995), In Vitro Cell. Dev. Biol.-Animal 31:610-616.
Zhao et al., (1999), J. Biol Chem., 274(13):8355-8358.

Figure 2
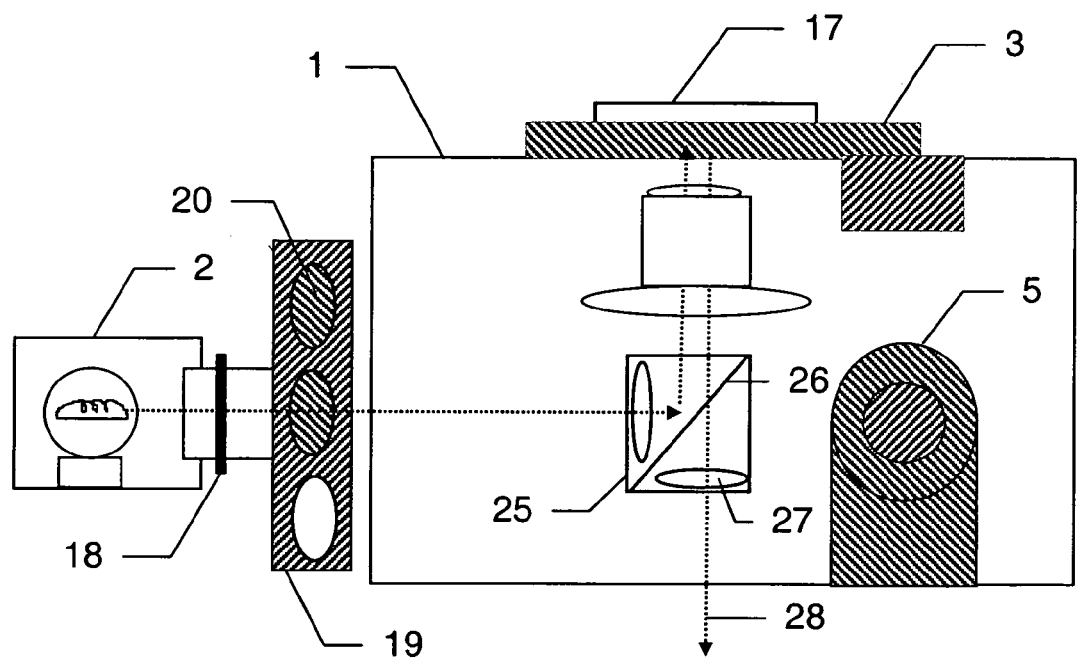
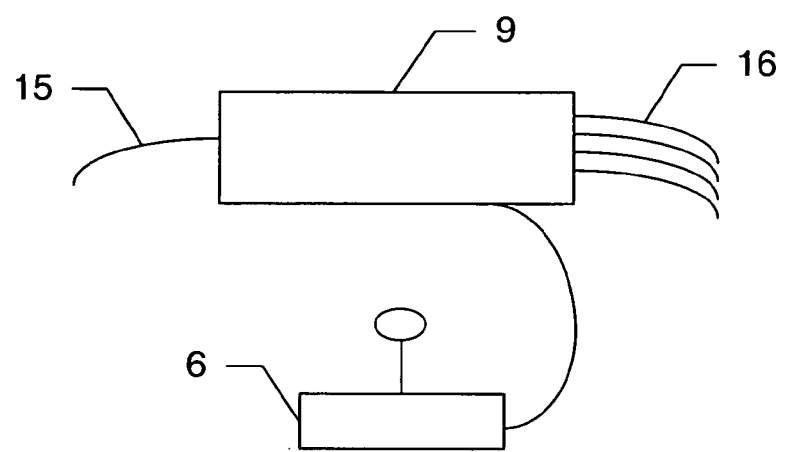

SYSTEM FOR CELL-BASED SCREENING

CROSS REFERENCE

This application is a continuation of U.S. patent application Ser. No. 09/716,732 filed Nov. 20, 2000, now U.S. Pat. No. 6,986,993, which is a continuation of U.S. patent application Ser. No. 09/632,552 filed Aug. 4, 2000, now abandoned, which claims priority from U.S. Provisional Patent Application Ser. Nos. 60/147,443 filed Aug. 5, 1999; 60/176,589 filed Jan. 18, 2000; and 60/205,696 filed May 19, 2000; all references incorporated by reference herein in their entirety.

FIELD OF THE INVENTION

This invention is in the field of fluorescence-based cell and molecular biochemical assays for drug discovery.

BACKGROUND OF THE INVENTION

Drug discovery, as currently practiced in the art, is a long, multiple step process involving identification of specific disease targets, development of an assay based on a specific target, validation of the assay, optimization and automation of the assay to produce a screen, high throughput screening of compound libraries using the assay to identify "hits", hit validation and hit compound optimization. The output of this process is a lead compound that goes into pre-clinical and, if validated, eventually into clinical trials. In this process, the screening phase is distinct from the assay development phases, and involves testing compound efficacy in living biological systems.

Historically, drug discovery is a slow and costly process, spanning numerous years and consuming hundreds of millions of dollars per drug created. Developments in the areas of genomics and high throughput screening have resulted in increased capacity and efficiency in the areas of target identification and volume of compounds screened. Significant advances in automated DNA sequencing, PCR application, positional cloning, hybridization arrays, and bioinformatics have greatly increased the number of genes (and gene fragments) encoding potential drug screening targets. However, the basic scheme for drug screening remains the same.

Validation of genomic targets as points for therapeutic intervention using the existing methods and protocols has become a bottleneck in the drug discovery process due to the slow, manual methods employed, such as in vivo functional models, functional analysis of recombinant proteins, and stable cell line expression of candidate genes. Primary DNA sequence data acquired through automated sequencing does not permit identification of gene function, but can provide information about common "motifs" and specific gene homology when compared to known sequence databases. Genomic methods such as subtraction hybridization and RADE (rapid amplification of differential expression) can be used to identify genes that are up or down regulated in a disease state model. However, identification and validation still proceed down the same pathway. Some proteomic methods use protein identification (global expression arrays, 2D electrophoresis, combinatorial libraries) in combination with reverse genetics to identify candidate genes of interest. Such putative "disease associated sequences" or DAS isolated as intact cDNA are a great advantage to these methods, but they are identified by the hundreds without providing any information regarding type, activity, and distribution of the encoded protein. Choosing a subset of DAS as drug screening targets is "random", and thus extremely inefficient, without functional data to provide a mechanistic link with disease. It is necessary, therefore, to provide new technologies to rapidly screen DAS to establish biological function, thereby improving target validation and candidate optimization in drug discovery.

There are three major avenues for improving early drug discovery productivity. First, there is a need for tools that provide increased information handling capability. Bioinformatics has blossomed with the rapid development of DNA sequencing systems and the evolution of the genomics database. Genomics is beginning to play a critical role in the identification of potential new targets. Proteomics has become indispensable in relating structure and function of protein targets in order to predict drug interactions. However, the next level of biological complexity is the cell. Therefore, there is a need to acquire, manage and search multidimensional information from cells. Secondly, there is a need for higher throughput tools. Automation is a key to improving productivity as has already been demonstrated in DNA sequencing and high throughput primary screening. The instant invention provides for automated systems that extract multiple parameter information from cells that meet the need for higher throughput tools. The instant invention also provides for miniaturizing the methods, thereby allowing increased throughput, while decreasing the volumes of reagents and test compounds required in each assay.

Radioactivity has been the dominant read-out in early drug discovery assays. However, the need for more information, higher throughput and miniaturization has caused a shift towards using fluorescence detection. Fluorescence-based reagents can yield more powerful, multiple parameter assays that are higher in throughput and information content and require lower volumes of reagents and test compounds. Fluorescence is also safer and less expensive than radioactivity-based methods.

Screening of cells treated with dyes and fluorescent reagents is well known in the art. There is a considerable body of literature related to genetic engineering of cells to produce fluorescent proteins, such as modified green fluorescent protein (GFP), as a reporter molecule. Some properties of wild-type GFP are disclosed by Morise et al. (*Biochemistry* 13 (1974), p. 2656-2662), and Ward et al. (*Photochem. Photobiol.* 31 (1980), p. 611-615). The GFP of the jellyfish *Aequorea victoria* has an excitation maximum at 395 nm and an emission maximum at 510 nm, and does not require an exogenous factor for fluorescence activity. Uses for GFP disclosed in the literature are widespread and include the study of gene expression and protein localization (Chalfie et al., *Science* 263 (1994), p. 12501-12504)), as a tool for visualizing subcellular organelles (Rizzuto et al., *Curr. Biology* 5 (1995), p. 635-642)), visualization of protein transport along the secretory pathway (Kaether and Gerdes, *FEBS Letters* 369 (1995), p. 267-271)), expression in plant cells (Hu and Cheng, *FEBS Letters* 369 (1995), p. 331-334)) and Drosophila embryos (Davis et al., *Dev. Biology* 170 (1995), p. 726-729)), and as a reporter molecule fused to another protein of interest (U.S. Pat. No. 5,491,084). Similarly, WO96/23898 relates to methods of detecting biologically active substances affecting intracellular processes by utilizing a GFP construct having a protein kinase activation site. This patent, and all other patents referenced in this application are incorporated by reference in their entirety Numerous references are related to GFP proteins in biological systems. For example, WO 96/09598 describes a system for isolating cells of interest utilizing the expression of a GFP like protein. WO 96/27675 describes the expression of GFP in plants. WO 95/21191 describes modified GFP protein expressed in transformed organisms to detect mutagenesis. U.S. Pat. Nos. 5,401,629 and 5,436,128 describe assays and compositions for detecting and evaluating the intracellular transduction of an extracellular signal using recombinant cells that express cell surface receptors and contain reporter gene constructs that include transcriptional regulatory elements that are responsive to the activity of cell surface receptors.

Performing a screen on many thousands of compounds requires parallel handling and processing of many compounds and assay component reagents. Standard high throughput screens ("HTS") use mixtures of compounds and biological reagents along with some indicator compound loaded into arrays of wells in standard microtiter plates with 96 or 384 wells. The signal measured from each well, either fluorescence emission, optical density, or radioactivity, integrates the signal from all the material in the well giving an overall population average of all the molecules in the well.

Science Applications International Corporation (SAIC) 130 Fifth Avenue, Seattle, Wash. 98109) describes an imaging plate reader. This system uses a CCD camera to image the whole area of a 96 well plate. The image is analyzed to calculate the total fluorescence per well for all the material in the well.

Molecular Devices, Inc. (Sunnyvale, Calif.) describes a system (FLIPR) which uses low angle laser scanning illumination and a mask to selectively excite fluorescence within approximately 200 microns of the bottoms of the wells in standard 96 well plates in order to reduce background when imaging cell monolayers. This system uses a CCD camera to image the whole area of the plate bottom. Although this system measures signals originating from a cell monolayer at the bottom of the well, the signal measured is averaged over the area of the well and is therefore still considered a measurement of the average response of a population of cells. The image is analyzed to calculate the total fluorescence per well for cell-based assays. Fluid delivery devices have also been incorporated into cell based screening systems, such as the FLIPR system, in order to initiate a response, which is then observed as a whole well population average response using a macro-imaging system.

In contrast to high throughput screens, various high-content screens ("HCS") have been developed to address the need for more detailed information about the temporal-spatial dynamics of cell constituents and processes. High-content screens automate the extraction of multicolor fluorescence information derived from specific fluorescence-based reagents incorporated into cells (Giuliano and Taylor (1995), *Curr. Op. Cell Biol.* 7:4; Giuliano et al. (1995) *Ann. Rev. Biophys. Biomol. Struct.* 24:405). Cells are analyzed using an optical system that can measure spatial, as well as temporal dynamics. (Farkas et al. (1993) *Ann. Rev. Physiol.* 55:785; Giuliano et al. (1990) In *Optical Microscopy for Biology*. B. Herman and K. Jacobson (eds.), pp. 543-557. Wiley-Liss, New York; Hahn et al (1992) *Nature* 359:736; Waggoner et al. (1996) *Hum. Pathol.* 27:494). The concept is to treat each cell as a "well" that has spatial and temporal information on the activities of the labeled constituents.

The types of biochemical and molecular information now accessible through fluorescence-based reagents applied to cells include ion concentrations, membrane potential, specific translocations, enzyme activities, gene expression, as well as the presence, amounts and patterns of metabolites, proteins, lipids, carbohydrates, and nucleic acid sequences (DeBiasio et al., (1996) *Mol. Biol. Cell.* 7:1259; Giuliano et al., (1995) *Ann. Rev. Biophys. Biomol. Struct.* 24:405; Heim and Tsien, (1996) *Curr. Biol.* 6:178).

High-content screens can be performed on either fixed cells, using fluorescently labeled antibodies, biological ligands, and/or nucleic acid hybridization probes, or live cells using multicolor fluorescent indicators and "biosensors." The choice of fixed or live cell screens depends on the specific cell-based assay required.

Fixed cell assays are the simplest, since an array of initially living cells in a microtiter plate format can be treated with various compounds and doses being tested, then the cells can be fixed, labeled with specific reagents, and measured. No environmental control of the cells is required after fixation. Spatial information is acquired, but only at one time point. The availability of thousands of antibodies, ligands and nucleic acid hybridization probes that can be applied to cells makes this an attractive approach for many types of cell-based screens. The fixation and labeling steps can be automated, allowing efficient processing of assays.

Live cell assays are more sophisticated and powerful, since an array of living cells containing the desired reagents can be screened over time, as well as space. Environmental control of the cells (temperature, humidity, and carbon dioxide) is required during measurement, since the physiological health of the cells must be maintained for multiple fluorescence measurements over time. There is a growing list of fluorescent physiological indicators and "biosensors" that can report changes in biochemical and molecular activities within cells (Giuliano et al., (1995) *Ann. Rev. Biophys. Biomol. Struct.* 24:405; Hahn et al., (1993) In *Fluorescent and Luminescent Probes for Biological Activity*. W. T. Mason, (ed.), pp. 349-359, Academic Press, San Diego).

The availability and use of fluorescence-based reagents has helped to advance the development of both fixed and live cell high-content screens. Advances in instrumentation to automatically extract multicolor, high-content information has recently made it possible to develop HCS into an automated tool. An article by Taylor, et al. (*American Scientist* 80 (1992), p. 322-335) describes many of these methods and their applications. For example, Proffitt et. al. (*Cytometry* 24: 204-213 (1996)) describe a semi-automated fluorescence digital imaging system for quantifying relative cell numbers in situ in a variety of tissue culture plate formats, especially 96-well microtiter plates. The system consists of an epifluorescence inverted microscope with a motorized stage, video camera, image intensifier, and a microcomputer with a PC-Vision digitizer. Turbo Pascal software controls the stage and scans the plate taking multiple images per well. The software calculates total fluorescence per well, provides for daily calibration, and configures easily for a variety of tissue culture plate formats. Thresholding of digital images and reagents which fluoresce only when taken up by living cells are used to reduce background fluorescence without removing excess fluorescent reagent.

Scanning confocal microscope imaging (Go et al., (1997) *Analytical Biochemistry* 247:210-215; Goldman et al., (1995) *Experimental Cell Research* 221:311-319) and multiphoton microscope imaging (Denk et al., (1990) *Science* 248:73; Gratton et al., (1994) *Proc. of the Microscopical Society of America*, pp. 154-155) are also well established methods for acquiring high resolution images of microscopic samples. The principle advantage of these optical systems is the very shallow depth of focus, which allows features of limited axial extent to be resolved against the background. For example, it is possible to resolve internal cytoplasmic features of adherent cells from the features on the cell surface. Because scanning multiphoton imaging requires very short duration pulsed laser systems to achieve the high photon flux required, fluorescence lifetimes can also be measured in these systems (Lakowicz et al., (1992) *Anal. Biochem.* 202:316-330; Gerrittsen et al. (1997), *J. of Fluorescence* 7:11-15)), providing additional capability for different detection modes. Small, reliable and relatively inexpensive laser systems, such as laser diode pumped lasers, are now available to allow multiphoton confocal microscopy to be applied in a fairly routine fashion.

A combination of the biological heterogeneity of cells in populations (Bright, et al., (1989). *J. Cell. Physiol.* 141:410; Giuliano, (1996) *Cell Motil. Cytoskel.* 35:237)) as well as the high spatial and temporal frequency of chemical and molecular information present within cells, makes it impossible to extract high-content information from populations of cells using existing whole microtiter plate readers. No existing high-content screening platform has been designed for multicolor, fluorescence-based screens using cells that are analyzed individually. Similarly, no method is currently available that combines automated fluid delivery to arrays of cells for the purpose of systematically screening compounds for the ability to induce a cellular response that is identified by HCS analysis, especially from cells grown in microtiter plates. Furthermore, no method exists in the art combining high throughput well-by-well measurements to identify "hits" in one assay followed by a second high content cell-by-cell measurement on the same plate of only those wells identified as hits.

The instant invention provides systems, methods, and screens that combine high throughput screening (HTS) and high content screening (HCS) that significantly improve target validation and candidate optimization by combining many cell screening formats with fluorescence-based molecular reagents and computer-based feature extraction, data analysis, and automation, resulting in increased quantity and speed of data collection, shortened cycle times, and, ultimately, faster evaluation of promising drug candidates. The instant invention also provides for miniaturizing the methods, thereby allowing increased throughput, while decreasing the volumes of reagents and test compounds required in each assay.

SUMMARY OF THE INVENTION

In one aspect, the present invention relates to a method for analyzing cells comprising
 providing cells containing fluorescent reporter molecules in an array of locations,
 treating the cells in the array of locations with one or more reagents,
 imaging numerous cells in each location with fluorescence optics,
 converting the optical information into digital data,
 utilizing the digital data to determine the distribution, environment or activity of the fluorescently labeled reporter molecules in the cells and the distribution of the cells, and
 interpreting that information in terms of a positive, negative or null effect of the compound being tested on the biological function In this embodiment, the method rapidly determines the distribution, environment, or activity of fluorescently labeled reporter molecules in cells for the purpose of screening large numbers of compounds for those that specifically affect particular biological functions. The array of locations may be a microtiter plate or a microchip which is a microplate having cells in an array of locations. In a preferred embodiment, the method includes computerized means for acquiring, processing, displaying and storing the data received. In a preferred embodiment, the method further comprises automated fluid delivery to the arrays of cells. In another preferred embodiment, the information obtained from high throughput measurements on the same plate are used to selectively perform high content screening on only a subset of the cell locations on the plate.

In another aspect of the present invention, a cell screening system is provided that comprises:
 a high magnification fluorescence optical system having a microscope objective,
 an XY stage adapted for holding a plate containing an array of cells and having a means for moving the plate for proper alignment and focusing on the cell arrays;
 a digital camera;
 a light source having optical means for directing excitation light to cell arrays and a means for directing fluorescent light emitted from the cells to the digital camera; and
 a computer means for receiving and processing digital data from the digital camera wherein the computer means includes a digital frame grabber for receiving the images from the camera, a display for user interaction and display of assay results, digital storage media for data storage and archiving, and a means for control, acquisition, processing and display of results.

In a preferred embodiment, the cell screening system further comprises a computer screen operatively associated with the computer for displaying data. In another preferred embodiment, the computer means for receiving and processing digital data from the digital camera stores the data in a bioinformatics data base. In a further preferred embodiment, the cell screening system further comprises a reader that measures a signal from many or all the wells in parallel. In another preferred embodiment, the cell screening system further comprises a mechanical-optical means for changing the magnification of the system, to allow changing modes between high throughput and high content screening. In another preferred embodiment, the cell screening system further comprises a chamber and control system to maintain the temperature, $CO_2$ concentration and humidity surrounding the plate at levels required to keep cells alive. In a further preferred embodiment, the cell screening system utilizes a confocal scanning illumination and detection system.

In another aspect of the present invention, a machine readable storage medium comprising a program containing a set of instructions for causing a cell screening system to execute procedures for defining the distribution and activity of specific cellular constituents and processes is provided. In a preferred embodiment, the cell screening system comprises a high magnification fluorescence optical system with a stage adapted for holding cells and a means for moving the stage, a digital camera, a light source for receiving and processing the digital data from the digital camera, and a computer means for receiving and processing the digital data from the digital camera. Preferred embodiments of the machine readable storage medium comprise programs consisting of a set of instructions for causing a cell screening system to execute the procedures set forth in FIG. 9, 11, 12, 13, 14 or 15. Another preferred embodiment comprises a program consisting of a set of instructions for causing a cell screening system to execute procedures for detecting the distribution and activity of specific cellular constituents and processes. In most preferred embodiments, the cellular processes include, but are not limited to, nuclear translocation of a protein, cellular hypertrophy, apoptosis, and protease-induced translocation of a protein.

In another preferred embodiment, a variety of automated cell screening methods are provided, including screens to analyze and to identify compounds that affect transcription factor activity, protein kinase activity, cell morphology, microtubule structure, apoptosis, receptor internalization, protease-induced translocation of a protein, and neurite outgrowth.

BRIEF DESCRIPTION OF THE DRAWINGS

FIG. 2 shows a schematic of the microscope subassembly.

DETAILED DESCRIPTION OF THE INVENTION

Figure 1:
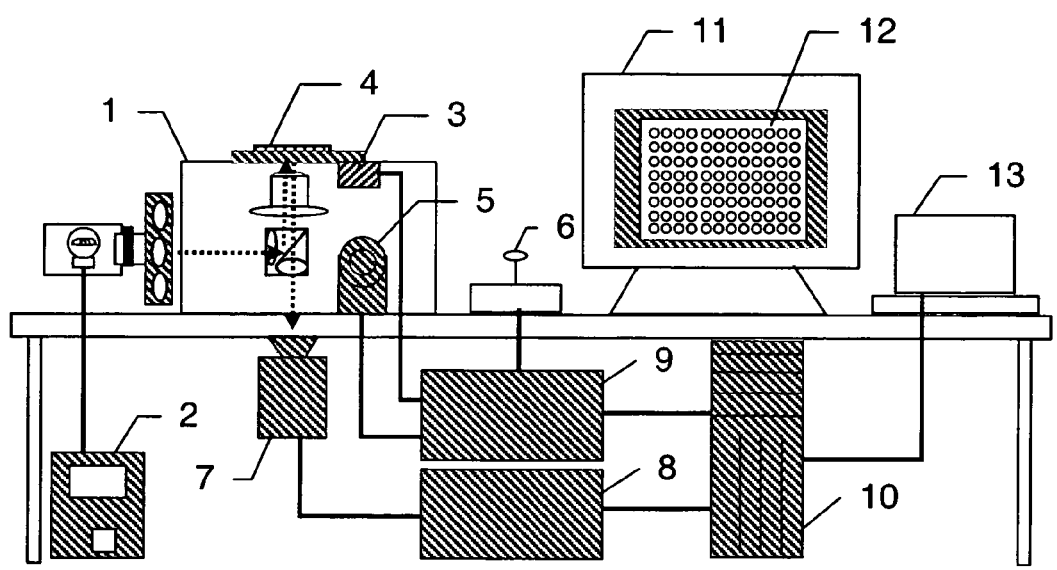
FIG. 1 shows a diagram of the components of the cell-based scanning system.

All cited patents, patent applications and other references are hereby incorporated by reference in their entirety.

As used herein, the following terms have the specified meaning:

Markers of cellular domains. Luminescent probes that have high affinity for specific cellular constituents including specific organelles or molecules. These probes can either be small luminescent molecules or fluorescently tagged macromolecules used as "labeling reagents", "environmental indicators", or "biosensors."

Labeling reagents. Labeling reagents include, but are not limited to, luminescently labeled macromolecules including fluorescent protein analogs and biosensors, luminescent macromolecular chimeras including those formed with the green fluorescent protein and mutants thereof, luminescently labeled primary or secondary antibodies that react with cellular antigens involved in a physiological response, luminescent stains, dyes, and other small molecules.

Markers of cellular translocations. Luminescently tagged macromolecules or organelles that move from one cell domain to another during some cellular process or physiological response. Translocation markers can either simply report location relative to the markers of cellular domains or they can also be "biosensors" that report some biochemical or molecular activity as well.

Biosensors. Macromolecules consisting of a biological functional domain and a luminescent probe or probes that report the environmental changes that occur either internally or on their surface. A class of luminescently labeled macromolecules designed to sense and report these changes have been termed "fluorescent-protein biosensors". The protein component of the biosensor provides a highly evolved molecular recognition moiety. A fluorescent molecule attached to the protein component in the proximity of an active site transduces environmental changes into fluorescence signals that are detected using a system with an appropriate temporal and spatial resolution such as the cell scanning system of the present invention. Because the modulation of native protein activity within the living cell is reversible, and because fluorescent-protein biosensors can be designed to sense reversible changes in protein activity, these biosensors are essentially reusable.

Disease associated sequences ("DAS"). This term refers to nucleic acid sequences identified by standard techniques, such as primary DNA sequence data, genomic methods such as subtraction hybridization and RADE, and proteomic methods in combination with reverse genetics, as being of drug candidate compounds. The term does not mean that the sequence is only associated with a disease state.

High content screening (HCS) can be used to measure the effects of drugs on complex molecular events such as signal transduction pathways, as well as cell functions including, but not limited to, apoptosis, cell division, cell adhesion, locomotion, exocytosis, and cell-cell communication. Multicolor fluorescence permits multiple targets and cell processes to be assayed in a single screen. Cross-correlation of cellular responses will yield a wealth of information required for target validation and lead optimization.

In one aspect of the present invention, a cell screening system is provided comprising a high magnification fluorescence optical system having a microscope objective, an XY stage adapted for holding a plate with an array of locations for holding cells and having a means for moving the plate to align the locations with the microscope objective and a means for moving the plate in the direction to effect focusing; a digital camera; a light source having optical means for directing excitation light to cells in the array of locations and a means for directing fluorescent light emitted from the cells to the digital camera; and a computer means for receiving and processing digital data from the digital camera wherein the computer means includes: a digital frame grabber for receiving the images from the camera, a display for user interaction and display of assay results, digital storage media for data storage and archiving, and means for control, acquisition, processing and display of results.

FIG. 1 is a schematic diagram of a preferred embodiment of the cell scanning system. An inverted fluorescence microscope is used 1, such as a Zeiss Axiovert inverted fluorescence microscope which uses standard objectives with magnification of 1-100× to the camera, and a white light source (e.g. 100 W mercury-arc lamp or 75 W xenon lamp) with power supply 2. There is an XY stage 3 to move the plate 4 in the XY direction over the microscope objective. A Z-axis focus drive 5 moves the objective in the Z direction for focusing. A joystick 6 provides for manual movement of the stage in the XYZ direction. A high resolution digital camera 7 acquires images from each well or location on the plate. There is a camera power supply 8, an automation controller 9 and a central processing unit 10. The PC 11 provides a display 12 and has associated software. The printer 13 provides for printing of a hard copy record.

FIG. 2 is a schematic of one embodiment of the microscope assembly 1 of the invention, showing in more detail the XY stage 3, Z-axis focus drive 5, joystick 6, light source 2, and automation controller 9. Cables to the computer 15 and microscope 16, respectively, are provided. In addition, FIG. 2 shows a 96 well microtiter plate 17 which is moved on the XY stage 3 in the XY direction. Light from the light source 2 passes through the PC controlled shutter 18 to a motorized filter wheel 19 with excitation filters 20. The light passes into filter cube 25 which has a dichroic mirror 26 and an emission filter 27. Excitation light reflects off the dichroic mirror to the wells in the microtiter plate 17 and fluorescent light 28 passes through the dichroic mirror 26 and the emission filter 27 and to the digital camera 7.

Figure 3:
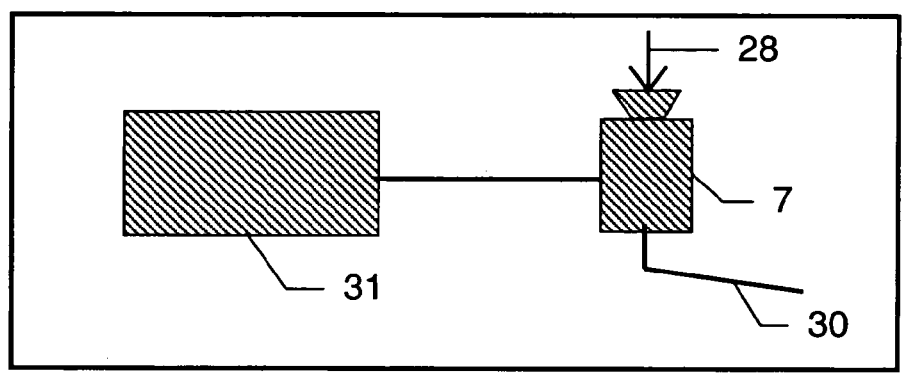
FIG. 3 shows the camera subassembly.

FIG. 3 shows a schematic drawing of a preferred camera assembly. The digital camera 7, which contains an automatic shutter for exposure control and a power supply 31, receives fluorescent light 28 from the microscope assembly. A digital cable 30 transports digital signals to the computer.

The standard optical configurations described above use microscope optics to directly produce an enlarged image of the specimen on the camera sensor in order to capture a high resolution image of the specimen. This optical system is commonly referred to as 'wide field' microscopy. Those skilled in the art of microscopy will recognize that a high resolution image of the specimen can be created by a variety of other optical systems, including, but not limited to, standard scanning confocal detection of a focused point or line of illumination scanned over the specimen (Go et al. 1997, supra), and multi-photon scanning confocal microscopy (Denk et al., 1990, supra), both of which can form images on a CCD detector or by synchronous digitization of the analog output of a photomultiplier tube.

In screening applications, it is often necessary to use a particular cell line, or primary cell culture, to take advantage of particular features of those cells. Those skilled in the art of cell culture will recognize that some cell lines are contact inhibited, meaning that they will stop growing when they become surrounded by other cells, while other cell lines will continue to grow under those conditions and the cells will literally pile up, forming many layers. An example of such a cell line is the HEK 293 (ATCC CRL-1573) line. An optical system that can acquire images of single cell layers in multilayer preparations is required for use with cell lines that tend to form layers. The large depth of field of wide field microscopes produces an image that is a projection through the many layers of cells, making analysis of subcellular spatial distributions extremely difficult in layer-forming cells. Alternatively, the very shallow depth of field that can be achieved on a confocal microscope, (about one micron), allows discrimination of a single cell layer at high resolution, simplifying the determination of the subcellular spatial distribution. Similarly, confocal imaging is preferable when detection modes such as fluorescence lifetime imaging are required.

The output of a standard confocal imaging attachment for a microscope is a digital image that can be converted to the same format as the images produced by the other cell screening system embodiments described above, and can therefore be processed in exactly the same way as those images. The overall control, acquisition and analysis in this embodiment is essentially the same. The optical configuration of the confocal microscope system, is essentially the same as that described above, except for the illuminator and detectors. Illumination and detection systems required for confocal microscopy have been designed as accessories to be attached to standard microscope optical systems such as that of the present invention (Zeiss, Germany). These alternative optical systems therefore can be easily integrated into the system as described above.

Figure 4:
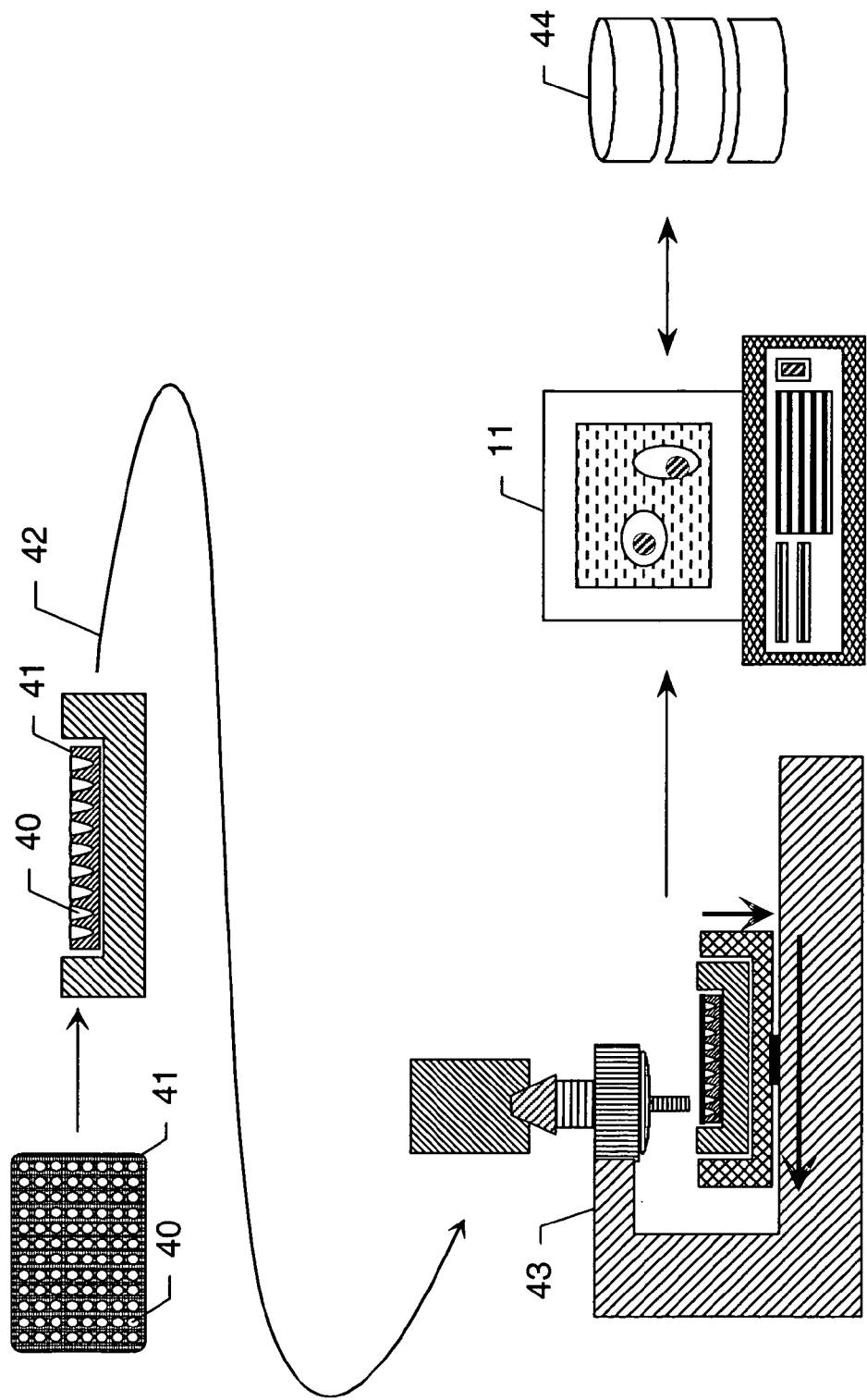
FIG. 4 illustrates cell scanning system process.

FIG. 4 illustrates an alternative embodiment of the invention in which cell arrays are in microwells 40 on a microplate 41, described in co-pending U.S. Pat. No. 6,103,479, incorporated by reference herein in its entirety. Typically the microplate is 20 mm by 30 mm as compared to a standard 96 well microtiter plate which is 86 mm by 129 mm. The higher density array of cells on a microplate allows the microplate to be imaged at a low resolution of a few microns per pixel for high throughput and particular locations on the microplate to be imaged at a higher resolution of less than 0.5 microns per pixel. These two resolution modes help to improve the overall throughput of the system.

Figure 5:
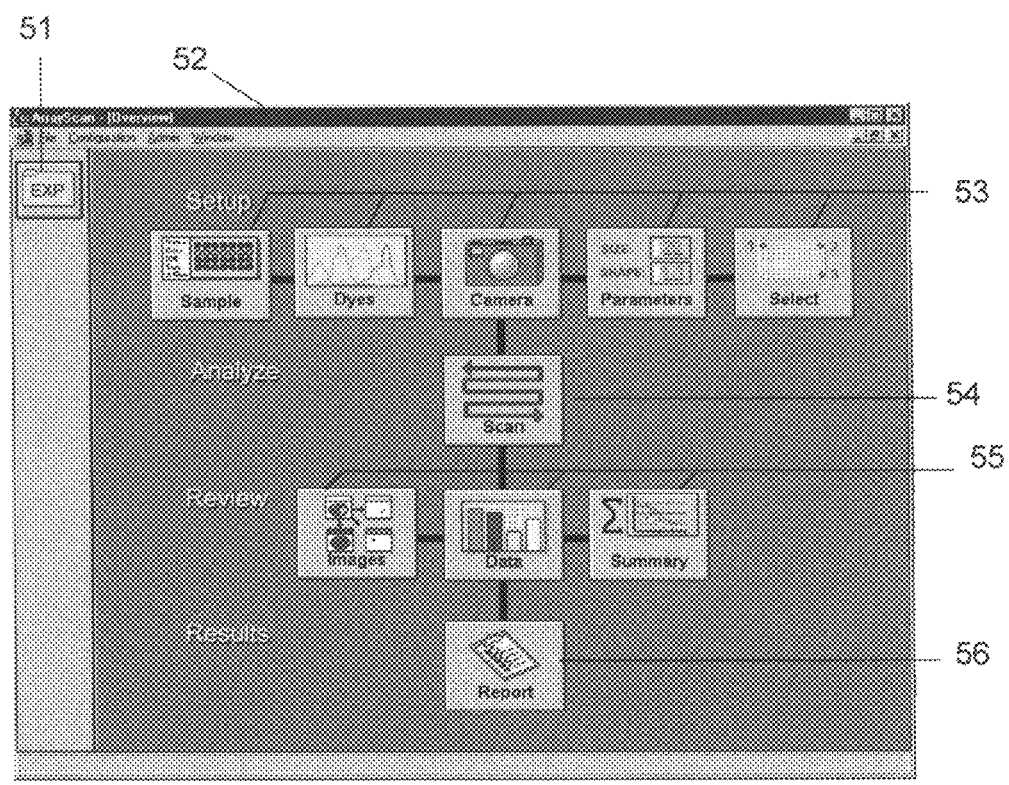
FIG. 5 illustrates a user interface showing major functions to guide the user.

The microplate chamber 42 serves as a microfluidic delivery system for the addition of compounds to cells. The microplate 41 in the microplate chamber 42 is placed in an XY microplate reader 43. Digital data is processed as described above. The small size of this microplate system increases throughput, minimizes reagent volume and allows control of the distribution and placement of cells for fast and precise cell-based analysis. Processed data can be displayed on a PC screen 11 and made part of a bioinformatics data base 44. This data base not only permits storage and retrieval of data obtained through the methods of this invention, but also permits acquisition and storage of external data relating to cells. FIG. 5 is a PC display which illustrates the operation of the software.

In an alternative embodiment, a high throughput system (HTS) is directly coupled with the HCS either on the same platform or on two separate platforms connected electronically (e.g. via a local area network). This embodiment of the invention, referred to as a dual mode optical system, has the advantage of increasing the throughput of a HCS by coupling it with a HTS and thereby requiring slower high resolution data acquisition and analysis only on the small subset of wells that show a response in the coupled HTS.

High throughput 'whole plate' reader systems are well known in the art and are commonly used as a component of an HTS system used to screen large numbers of compounds (Beggs (1997), *J. of Biomolec. Screening* 2:71-78; Macaffrey et al., (1996) *J. Biomolec. Screening* 1:187-190).

Figure 6:
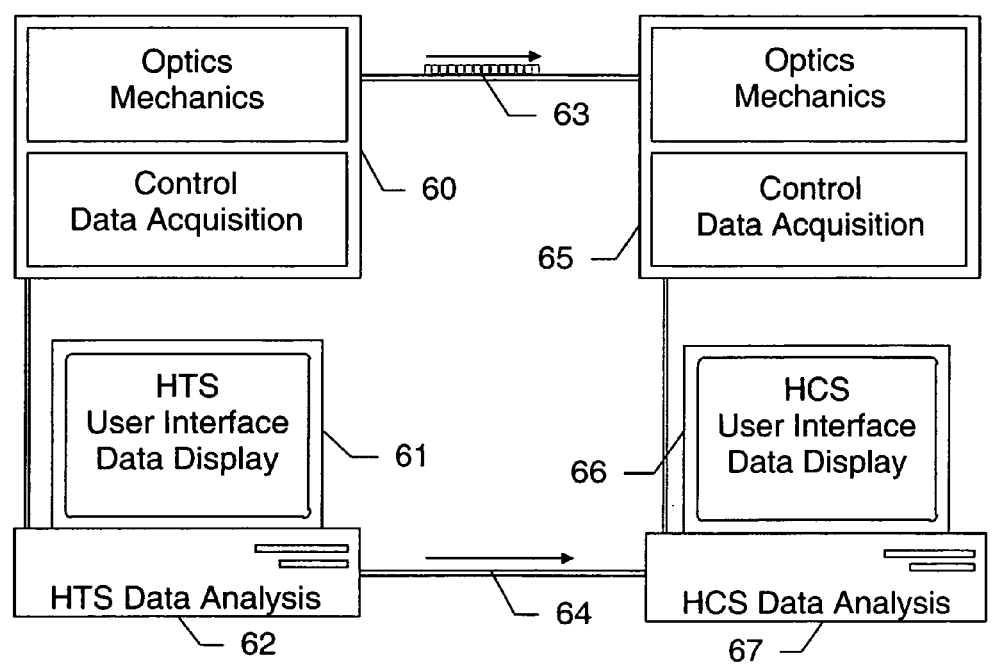
FIG. 6 is a block diagram of the two platform architecture of the Dual Mode System for Cell Based Screening in which one platform uses a telescope lens to read all wells of a microtiter plate and a second platform that uses a higher magnification lens to read individual cells in a well.

In one embodiment of dual mode cell based screening, a two platform architecture in which high throughput acquisition occurs on one platform and high content acquisition occurs on a second platform is provided (FIG. 6). Processing occurs on each platform independently, with results passed over a network interface, or a single controller is used to process the data from both platforms.

As illustrated in FIG. 6, an exemplified two platform dual mode optical system consists of two light optical instruments, a high throughput platform 60 and a high content platform 65 which read fluorescent signals emitted from cells cultured in microtiter plates or microwell arrays on a microplate, and communicate with each other via an electronic connection 64. The high throughput platform 60 analyzes all the wells in the whole plate either in parallel or rapid serial fashion. Those skilled in the art of screening will recognize that there are a many such commercially available high throughput reader systems that could be integrated into a dual mode cell based screening system (Topcount (Packard Instruments, Meriden, Conn.); Spectramax, Lumiskan (Molecular Devices, Sunnyvale, Calif.); Fluoroscan (Labsystems, Beverly, Mass.)). The high content platform 65, as described above, scans from well to well and acquires and analyzes high resolution image data collected from individual cells within a well.

The HTS software, residing on the system's computer 62, controls the high throughput instrument, and results are displayed on the monitor 61. The HCS software, residing on it's computer system 67, controls the high content instrument hardware 65, optional devices (e.g. plate loader, environmental chamber, fluid dispenser), analyzes digital image data from the plate, displays results on the monitor 66 and manages data measured in an integrated database. The two systems can also share a single computer, in which case all data would be collected, processed and displayed on that computer, without the need for a local area network to transfer the data. Microtiter plates are transferred from the high throughput system to the high content system 63 either manually or by a robotic plate transfer device, as is well known in the art (Beggs (1997), supra; Mcaffrey (1996), supra).

Figure 7:
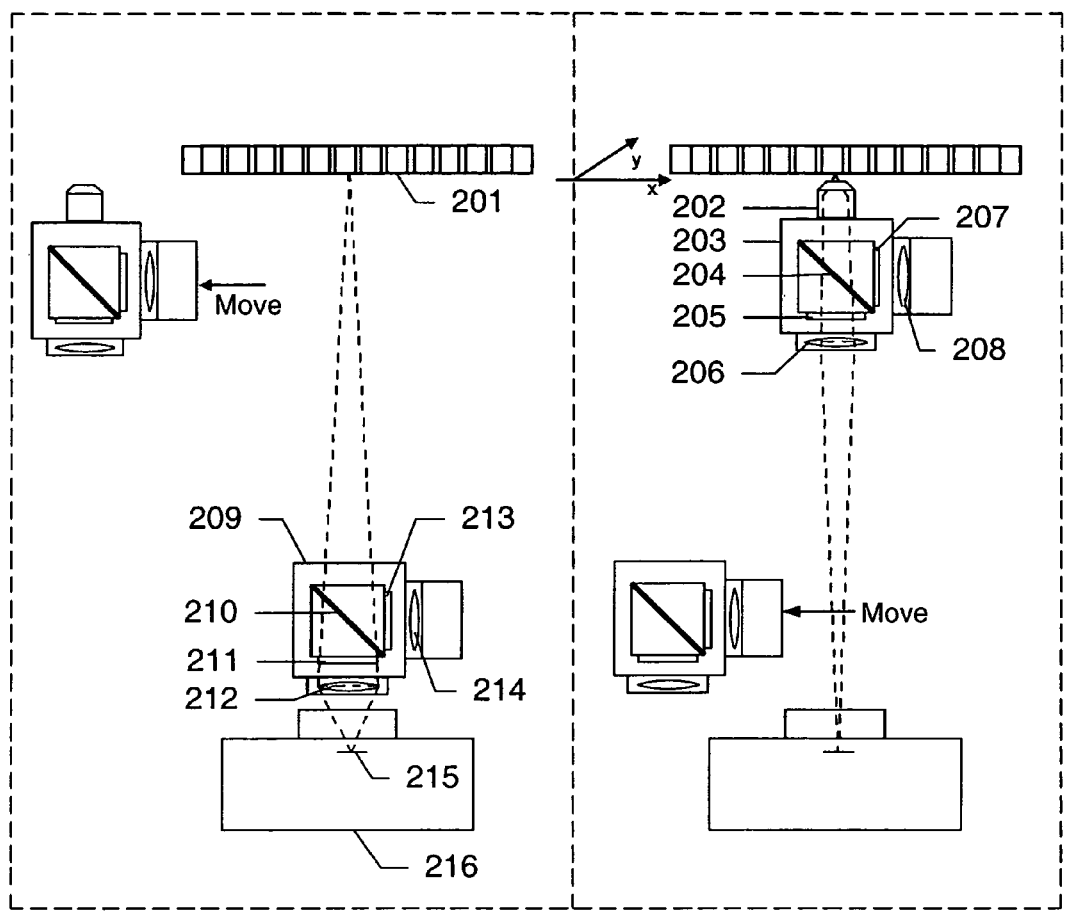
FIG. 7 is a detail of an optical system for a single platform architecture of the Dual Mode System for Cell Based Screening that uses a moveable 'telescope' lens to read all wells of a microtiter plate and a moveable higher magnification lens to read individual cells in a well.

In a preferred embodiment, the dual mode optical system utilizes a single platform system (FIG. 7). It consists of two separate optical modules, an HCS module 203 and an HTS module 209 that can be independently or collectively moved so that only one at a time is used to collect data from the microtiter plate 201. The microtiter plate 201 is mounted in a motorized X,Y stage so it can be positioned for imaging in either HTS or HCS mode. After collecting and analyzing the HTS image data as described below, the HTS optical module 209 is moved out of the optical path and the HCS optical module 203 is moved into place.

The optical module for HTS 209 consists of a projection lens 214, excitation wavelength filter 213 and dichroic mirror 210 which are used to illuminate the whole bottom of the plate with a specific wavelength band from a conventional microscope lamp system (not illustrated). The fluorescence emission is collected through the dichroic mirror 210 and emission wavelength filter 211 by a lens 212 which forms an image on the camera 216 with sensor 215.

The optical module for HCS 203 consists of a projection lens 208, excitation wavelength filter 207 and dichroic mirror 204 which are used to illuminate the back aperture of the microscope objective 202, and thereby the field of that objective, from a standard microscope illumination system (not shown). The fluorescence emission is collected by the microscope objective 202 passes through the dichroic mirror 204 and emission wavelength filter 205 and is focused by a tube lens 206 which forms an image on the same camera 216 with sensor 215.

Figure 8:
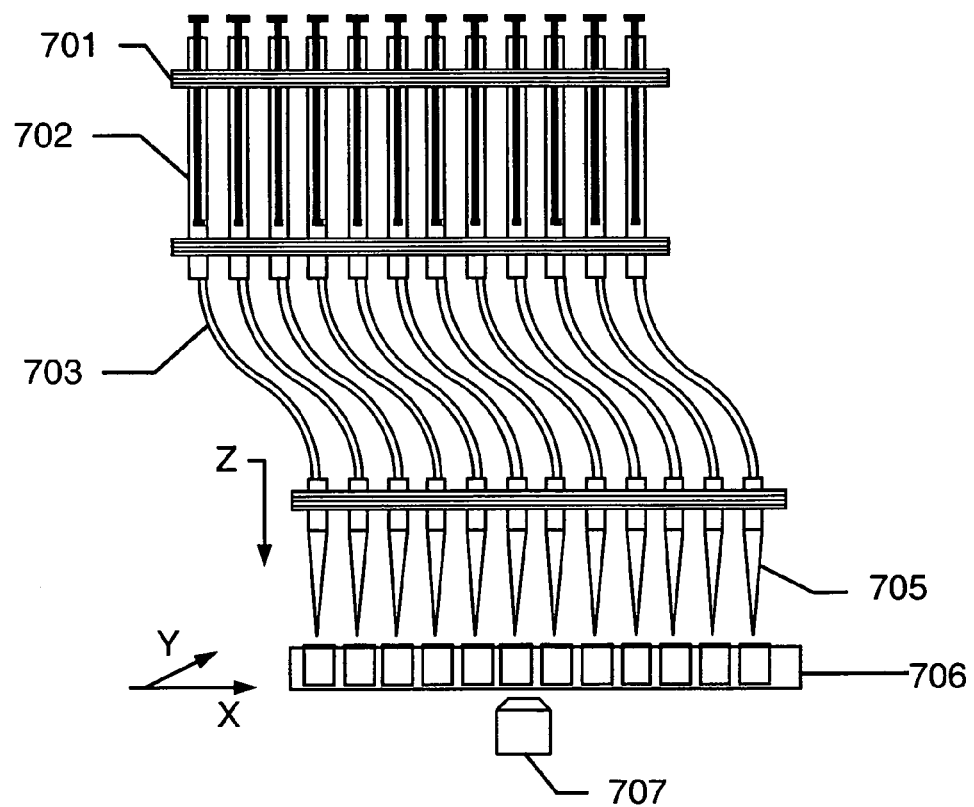
FIG. 8 is an illustration of the fluid delivery system for acquiring kinetic data on the Cell Based Screening System.

In an alternative embodiment of the present invention, the cell screening system further comprises a fluid delivery device for use with the live cell embodiment of the method of cell screening (see below). FIG. 8 exemplifies a fluid delivery device for use with the system of the invention. It consists of a bank of 12 syringe pumps 701 driven by a single motor drive. Each syringe 702 is sized according to the volume to be delivered to each well, typically between 1 and 100 μL. Each syringe is attached via flexible tubing 703 to a similar bank of connectors which accept standard pipette tips 705. The bank of pipette tips are attached to a drive system so they can be lowered and raised relative to the microtiter plate 706 to deliver fluid to each well. The plate is mounted on an X,Y stage, allowing movement relative to the optical system 707 for data collection purposes. This set-up allows one set of pipette tips, or even a single pipette tip, to deliver reagent to all the wells on the plate. The bank of syringe pumps can be used to deliver fluid to 12 wells simultaneously, or to fewer wells by removing some of the tips.

In another aspect, the present invention provides a method for analyzing cells comprising providing an array of locations which contain multiple cells wherein the cells contain one or more fluorescent reporter molecules; scanning multiple cells in each of the locations containing cells to obtain fluorescent signals from the fluorescent reporter molecule in the cells; converting the fluorescent signals into digital data; and utilizing the digital data to determine the distribution, environment or activity of the fluorescent reporter molecule within the cells.

Cell Arrays

Cell Arrays

Screening large numbers of compounds for activity with respect to a particular biological function requires preparing arrays of cells for parallel handling of cells and reagents. Standard 96 well microtiter plates which are 86 mm by 129 mm, with 6 mm diameter wells on a 9 mm pitch, are used for compatibility with current automated loading and robotic handling systems. The microplate is typically 20 mm by 30 mm, with cell locations that are 100-200 microns in dimension on a pitch of about 500 microns. Methods for making microplates are described in U.S. Pat. No. 6,103,479, incorporated by reference herein in its entirety. Microplates may consist of coplanar layers of materials to which cells adhere, patterned with materials to which cells will not adhere, or etched 3-dimensional surfaces of similarly patterted materials. For the purpose of the following discussion, the terms 'well' and 'microwell' refer to a location in an array of any construction to which cells adhere and within which the cells are imaged. Microplates may also include fluid delivery channels in the spaces between the wells. The smaller format of a microplate increases the overall efficiency of the system by minimizing the quantities of the reagents, storage and handling during preparation and the overall movement required for the scanning operation. In addition, the whole area of the microplate can be imaged more efficiently, allowing a second mode of operation for the microplate reader as described later in this document.

Fluorescence Reporter Molecules

A major component of the new drug discovery paradigm is a continually growing family of fluorescent and luminescent reagents that are used to measure the temporal and spatial distribution, content, and activity of intracellular ions, metabolites, macromolecules, and organelles. Classes of these reagents include labeling reagents that measure the distribution and amount of molecules in living and fixed cells, environmental indicators to report signal transduction events in time and space, and fluorescent protein biosensors to measure target molecular activities within living cells. A multi-parameter approach that combines several reagents in a single cell is a powerful new tool for drug discovery.

The method of the present invention is based on the high affinity of fluorescent or luminescent molecules for specific cellular components. The affinity for specific components is governed by physical forces such as ionic interactions, covalent bonding (which includes chimeric fusion with protein-based chromophores, fluorophores, and lumiphores), as well as hydrophobic interactions, electrical potential, and, in some cases, simple entrapment within a cellular component. The luminescent probes can be small molecules, labeled macromolecules, or genetically engineered proteins, including, but not limited to green fluorescent protein chimeras.

Those skilled in this art will recognize a wide variety of fluorescent reporter molecules that can be used in the present invention, including, but not limited to, fluorescently labeled biomolecules such as proteins, phospholipids and DNA hybridizing probes. Similarly, fluorescent reagents specifically synthesized with particular chemical properties of binding or association have been used as fluorescent reporter molecules (Barak et al., (1997), *J. Biol. Chem.* 272:27497-27500; Southwick et al., (1990), *Cytometry* 11:418-430; Tsien (1989) in *Methods in Cell Biology*, Vol. 29 Taylor and Wang (eds.), pp. 127-156). Fluorescently labeled antibodies are particularly useful reporter molecules due to their high degree of specificity for attaching to a single molecular target in a mixture of molecules as complex as a cell or tissue.

The luminescent probes can be synthesized within the living cell or can be transported into the cell via several non-mechanical modes including diffusion, facilitated or active transport, signal-sequence-mediated transport, and endocytotic or pinocytotic uptake. Mechanical bulk loading methods, which are well known in the art, can also be used to load luminescent probes into living cells (Barber et al. (1996), *Neuroscience Letters* 207:17-20; Bright et al. (1996), *Cytometry* 24:226-233; McNeil (1989) in *Methods in Cell Biology*, Vol. 29, Taylor and Wang (eds.), pp. 153-173). These methods include electroporation and other mechanical methods such as scrape-loading, bead-loading, impact-loading, syringe-loading, hypertonic and hypotonic loading. Additionally, cells can be genetically engineered to express reporter molecules, such as GFP, coupled to a protein of interest as previously described (Chalfie and Prasher U.S. Pat. No. 5,491,084; Cubitt et al. (1995), *Trends in Biochemical Science* 20:448-455).

Once in the cell, the luminescent probes accumulate at their target domain as a result of specific and high affinity interactions with the target domain or other modes of molecular targeting such as signal-sequence-mediated transport. Fluorescently labeled reporter molecules are useful for determining the location, amount and chemical environment of the reporter. For example, whether the reporter is in a lipophilic membrane environment or in a more aqueous environment can be determined (Giuliano et al. (1995), *Ann. Rev. of Biophysics and Biomolecular Structure* 24:405-434; Giuliano and Taylor (1995), *Methods in Neuroscience* 27:1-16). The pH environment of the reporter can be determined (Bright et al. (1989), *J. Cell Biology* 104:1019-1033; Giuliano et al. (1987), *Anal. Biochem.* 167:362-371; Thomas et al. (1979), *Biochemistry* 18:2210-2218). It can be determined whether a reporter having a chelating group is bound to an ion, such as Ca++, or not (Bright et al. (1989), In *Methods in Cell Biology*, Vol. 30, Taylor and Wang (eds.), pp. 157-192; Shimoura et al. (1988), *J. of Biochemistry* (Tokyo) 251:405-410; Tsien (1989) In *Methods in Cell Biology*, Vol. 30, Taylor and Wang (eds.), pp. 127-156).

Furthermore, certain cell types within an organism may contain components that can be specifically labeled that may not occur in other cell types. For example, epithelial cells often contain polarized membrane components. That is, these cells asymmetrically distribute macromolecules along their plasma membrane. Connective or supporting tissue cells often contain granules in which are trapped molecules specific to that cell type (e.g., heparin, histamine, serotonin, etc.). Most muscular tissue cells contain a sarcoplasmic reticulum, a specialized organelle whose function is to regulate the concentration of calcium ions within the cell cytoplasm. Many nervous tissue cells contain secretory granules and vesicles in which are trapped neurohormones or neurotransmitters. Therefore, fluorescent molecules can be designed to label not only specific components within specific cells, but also specific cells within a population of mixed cell types.

Those skilled in the art will recognize a wide variety of ways to measure fluorescence. For example, some fluorescent reporter molecules exhibit a change in excitation or emission spectra, some exhibit resonance energy transfer where one fluorescent reporter loses fluorescence, while a second gains in fluorescence, some exhibit a loss (quenching) or appearance of fluorescence, while some report rotational movements (Giuliano et al. (1995), *Ann. Rev. of Biophysics and Biomol. Structure* 24:405-434; Giuliano et al. (1995), *Methods in Neuroscience* 27:1-16).

Scanning Cell Arrays

Figure 9:
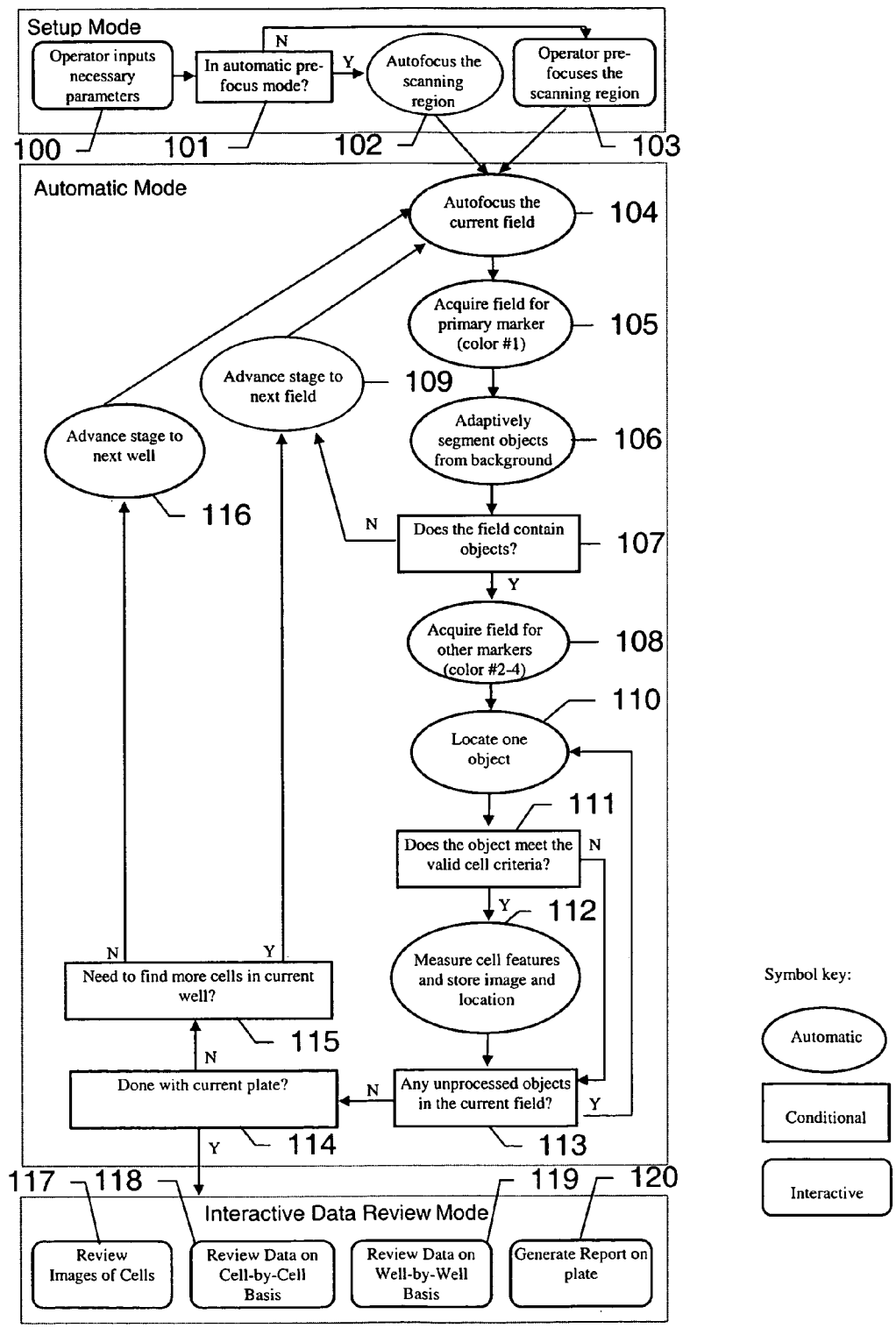
FIG. 9 is a flow chart of processing step for the cell-based scanning system.

Referring to FIG. 9, a preferred embodiment is provided to analyze cells that comprises operator-directed parameters being selected based on the assay being conducted, data acquisition by the cell screening system on the distribution of fluorescent signals within a sample, and interactive data review and analysis. At the start of an automated scan the operator enters information 100 that describes the sample, specifies the filter settings and fluorescent channels to match the biological labels being used and the information sought, and then adjusts the camera settings to match the sample brightness. For flexibility to handle a range of samples, the software allows selection of various parameter settings used to identify nuclei and cytoplasm, and selection of different fluorescent reagents, identification of cells of interest based on morphology or brightness, and cell numbers to be analyzed per well. These parameters are stored in the system's for easy retrieval for each automated run. The system's interactive cell identification mode simplifies the selection of morphological parameter limits such as the range of size, shape, and intensity of cells to be analyzed. The user specifies which wells of the plate the system will scan and how many fields or how many cells to analyze in each well. Depending on the setup mode selected by the user at step 101, the system either automatically pre-focuses the region of the plate to be scanned using an autofocus procedure to "find focus" of the plate 102 or the user interactively pre-focuses 103 the scanning region by selecting three "tag" points which define the rectangular area to be scanned. A least-squares fit "focal plane model" is then calculated from these tag points to estimate the focus of each well during an automated scan. The focus of each well is estimated by interpolating from the focal plane model during a scan.

During an automated scan, the software dynamically displays the scan status, including the number of cells analyzed, the current well being analyzed, images of each independent wavelength as they are acquired, and the result of the screen for each well as it is determined. The plate 4 (FIG. 1) is scanned in a serpentine style as the software automatically moves the motorized microscope XY stage 3 from well to well and field to field within each well of a 96-well plate. Those skilled in the programming art will recognize how to adapt software for scanning of other microplate formats such as 24, 48, and 384 well plates. The scan pattern of the entire plate as well as the scan pattern of fields within each well are programmed. The system adjusts sample focus with an autofocus procedure 104 (FIG. 9) through the Z axis focus drive 5, controls filter selection via a motorized filter wheel 19 and acquires and analyzes images of up to four different colors ("channels" or "wavelengths").

The autofocus procedure is called at a user selected frequency, typically for the first field in each well and then once every 4 to 5 fields within each well. The autofocus procedure calculates the starting Z-axis point by interpolating from the pre-calculated plane focal model. Starting a programmable distance above or below this set point, the procedure moves the mechanical Z-axis through a number of different positions, acquires an image at each position, and finds the maximum of a calculated focus score that estimates the contrast of each image. The Z position of the image with the maximum focus score determines the best focus for a particular field. Those skilled in the art will recognize this as a variant of automatic focusing methods as described in Harms et al. in *Cytometry* 5 (1984), 236-243, Groen et al. in *Cytometry* 6 (1985), 81-91, and Firestone et al. in *Cytometry* 12 (1991), 195-206.

For image acquisition, the camera's exposure time is separately adjusted for each dye to ensure a high-quality image from each channel. Software procedures can be called, at the user's option, to correct for registration shifts between wavelengths by accounting for linear (X and Y) shifts between wavelengths before making any further measurements. The electronic shutter 18 is controlled so that sample photobleaching is kept to a minimum. Background shading and uneven illumination can be corrected by the software using methods known in the art (Bright et al. (1987), *J. Cell Biol.* 104:1019-1033).

In one channel, images are acquired of a primary marker 105 (FIG. 9) (typically cell nuclei counterstained with DAPI or PI fluorescent dyes) which are segmented ("identified") using an adaptive thresholding procedure. The adaptive thresholding procedure 106 is used to dynamically select the threshold of an image for separating cells from the background. The staining of cells with fluorescent dyes can vary to an unknown degree across cells in a microtiter plate sample as well as within images of a field of cells within each well of a microtiter plate. This variation can occur as a result of sample preparation and/or the dynamic nature of cells. A global threshold is calculated for the complete image to separate the cells from background and account for field to field variation. These global adaptive techniques are variants of those described in the art. (Kittler et al. in *Computer Vision, Graphics, and Image Processing* 30 (1985), 125-147, Ridler et al. in *IEEE Trans. Systems, Man, and Cybernetics* (1978), 630-632.)

An alternative adaptive thresholding method utilizes local region thresholding in contrast to global image thresholding. Image analysis of local regions leads to better overall segmentation since staining of cell nuclei (as well as other labeled components) can vary across an image. Using this global/local procedure, a reduced resolution image (reduced in size by a factor of 2 to 4) is first globally segmented (using adaptive thresholding) to find regions of interest in the image. These regions then serve as guides to more fully analyze the same regions at full resolution. A more localized threshold is then calculated (again using adaptive thresholding) for each region of interest.

The output of the segmentation procedure is a binary image wherein the objects are white and the background is black. This binary image, also called a mask in the art, is used to determine if the field contains objects 107. The mask is labeled with a blob labeling method whereby each object (or blob) has a unique number assigned to it. Morphological features, such as area and shape, of the blobs are used to differentiate blobs likely to be cells from those that are considered artifacts. The user pre-sets the morphological selection criteria by either typing in known cell morphological features or by using the interactive training utility. If objects of interest are found in the field, images are acquired for all other active channels 108 otherwise the stage is advanced to the next field 109 in the current well. Each object of interest is located in the image for further analysis 110. The software determines if the object meets the criteria for a valid cell nucleus 111 by measuring its morphological features (size and shape). For each valid cell, the XYZ stage location is recorded, a small image of the cell is stored, and features are measured 112.

Figure 10:
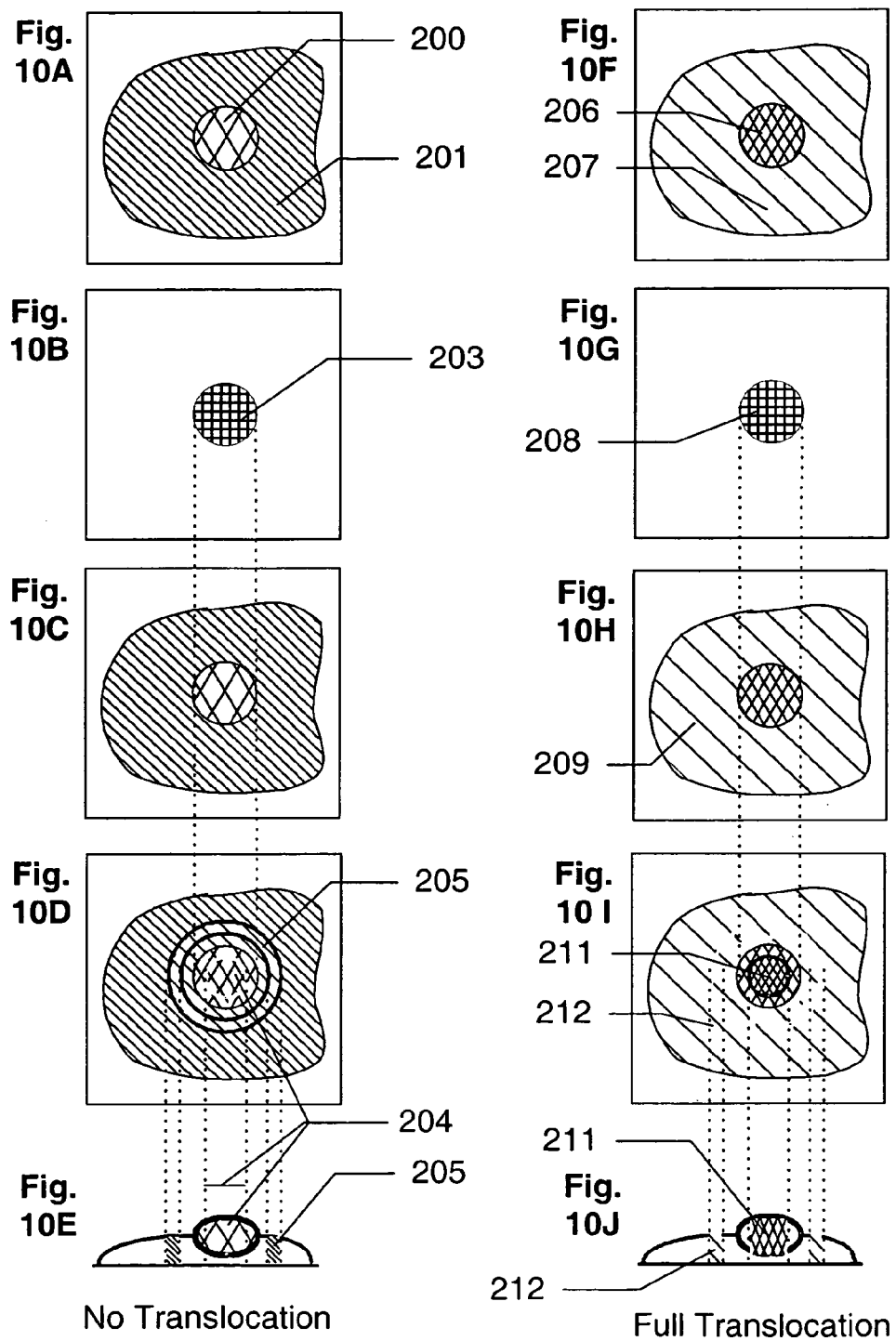
FIG. 10 A-J illustrates the strategy of the Nuclear Translocation Assay.

The cell scanning method of the present invention can be used to perform many different assays on cellular samples by applying a number of analytical methods simultaneously to measure features at multiple wavelengths. An example of one such assay provides for the following measurements:

1. The total fluorescent intensity within the cell nucleus for colors 1-4
2. The area of the cell nucleus for color 1 (the primary marker)
3. The shape of the cell nucleus for color 1 is described by three shape features:
   a) perimeter squared area
   b) box area ratio
   c) height width ratio
4. The average fluorescent intensity within the cell nucleus for colors 1-4 (i.e. #1 divided by #2)
5. The total fluorescent intensity of a ring outside the nucleus (see FIG. 10) that represents fluorescence of the cell's cytoplasm (cytoplasmic mask) for colors 2-4
6. The area of the cytoplasmic mask
7. The average fluorescent intensity of the cytoplasmic mask for colors 2-4 (i.e. #5 divided by #6)
8. The ratio of the average fluorescent intensity of the cytoplasmic mask to average fluorescent intensity within the cell nucleus for colors 2-4 (i.e. #7 divided by #4)
9. The difference of the average fluorescent intensity of the cytoplasmic mask and the average fluorescent intensity within the cell nucleus for colors 2-4 (i.e. #7 minus #4)
10. The number of fluorescent domains (also call spots, dots, or grains) within the cell nucleus for colors 2-4

Features 1 through 4 are general features of the different cell screening assays of the invention. These steps are commonly used in a variety of image analysis applications and are well known in art (Russ (1992) *The Image Processing Handbook*, CRC Press Inc.; Gonzales et al. (1987), *Digital Image Processing*. Addison-Wesley Publishing Co. pp. 391-448). Features 5-9 have been developed specifically to provide measurements of a cell's fluorescent molecules within the local cytoplasmic region of the cell and the translocation (i.e. movement) of fluorescent molecules from the cytoplasm to the nucleus. These features (steps 5-9) are used for analyzing cells in microplates for the inhibition of nuclear translocation. For example, inhibition of nuclear translocation of transcription factors provides a novel approach to screening intact cells (detailed examples of other types of screens will be provided below). A specific method measures the amount of probe in the nuclear region (feature 4) versus the local cytoplasmic region (feature 7) of each cell. Quantification of the difference between these two sub-cellular compartments provides a measure of cytoplasm-nuclear translocation (feature 9).

Feature 10 describes a screen used for counting of DNA or RNA probes within the nuclear region in colors 2-4. For example, probes are commercially available for identifying chromosome-specific DNA sequences (Life Technologies, Gaithersburg, Md.; Genosys, Woodlands, Tex.; Biotechnologies, Inc., Richmond, Calif.; Bio 101, Inc., Vista, Calif.) Cells are three-dimensional in nature and when examined at a high magnification under a microscope one probe may be in-focus while another may be completely out-of-focus. The cell screening method of the present invention provides for detecting three-dimensional probes in nuclei by acquiring images from multiple focal planes. The software moves the Z-axis motor drive 5 (FIG. 1) in small steps where the step distance is user selected to account for a wide range of different nuclear diameters. At each of the focal steps, an image is acquired. The maximum gray-level intensity from each pixel in each image is found and stored in a resulting maximum projection image. The maximum projection image is then used to count the probes. The above method works well in counting probes that are not stacked directly above or below another one. To account for probes stacked on top of each other in the Z-direction, users can select an option to analyze probes in each of the focal planes acquired. In this mode, the scanning system performs the maximum plane projection method as discussed above, detects probe regions of interest in this image, then further analyzes these regions in all the focal plane images.

After measuring cell features 112 (FIG. 9), the system checks if there are any unprocessed objects in the current field 113. If there are any unprocessed objects, it locates the next object 110 and determines whether it meets the criteria for a valid cell nucleus 111, and measures its features. Once all the objects in the current field are processed, the system determines whether analysis of the current plate is complete 114; if not, it determines the need to find more cells in the current well 115. If the need exists, the system advances the XYZ stage to the next field within the current well 109 or advances the stage to the next well 116 of the plate.

After a plate scan is complete, images and data can be reviewed with the system's image review, data review, and summary review facilities. All images, data, and settings from a scan are archived in the system's database for later review or for interfacing with a network information management system. Data can also be exported to other third-party statistical packages to tabulate results and generate other reports. Users can review the images alone of every cell analyzed by the system with an interactive image review procedure 117. The user can review data on a cell-by-cell basis using a combination of interactive graphs, a data spreadsheet of measured features, and images of all the fluorescence channels of a cell of interest with the interactive cell-by-cell data review procedure 118. Graphical plotting capabilities are provided in which data can be analyzed via interactive graphs such as histograms and scatter plots. Users can review summary data that are accumulated and summarized for all cells within each well of a plate with an interactive well-by-well data review procedure 119. Hard copies of graphs and images can be printed on a wide range of standard printers.

As a final phase of a complete scan, reports can be generated on one or more statistics of the measured features. Users can generate a graphical report of data summarized on a well-by-well basis for the scanned region of the plate using an interactive report generation procedure 120. This report includes a summary of the statistics by well in tabular and graphical format and identification information on the sample. The report window allows the operator to enter comments about the scan for later retrieval. Multiple reports can be generated on many statistics and be printed with the touch of one button. Reports can be previewed for placement and data before being printed.

The above-recited embodiment of the method operates in a single high resolution mode referred to as the high content screening (HCS) mode. The HCS mode provides sufficient spatial resolution within a well (on the order of 1 μm) to define the distribution of material within the well, as well as within individual cells in the well. The high degree of information content accessible in that mode, comes at the expense of speed and complexity of the required signal processing.

In an alternative embodiment, a high throughput system (HTS) is directly coupled with the HCS either on the same platform or on two separate platforms connected electronically (e.g. via a local area network). This embodiment of the invention, referred to as a dual mode optical system, has the advantage of increasing the throughput of an HCS by coupling it with an HTS and thereby requiring slower high resolution data acquisition and analysis only on the small subset of wells that show a response in the coupled HTS.

Figure 11:
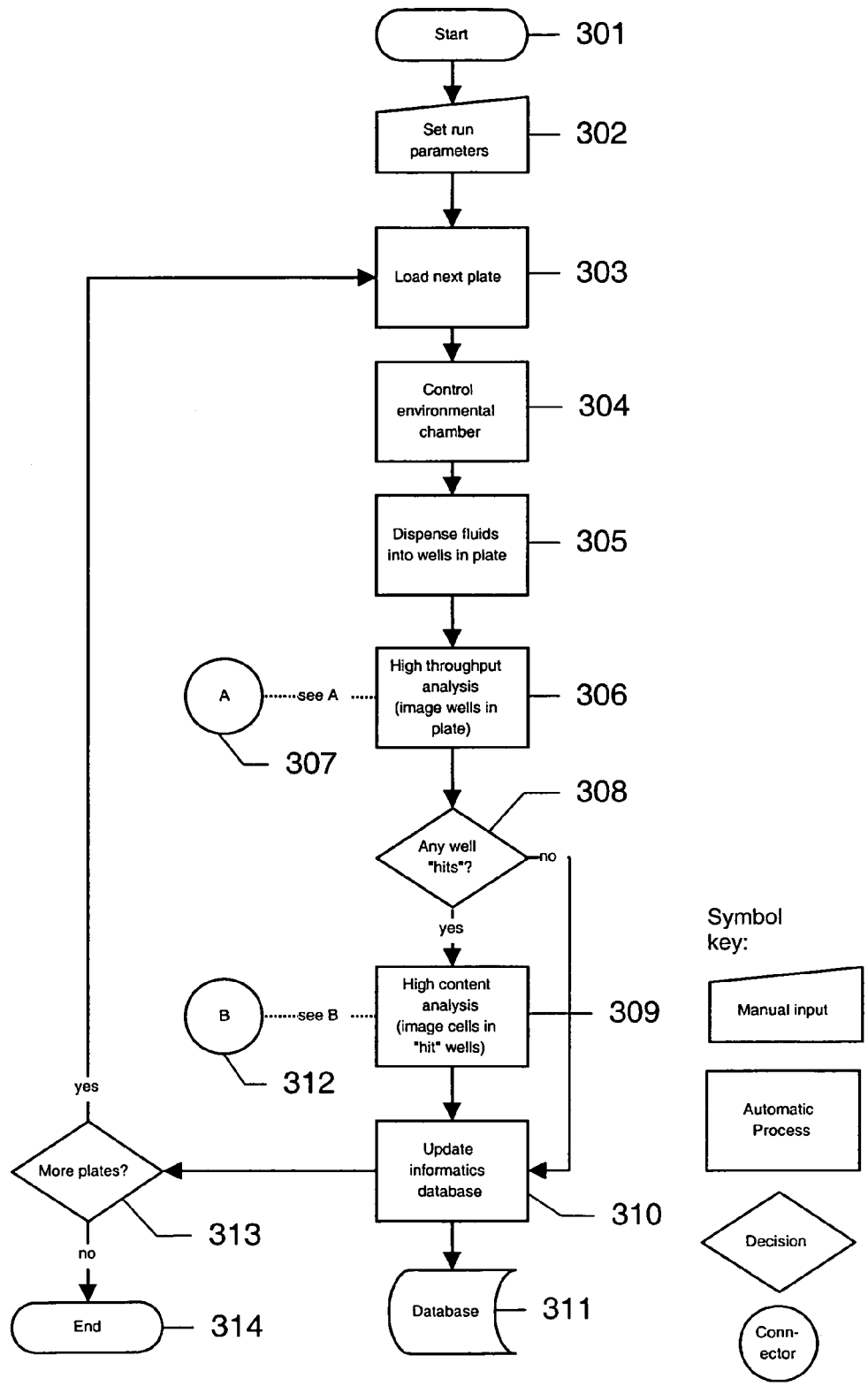
FIG. 11 is a flow chart defining the processing steps in the Dual Mode System for Cell Based Screening combining high throughput and high content screening of microtiter plates.

High throughput 'whole plate' reader systems are well known in the art and are commonly used as a component of an HTS system used to screen large numbers of compounds (Beggs et al. (1997), supra; McCaffrey et al. (1996), supra). The HTS of the present invention is carried out on the microtiter plate or microwell array by reading many or all wells in the plate simultaneously with sufficient resolution to make determinations on a well-by-well basis. That is, calculations are made by averaging the total signal output of many or all the cells or the bulk of the material in each well. Wells that exhibit some defined response in the HTS (the 'hits') are flagged by the system. Then on the same microtiter plate or microwell array, each well identified as a hit is measured via HCS as described above. Thus, the dual mode process involves:

1. Rapidly measuring numerous wells of a microtiter plate or microwell array,
2. Interpreting the data to determine the overall activity of fluorescently labeled reporter molecules in the cells on a well-by-well basis to identify "hits" (wells that exhibit a defined response),
3. Imaging numerous cells in each "hit" well, and
4. Interpreting the digital image data to determine the distribution, environment or activity of the fluorescently labeled reporter molecules in the individual cells (i.e. intracellular measurements) and the distribution of the cells to test for specific biological functions In a preferred embodiment of dual mode processing (FIG. 11), at the start of a run 301, the operator enters information 302 that describes the plate and its contents, specifies the filter settings and fluorescent channels to match the biological labels being used, the information sought and the camera settings to match the sample brightness. These parameters are stored in the system's database for easy retrieval for each automated run. The microtiter plate or microwell array is loaded into the cell screening system 303 either manually or automatically by controlling a robotic loading device. An optional environmental chamber 304 is controlled by the system to maintain the temperature, humidity and $CO_2$ levels in the air surrounding live cells in the microtiter plate or microwell array. An optional fluid delivery device 305 (see FIG. 8) is controlled by the system to dispense fluids into the wells during the scan.

Figure 12:
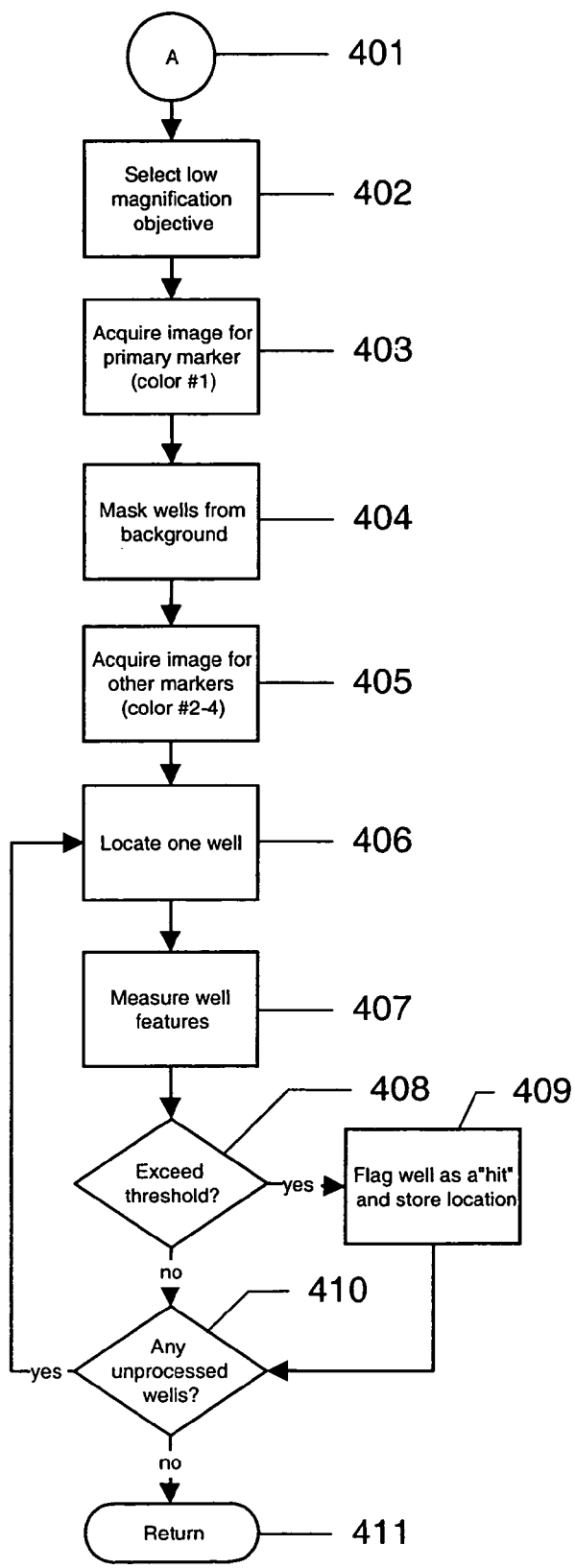
FIG. 12 is a flow chart defining the processing steps in the High Throughput mode of the System for Cell Based Screening.
Figure 13:
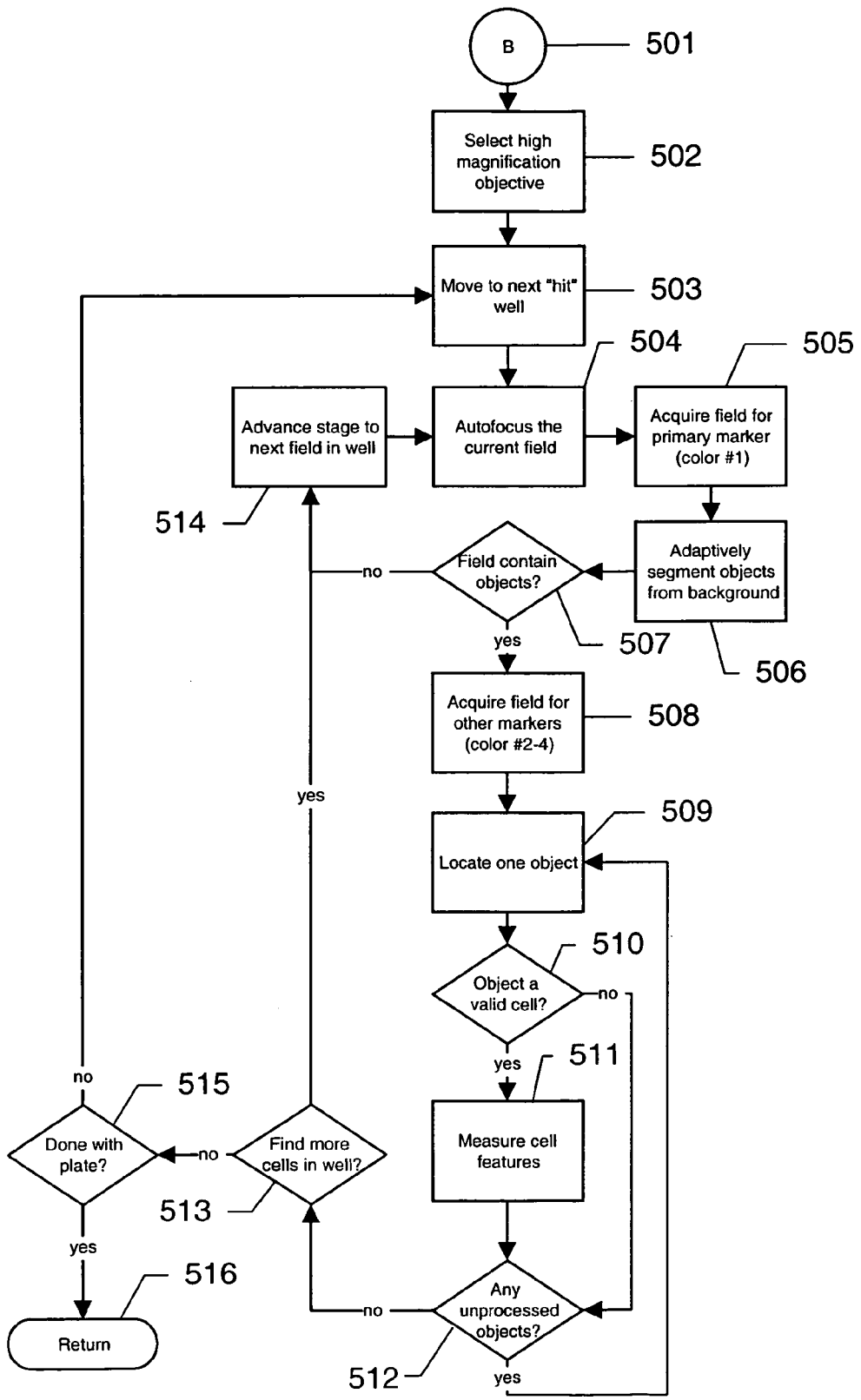
FIG. 13 is a flow chart defining the processing steps in the High Content mode of the System for Cell Based Screening.

High throughput processing 306 is first performed on the microtiter plate or microwell array by acquiring and analyzing the signal from each of the wells in the plate. The processing performed in high throughput mode 307 is illustrated in FIG. 12 and described below. Wells that exhibit some selected intensity response in this high throughput mode ("hits") are identified by the system. The system performs a conditional operation 308 that tests for hits. If hits are found, those specific hit wells are further analyzed in high content (micro level) mode 309. The processing performed in high content mode 312 is illustrated in FIG. 13. The system then updates 310 the informatics database 311 with results of the measurements on the plate. If there are more plates to be analyzed 313 the system loads the next plate 303; otherwise the analysis of the plates terminates 314.

The following discussion describes the high throughput mode illustrated in FIG. 12. The preferred embodiment of the system, the single platform dual mode screening system, will be described. Those skilled in the art will recognize that operationally the dual platform system simply involves moving the plate between two optical systems rather than moving the optics. Once the system has been set up and the plate loaded, the system begins the HTS acquisition and analysis 401. The HTS optical module is selected by controlling a motorized optical positioning device 402 on the dual mode system. In one fluorescence channel, data from a primary marker on the plate is acquired 403 and wells are isolated from the plate background using a masking procedure 404. Images are also acquired in other fluorescence channels being used 405. The region in each image corresponding to each well 406 is measured 407. A feature calculated from the measurements for a particular well is compared with a predefined threshold or intensity response 408, and based on the result the well is either flagged as a "hit" 409 or not. The locations of the wells flagged as hits are recorded for subsequent high content mode processing. If there are wells remaining to be processed 410 the program loops back 406 until all the wells have been processed 411 and the system exits high throughput mode.

Following HTS analysis, the system starts the high content mode processing 501 defined in FIG. 13. The system selects the HCS optical module 502 by controlling the motorized positioning system. For each "hit" well identified in high throughput mode, the XY stage location of the well is retrieved from memory or disk and the stage is then moved to the selected stage location 503. The autofocus procedure 504 is called for the first field in each hit well and then once every 5 to 8 fields within each well. In one channel, images are acquired of the primary marker 505 (typically cell nuclei counterstained with DAPI, Hoechst or PI fluorescent dye). The images are then segmented (separated into regions of nuclei and non-nuclei) using an adaptive thresholding procedure 506. The output of the segmentation procedure is a binary mask wherein the objects are white and the background is black. This binary image, also called a mask in the art, is used to determine if the field contains objects 507. The mask is labeled with a blob labeling method whereby each object (or blob) has a unique number assigned to it. If objects are found in the field, images are acquired for all other active channels 508, otherwise the stage is advanced to the next field 514 in the current well. Each object is located in the image for further analysis 509. Morphological features, such as area and shape of the objects, are used to select objects likely to be cell nuclei 510, and discard (do no further processing on) those that are considered artifacts. For each valid cell nucleus, the XYZ stage location is recorded, a small image of the cell is stored, and assay specific features are measured 511. The system then performs multiple tests on the cells by applying several analytical methods to measure features at each of several wavelengths. After measuring the cell features, the systems checks if there are any unprocessed objects in the current field 512. If there are any unprocessed objects, it locates the next object 509 and determines whether it meets the criteria for a valid cell nucleus 510 and measures its features. After processing all the objects in the current field, the system deterermines whether it needs to find more cells or fields in the current well 513. If it needs to find more cells or fields in the current well it advances the XYZ stage to the next field within the current well 515. Otherwise, the system checks whether it has any remaining hit wells to measure 515. If so, it advances to the next hit well 503 and proceeds through another cycle of acquisition and analysis, otherwise the HCS mode is finished 516.

In an alternative embodiment of the present invention, a method of kinetic live cell screening is provided. The previously described embodiments of the invention are used to characterize the spatial distribution of cellular components at a specific point in time, the time of chemical fixation. As such, these embodiments have limited utility for implementing kinetic based screens, due to the sequential nature of the image acquisition, and the amount of time required to read all the wells on a plate. For example, since a plate can require 30-60 minutes to read through all the wells, only very slow kinetic processes can be measured by simply preparing a plate of live cells and then reading through all the wells more than once. Faster kinetic processes can be measured by taking multiple readings of each well before proceeding to the next well, but the elapsed time between the first and last well would be too long, and fast kinetic processes would likely be complete before reaching the last well.

The kinetic live cell extension of the invention enables the design and use of screens in which a biological process is characterized by its kinetics instead of, or in addition to, its spatial characteristics. In many cases, a response in live cells can be measured by adding a reagent to a specific well and making multiple measurements on that well with the appropriate timing. This dynamic live cell embodiment of the invention therefore includes apparatus for fluid delivery to individual wells of the system in order to deliver reagents to each well at a specific time in advance of reading the well. This embodiment thereby allows kinetic measurements to be made with temporal resolution of seconds to minutes on each well of the plate. To improve the overall efficiency of the dynamic live cell system, the acquisition control program is modified to allow repetitive data collection from sub-regions of the plate, allowing the system to read other wells between the time points required for an individual well.

FIG. 8 describes an example of a fluid delivery device for use with the live cell embodiment of the invention and is described above. This set-up allows one set of pipette tips 705 or even a single pipette tip, to deliver reagent to all the wells on the plate. The bank of syringe pumps 701 can be used to deliver fluid to 12 wells simultaneously, or to fewer wells by removing some of the tips 705. The temporal resolution of the system can therefore be adjusted, without sacrificing data collection efficiency, by changing the number of tips and the scan pattern as follows. Typically, the data collection and analysis from a single well takes about 5 seconds. Moving from well to well and focusing in a well requires about 5 seconds, so the overall cycle time for a well is about 10 seconds. Therefore, if a single pipette tip is used to deliver fluid to a single well, and data is collected repetitively from that well, measurements can be made with about 5 seconds temporal resolution. If 6 pipette tips are used to deliver fluids to 6 wells simultaneously, and the system repetitively scans all 6 wells, each scan will require 60 seconds, thereby establishing the temporal resolution. For slower processes which only require data collection every 8 minutes, fluids can be delivered to one half of the plate, by moving the plate during the fluid delivery phase, and then repetitively scanning that half of the plate. Therefore, by adjusting the size of the sub-region being scanned on the plate, the temporal resolution can be adjusted without having to insert wait times between acquisitions. Because the system is continuously scanning and acquiring data, the overall time to collect a kinetic data set from the plate is then simply the time to perform a single scan of the plate, multiplied by the number of time points required. Typically, 1 time point before addition of compounds and 2 or 3 time points following addition should be sufficient for screening purposes.

Figure 14:
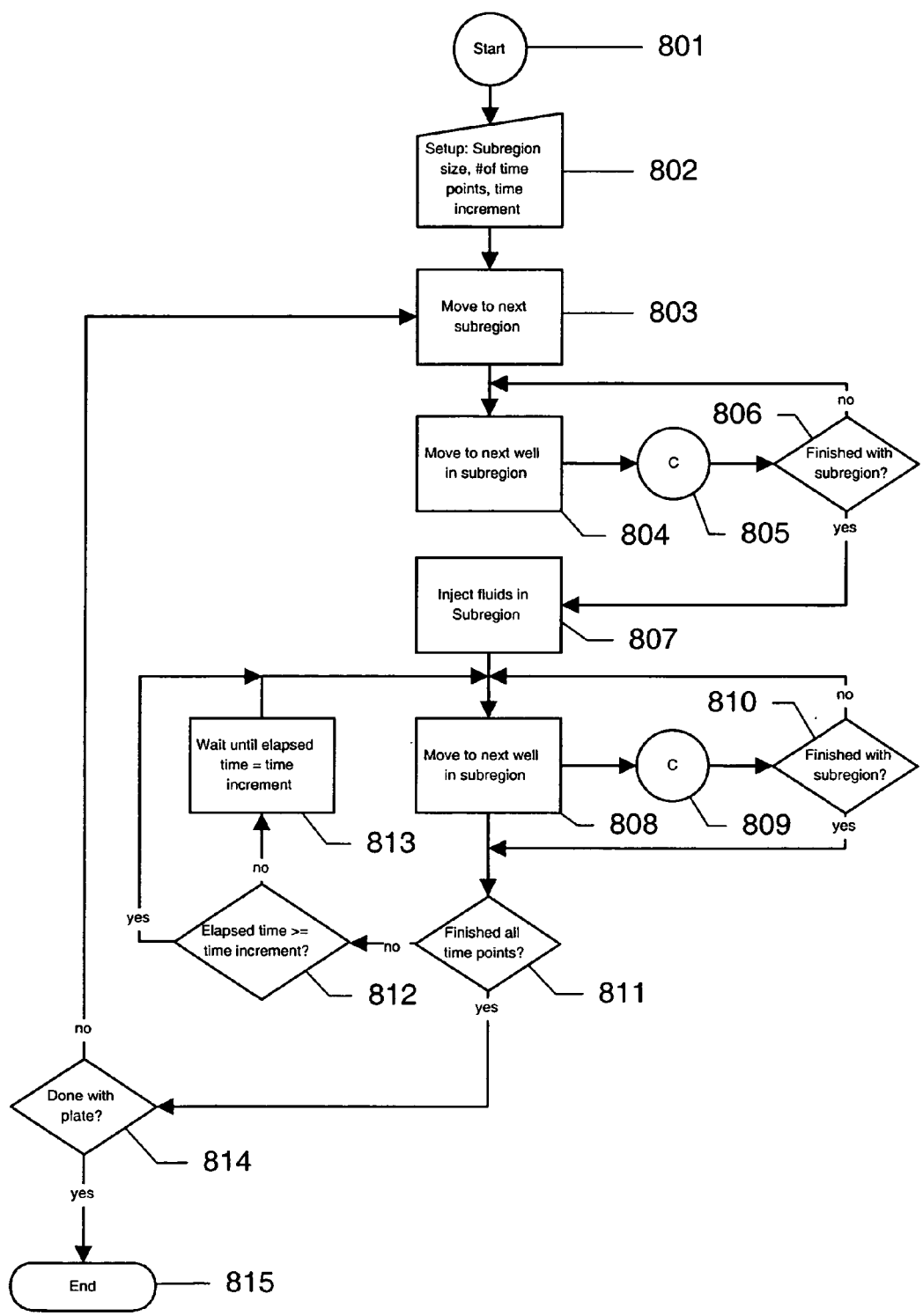
FIG. 14 is a flow chart defining the processing steps required for acquiring kinetic data in the High Content mode of the System for Cell Based Screening.
Figure 15:
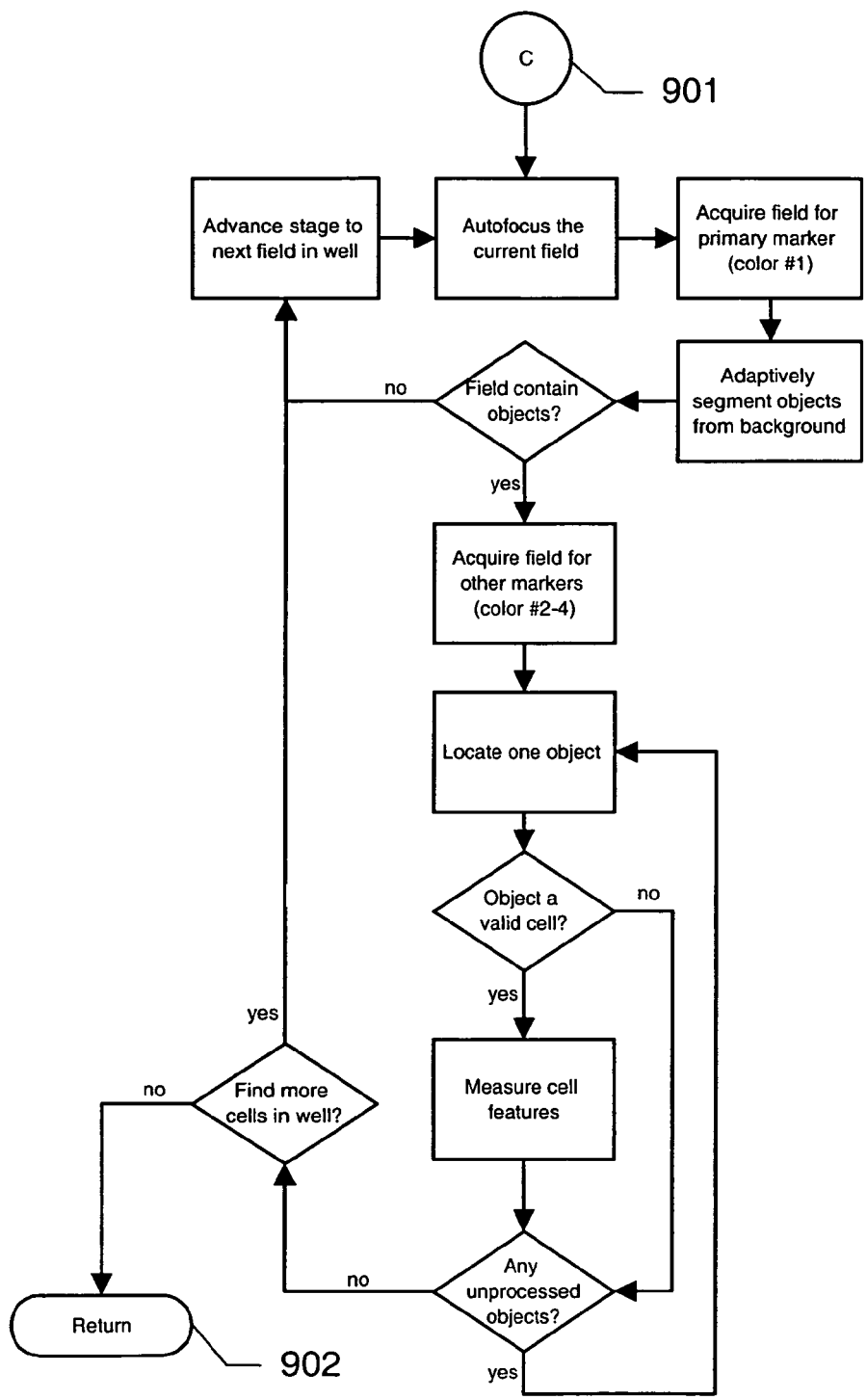
FIG. 15 is a flow chart defining the processing steps performed within a well during the acquisition of kinetic data.

FIG. 14 shows the acquisition sequence used for kinetic analysis. The start of processing 801 is configuration of the system, much of which is identical to the standard HCS configuration. In addition, the operator must enter information specific to the kinetic analysis being performed 802, such as the sub-region size, the number of time points required, and the required time increment. A sub-region is a group of wells that will be scanned repetitively in order to accumulate kinetic data. The size of the sub-region is adjusted so that the system can scan a whole sub-region once during a single time increment, thus minimizing wait times. The optimum sub-region size is calculated from the setup parameters, and adjusted if necessary by the operator. The system then moves the plate to the first sub-region 803, and to the first well in that sub-region 804 to acquire the prestimulation (time=0) time points. The acquisition sequence per-formed in each well is exactly the same as that required for the specific HCS being run in kinetic mode. FIG. 15 details a flow chart for that processing. All of the steps between the start 901 and the return 902 are identical to those described as steps 504-514 in FIG. 13.

After processing each well in a sub-region, the system checks to see if all the wells in the sub-region have been processed 806 (FIG. 14), and cycles through all the wells until the whole region has been processed. The system then moves the plate into position for fluid addition, and controls fluidic system delivery of fluids to the entire sub-region 807. This may require multiple additions for sub-regions which span several rows on the plate, with the system moving the plate on the XY stage between additions. Once the fluids have been added, the system moves to the first well in the sub-region 808 to begin acquisition of time points. The data is acquired from each well 809 and as before the system cycles through all the wells in the sub-region 810. After each pass through the sub-region, the system checks whether all the time points have been collected 811 and if not, pauses 813 if necessary 812 to stay synchronized with the requested time increment. Otherwise, the system checks for additional sub-regions on the plate 814 and either moves to the next sub-region 803 or finishes 815. Thus, the kinetic analysis mode comprises operator identification of sub-regions of the microtiter plate or microwells to be screened, based on the kinetic response to be investigated, with data acquisitions within a sub-region prior to data acquisition in subsequent sub-regions.

Specific Screens

In another aspect of the present invention, cell screening methods and machine readable storage medium comprising a program containing a set of instructions for causing a cell screening system to execute procedures for defining the distribution and activity of specific cellular constituents and processes is provided. In a preferred embodiment, the cell screening system comprises a high magnification fluorescence optical system with a stage adapted for holding cells and a means for moving the stage, a digital camera, a light source for receiving and processing the digital data from the digital camera, and a computer means for receiving and processing the digital data from the digital camera. This aspect of the invention comprises programs that instruct the cell screening system to define the distribution and activity of specific cellular constituents and processes, using the luminescent probes, the optical imaging system, and the pattern recognition software of the invention. Preferred embodiments of the machine readable storage medium comprise programs consisting of a set of instructions for causing a cell screening system to execute the procedures set forth in FIG. 9, 11, 12, 13, 14 or 15. Another preferred embodiment comprises a program consisting of a set of instructions for causing a cell screening system to execute procedures for detecting the distribution and activity of specific cellular constituents and processes. In most preferred embodiments, the cellular processes include, but are not limited to, nuclear translocation of a protein, cellular morphology, apoptosis, receptor internalization, and protease-induced translocation of a protein.

In a preferred embodiment, the cell screening methods are used to identify compounds that modify the various cellular processes. The cells can be contacted with a test compound, and the effect of the test compound on a particular cellular process can be analyzed. Alternatively, the cells can be contacted with a test compound and a known agent that modifies the particular cellular process, to determine whether the test compound can inhibit or enhance the effect of the known agent. Thus, the methods can be used to identify test compounds that increase or decrease a particular cellular response, as well as to identify test compounds that affects the ability of other agents to increase or decrease a particular cellular response.

In another preferred embodiment, the locations containing cells are analyzed using the above methods at low resolution in a high throughput mode, and only a subset of the locations containing cells are analyzed in a high content mode to obtain luminescent signals from the luminescently labeled reporter molecules in subcellular compartments of the cells being analyzed.

The following examples are intended for purposes of illustration only and should not be construed to limit the scope of the invention, as defined in the claims appended hereto.

The various chemical compounds, reagents, dyes, and antibodies that are referred to in the following Examples are commercially available from such sources as Sigma Chemical (St. Louis, Mo.), Molecular Probes (Eugene, Oreg.), Aldrich Chemical Company (Milwaukee, Wis.), Accurate Chemical Company (Westbury, N.Y.), Jackson Immunolabs, and Clontech (Palo Alto, Calif.).

Example 1

Cytoplasm to Nucleus Translocation Screening a. Transcription Factors

Regulation of transcription of some genes involves activation of a transcription factor in the cytoplasm, resulting in that factor being transported into the nucleus where it can initiate transcription of a particular gene or genes. This change in transcription factor distribution is the basis of a screen for the cell-based screening system to detect compounds that inhibit or induce transcription of a particular gene or group of genes. A general description of the screen is given followed by a specific example.

The distribution of the transcription factor is determined by labeling the nuclei with a DNA specific fluorophore like Hoechst 33423 and the transcription factor with a specific fluorescent antibody. After autofocusing on the Hoechst labeled nuclei, an image of the nuclei is acquired in the cell-based screening system and used to create a mask by one of several optional thresholding methods, as described supra. The morphological descriptors of the regions defined by the mask are compared with the user defined parameters and valid nuclear masks are identified and used with the following method to extract transcription factor distributions. Each valid nuclear mask is eroded to define a slightly smaller nuclear region. The original nuclear mask is then dilated in two steps to define a ring shaped region around the nucleus, which represents a cytoplasmic region. The average antibody fluorescence in each of these two regions is determined, and the difference between these averages is defined as the NucCyt Difference. Two examples of determining nuclear translocation are discussed below and illustrated in FIG. 10A-J. FIG. 10A illustrates an unstimulated cell with its nucleus 200 labeled with a blue fluorophore and a transcription factor in the cytoplasm 201 labeled with a green fluorophore. FIG. 10B illustrates the nuclear mask 202 derived by the cell-based screening system. FIG. 10C illustrates the cytoplasm 203 of the unstimulated cell imaged at a green wavelength. FIG. 10D illustrates the nuclear mask 202 is eroded (reduced) once to define a nuclear sampling region 204 with minimal cytoplasmic distribution. The nucleus boundary 202 is dilated (expanded) several times to form a ring that is 2-3 pixels wide that is used to define the cytoplasmic sampling region 205 for the same cell. FIG. 10E further illustrates a side view which shows the nuclear sampling region 204 and the cytoplasmic sampling region 205. Using these two sampling regions, data on nuclear translocation can be automatically analyzed by the cell-based screening system on a cell by cell basis. FIG. 10F-J illustrates the strategy for determining nuclear translocation in a stimulated cell. FIG. 10F illustrates a stimulated cell with its nucleus 206 labeled with a blue fluorophore and a transcription factor in the cytoplasm 207 labeled with a green fluorophore. The nuclear mask 208 in FIG. 10G is derived by the cell based screening system. FIG. 10H illustrates the cytoplasm 209 of a stimulated cell imaged at a green wavelength. FIG. 10I illustrates the nuclear sampling region 211 and cytoplasmic sampling region 212 of the stimulated cell. FIG. 10J further illustrates a side view which shows the nuclear sampling region 211 and the cytoplasmic sampling region 212.

Figure 16:
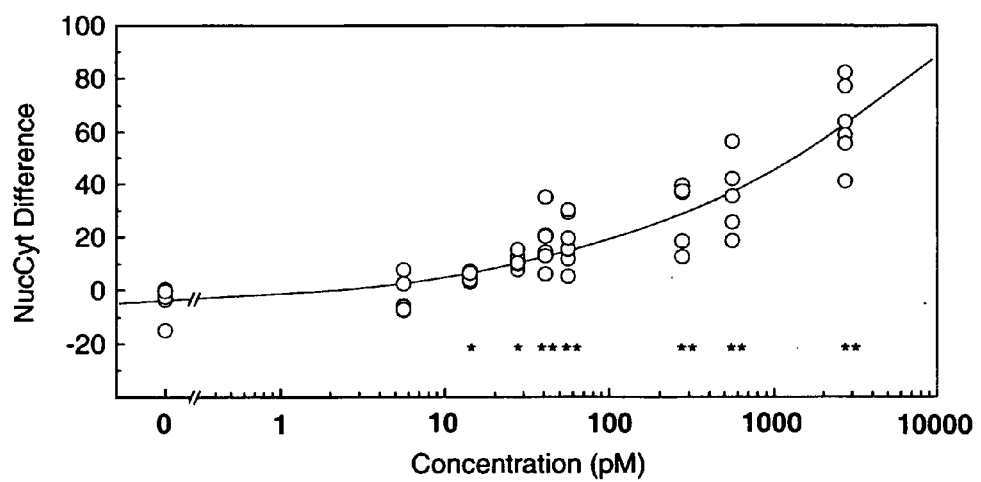
FIG. 16 is an example of data from a known inhibitor of translocation.
Figure 17:
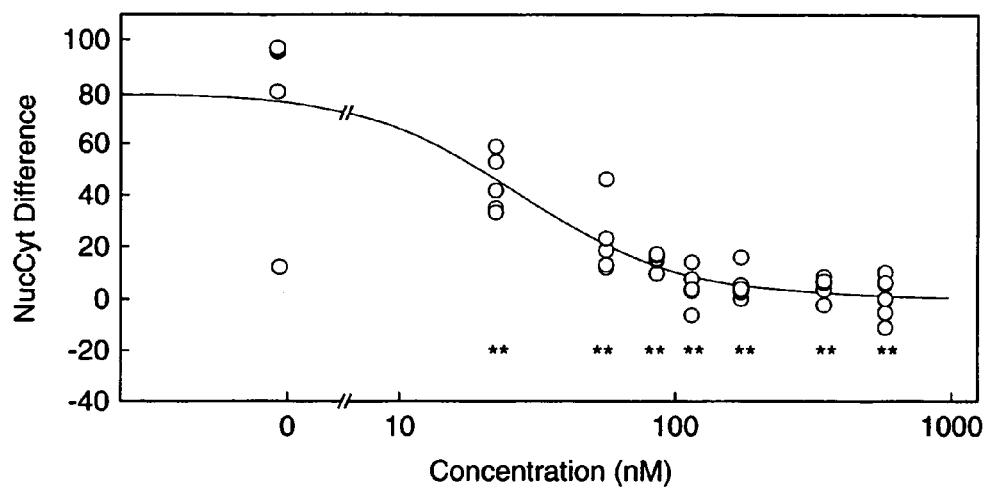
FIG. 17 is an example of data from a known stimulator of translocation.

A specific application of this method has been used to validate this method as a screen. A human cell line was plated in 96 well microtiter plates. Some rows of wells were titrated with IL-1, a known inducer of the NF-KB transcription factor. The cells were then fixed and stained by standard methods with a fluorescein labeled antibody to the transcription factor, and Hoechst 33423. The cell-based screening system was used to acquire and analyze images from this plate and the NucCyt Difference was found to be strongly correlated with the amount of agonist added to the wells as illustrated in FIG. 16. In a second experiment, an antagonist to the receptor for IL-1, IL-1RA was titrated in the presence of IL-1α, progressively inhibiting the translocation induced by IL-1α. The NucCyt Difference was found to strongly correlate with this inhibition of translocation, as illustrated in FIG. 17.

Additional experiments have shown that the NucCyt Difference, as well as the NucCyt ratio, gives consistent results over a wide range of cell densities and reagent concentrations, and can therefore be routinely used to screen compound libraries for specific nuclear translocation activity. Furthermore, the same method can be used with antibodies to other transcription factors, or GFP-transcription factor chimeras, or fluorescently labeled transcription factors introduced into living or fixed cells, to screen for effects on the regulation of transcription factor activity.

Figure 18:
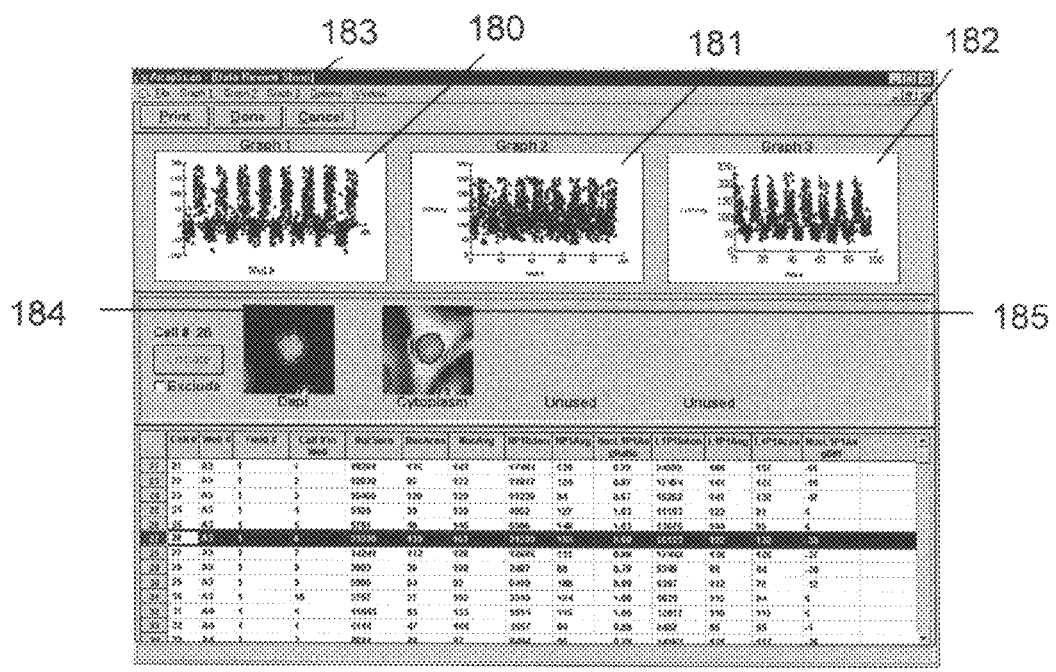
FIG. 18 illustrates data presentation on a graphical display.

FIG. 18 is a representative display on a PC screen of data which was obtained in accordance with Example 1. Graph 1 180 plots the difference between the average antibody fluorescence in the nuclear sampling region and cytoplasmic sampling region, NucCyt Difference verses Well #. Graph 2 181 plots the average fluorescence of the antibody in the nuclear sampling region, NP1 average, versus the Well #. Graph 3 182 plots the average antibody fluorescence in the cytoplasmic sampling region, LIP1 average, versus Well #. The software permits displaying data from each cell. For example, FIG. 18 shows a screen display 183, the nuclear image 184, and the fluorescent antibody image 185 for cell #26.

NucCyt Difference referred to in graph 1 180 of FIG. 18 is the difference between the average cytoplasmic probe (fluorescent reporter molecule) intensity and the average nuclear probe (fluorescent reporter molecule) intensity. NP1 average referred to in graph 2 181 of FIG. 18 is the average of cytoplasmic probe (fluorescent reporter molecule) intensity within the nuclear sampling region. L1P1 average referred to in graph 3 182 of FIG. 18 is the average probe (fluorescent reporter molecule) intensity within the cytoplasmic sampling region.

It will be understood by one of skill in the art that this aspect of the invention can be performed using other transcription factors that translocate from the cytoplasm to the nucleus upon activation. In another specific example, activation of the c-fos transcription factor was assessed by defining its spatial position within cells. Activated c-fos is found only within the nucleus, while inactivated c-fos resides within the cytoplasm.

3T3 cells were plated at 5000-10000 cells per well in a Polyfiltronics 96-well plate. The cells were allowed to attach and grow overnight. The cells were rinsed twice with 100 μl serum-free medium, incubated for 24-30 hours in serum-free MEM culture medium, and then stimulated with platelet derived growth factor (PDGF-BB) (Sigma Chemical Co., St. Louis, Mo.) diluted directly into serum free medium at concentrations ranging from 1-50 ng/ml for an average time of 20 minutes.

Following stimulation, cells were fixed for 20 minutes in 3.7% formaldehyde solution in 1× Hanks buffered saline solution (HBSS). After fixation, the cells were washed with HBSS to remove residual fixative, permeabilized for 90 seconds with 0.5% Triton X-100 solution in HBSS, and washed twice with HBSS to remove residual detergent. The cells were then blocked for 15 minutes with a 0.1% solution of BSA in HBSS, and further washed with HBSS prior to addition of diluted primary antibody solution.

c-Fos rabbit polyclonal antibody (Calbiochem, PC05) was diluted 1:50 in HBSS, and 50 μl of the dilution was applied to each well. Cells were incubated in the presence of primary antibody for one hour at room temperature, and then incubated for one hour at room temperature in a light tight container with goat anti-rabbit secondary antibody conjugated to ALEXA™ 488 (Molecular Probes), diluted 1:500 from a 100 μg/ml stock in HBSS. Hoechst DNA dye (Molecular Probes) was then added at a 1:1000 dilution of the manufacturer's stock solution (10 mg/ml). The cells were then washed with HBSS, and the plate was sealed prior to analysis with the cell screening system of the invention. The data from these experiments demonstrated that the methods of the invention could be used to measure transcriptional activation of c-fos by defining its spatial position within cells.

One of skill in the art will recognize that while the following method is applied to detection of c-fos activation, it can be applied to the analysis of any transcription factor that translocates from the cytoplasm to the nucleus upon activation. Examples of such transcription factors include, but are not limited to fos and jun homologs, NF-KB (nuclear factor kappa from B cells), NFAT (nuclear factor of activated T-lymphocytes), and STATs (signal transducer and activator of transcription) factors (For example, see Strehlow, I., and Schindler, C. 1998. *J. Biol. Chem.* 273:28049-28056; Chow, et al. 1997 *Science.* 278:1638-1641; Ding et al. 1998 *J. Biol. Chem.* 273:28897-28905; Baldwin, 1996. *Annu Rev Immunol.* 14:649-83; Kuo, C. T., and J. M. Leiden. 1999. *Annu Rev Immunol.* 17:149-87; Rao, et al. 1997. *Annu Rev Immunol.* 15:707-47; Masuda, et al. 1998. *Cell Signal.* 10:599-611; Hoey, T., and U. Schindler. 1998. *Curr Opin Genet Dev.* 8:582-7; Liu, et al. 1998. *Curr Opin Immunol.* 10:271-8.)

Thus, in this aspect of the invention, indicator cells are treated with test compounds and the distribution of luminescently labeled transcription factor is measured in space and time using a cell screening system, such as the one disclosed above. The luminescently labeled transcription factor may be expressed by or added to the cells either before, together with, or after contacting the cells with a test compound. For example, the transcription factor may be expressed as a luminescently labeled protein chimera by transfected indicator cells. Alternatively, the luminescently labeled transcription factor may be expressed, isolated, and bulk-loaded into the indicator cells as described above, or the transcription factor may be luminescently labeled after isolation. As a further alternative, the transcription factor is expressed by the indicator cell, which is subsequently contacted with a luminescent label, such as an antibody, that detects the transcription factor.

In a further aspect, kits are provided for analyzing transcription factor activation, comprising an antibody that specifically recognizes a transcription factor of interest, and instructions for using the antibody for carrying out the methods described above. In a preferred embodiment, the transcription factor-specific antibody, or a secondary antibody that detects the transcription factor antibody, is luminescently labeled. In further preferred embodiments, the kit contains cells that express the transcription factor of interest, and/or the kit contains a compound that is known to modify activation of the transcription factor of interest, including but not limited to platelet derived growth factor (PDGF) and serum, which both modify fos activation; and interleukin 1 (IL-1) and tumor necrosis factor (TNF), which both modify NF-KB activation.

In another embodiment, the kit comprises a recombinant expression vector comprising a nucleic acid encoding a transcription factor of interest that translocates from the cytoplasm to the nucleus upon activation, and instructions for using the expression vector to identify compounds that modify transcription factor activation in a cell of interest. Alternatively, the kits contain a purified, luminescently labeled transcription factor. In a preferred embodiment, the transcription factor is expressed as a fusion protein with a luminescent protein, including but not limited to green fluorescent protein, luceriferase, or mutants or fragments thereof. In various preferred embodiments, the kit further contains cells that are transfected with the expression vector, an antibody or fragment that specifically bind to the transcription factor of interest, and/or a compound that is known to modify activation of the transcription factor of interest (as above).

b. Protein Kinases

The cytoplasm to nucleus screening methods can also be used to analyze the activation of any protein kinase that is present in an inactive state in the cytoplasm and is transported to the nucleus upon activation, or that phosphorylates a substrate that translocates from the cytoplasm to the nucleus upon phosphorylation. Examples of appropriate protein kinases include, but are not limited to extracellular signal-regulated protein kinases. (ERKs), c-Jun amino-terminal kinases (JNKs), Fos regulating protein kinases (ERKs), p38 mitogen activated protein kinase (p38MAPK), protein kinase A (PKA), and mitogen activated protein kinase kinases (MAPKKs). (For example, see Hall, et al. 1999. *J Biol. Chem.* 274:376-83; Han, et al. 1995. *Biochim. Biophys. Acta.* 1265: 224-227; Jaaro et al. 1997. *Proc. Natl. Acad. Sci. U.S.A.* 94:3742-3747; Taylor, et al. 1994. *J. Biol. Chem.* 269:308-318; Zhao, Q., and F. S. Lee. 1999. *J Biol. Chem.* 274:8355-8; Paolillo et al. 1999. *J Biol. Chem.* 274:6546-52; Coso et al. 1995. Cell 81:1137-1146; Tibbles, L. A., and J. R. Woodgett. 1999. *Cell Mol Life Sci.* 55:1230-54; Schaeffer, H. J., and M. J. Weber. 1999. *Mol Cell Biol.* 19:2435-44.)

Alternatively, protein kinase activity is assayed by monitoring translocation of a luminescently labeled protein kinase substrate from the cytoplasm to the nucleus after being phosphorylated by the protein kinase of interest. In this embodiment, the substrate is non-phosphorylated and cytoplasmic prior to phosphorylation, and is translocated to the nucleus upon phosphorylation by the protein kinase. There is no requirement that the protein kinase itself translocates from the cytoplasm to the nucleus in this embodiment. Examples of such substrates (and the corresponding protein kinase) include, but are not limited to c-jun (JNK substrate); fos (FRK substrate), and p38 (p38 MAPK substrate).

Thus, in these embodiments, indicator cells are treated with test compounds and the distribution of luminescently labeled protein kinase or protein kinase substrate is measured in space and time using a cell screening system, such as the one disclosed above. The luminescently labeled protein kinase or protein kinase substrate may be expressed by or added to the cells either before, together with, or after contacting the cells with a test compound. For example, the protein kinase or protein kinase substrate may be expressed as a luminescently labeled protein chimera by transfected indicator cells. Alternatively, the luminescently labeled protein kinase or protein kinase substrate may be expressed, isolated, and bulk-loaded into the indicator cells as described above, or the protein kinase or protein kinase substrate may be luminescently labeled after isolation. As a further alternative, the protein kinase or protein kinase substrate is expressed by the indicator cell, which is subsequently contacted with a luminescent label, such as a labeled antibody, that detects the protein kinase or protein kinase substrate.

In a further embodiment, protein kinase activity is assayed by monitoring the phosphorylation state (ie: phosphorylated or not phosphorylated) of a protein kinase substrate. In this embodiment, there is no requirement that either the protein kinase or the protein kinase substrate translocate from the cytoplasm to the nucleus upon activation. In a preferred embodiment, phosphorylation state is monitored by contacting the cells with an antibody that binds only to the phosphorylated form of the protein kinase substrate of interest (For example, as disclosed in U.S. Pat. No. 5,599,681).

In another preferred embodiment, a biosensor of phosphorylation is used. For example, a luminescently labeled protein or fragment thereof can be fused to a protein that has been engineered to contain (a) a phosphorylation site that is recognized by a protein kinase of interest; and (b) a nuclear localization signal that is unmasked by the phosphorylation. Such a biosensor will thus be translocated to the nucleus upon phosphorylation, and its translocation can be used as a measure of protein kinase activation.

In another aspect, kits are provided for analyzing protein kinase activation, comprising a primary antibody that specifically binds to a protein kinase, a protein kinase substrate, or a phosphorylated form of the protein kinase substrate of interest and instructions for using the primary antibody to identify compounds that modify protein kinase activation in a cell of interest. In a preferred embodiment, the primary antibody, or a secondary antibody that detects the primary antibody, is luminescently labeled. In other preferred embodiments, the kit further comprises cells that express the protein kinase of interest, and/or a compound that is known to modify activation of the protein kinase of interest, including but not limited to dibutyryl cAMP (modifies PKA), forskolin (PKA), and anisomycin (p38MAPK).

Alternatively, the kits comprise an expression vector encoding a protein kinase or a protein kinase substrate of interest that translocates from the cytoplasm to the nucleus upon activation and instructions for using the expression vector to identify compounds that modify protein kinase activation in a cell of interest. Alternatively, the kits contain a purified, luminescently labeled protein kinase or protein kinase substrate. In a preferred embodiment, the protein kinase or protein kinase substrate of interest is expressed as a fusion protein with a luminescent protein. In further preferred embodiments, the kit further comprises cells that are transfected with the expression vector, an antibody or fragment thereof that specifically binds to the protein kinase or protein kinase substrate of interest, and/or a compound that is known to modify activation of the protein kinase of interest. (as above)

In another aspect, the present invention comprises a machine readable storage medium comprising a program containing a set of instructions for causing a cell screening system to execute the methods disclosed for analyzing transcription factor or protein kinase activation, wherein the cell screening system comprises an optical system with a stage adapted for holding a plate containing cells, a digital camera, a means for directing fluorescence or luminescence emitted from the cells to the digital camera, and a computer means for receiving and processing the digital data from the digital camera.

Example 2

Automated Screen for Compounds that Modify Cellular Morphology

Changes in cell size are associated with a number of cellular conditions, such as hypertrophy, cell attachment and spreading, differentiation, growth and division, necrotic and programmed cell death, cell motility, morphogenesis, tube formation, and colony formation.

For example, cellular hypertrophy has been associated with a cascade of alterations in gene expression and can be characterized in cell culture by an alteration in cell size, that is clearly visible in adherent cells growing on a coverslip.

Cell size can also be measured to determine the attachment and spreading of adherent cells. Cell spreading is the result of selective binding of cell surface receptors to substrate ligands and subsequent activation of signaling pathways to the cytoskeleton. Cell attachment and spreading to substrate molecules is an important step for the metastasis of cancer cells, leukocyte activation during the inflammatory response, keratinocyte movement during wound healing, and endothelial cell movement during angiogenesis. Compounds that affect these surface receptors, signaling pathways, or the cytoskeleton will affect cell spreading and can be screened by measuring cell size.

Total cellular area can be monitored by labeling the entire cell body or the cell cytoplasm using cytoskeletal markers, cytosolic volume markers, or cell surface markers, in conjunction with a DNA label. Examples of such labels (many available from Molecular Probes (Eugene, Oreg.) and Sigma Chemical Co. (St. Louis, Mo.)) include the following:

| CELL SIZE AND AREA MARKERS |
|---|
| Cytoskeletal Markers |
| ALEXA ™ 488 phalloidin (Molecular Probes. Oregon) Tubulin-green fluorescent protein chimeras Cytokeratin-green fluorescent protein chimeras Antibodies to cytoskeletal proteins Cytosolic Volume Markers |
| Green fluorescent proteins Chloromethylfluorescein diacetate (CMFDA) Calcein green BCECF/AM ester Rhodamine dextran Cell Surface Markers for Lipid, Protein, or Oligosaccharide |
| Dihexadecyl tetramethylindocarbocyanine perchlorate (DiIC16) lipid dyes Triethylammonium propyl dibutylamino styryl pyridinium (FM 4–64, FM 1–43) lipid dyes MITOTRACKER ™ Green FM Lectins to oligosaccharides such as fluorescein concanavalin A or wheat germ agglutinin SYPRO ™ Red non-specific protein markers Antibodies to various surface proteins such as epidermal growth factor Biotin labeling of surface proteins followed by fluorescent strepavidin labeleing |

Protocols for cell staining with these various agents are well known to those skilled in the art. Cells are stained live or after fixation and the cell area can be measured. For example, live cells stained with DiIC16 have homogeneously labeled plasma membranes, and the projected cross-sectional area of the cell is uniformly discriminated from background by fluorescence intensity of the dye. Live cells stained with cytosolic stains such as CMFDA produce a fluorescence intensity that is proportional to cell thickness. Although cell labeling is dimmer in thin regions of the cell, total cell area can be discriminated from background. Fixed cells can be stained with cytoskeletal markers such as ALEXA™ 488 phalloidin that label polymerized actin. Phalloidin does not homogeneously stain the cytoplasm, but still permits discrimination of the total cell area from background.

Cellular Hypertrophy

A screen to analyze cellular hypertrophy is implemented using the following strategy. Primary rat myocytes can be cultured in 96 well plates, treated with various compounds and then fixed and labeled with a fluorescent marker for the cell membrane or cytoplasm, or cytoskeleton, such as an antibody to a cell surface marker or a fluorescent marker for the cytoskeleton like rhodamine-phalloidin, in combination with a DNA label like Hoechst.

After focusing on the Hoechst labeled nuclei, two images are acquired, one of the Hoechst labeled nuclei and one of the fluorescent cytoplasm image. The nuclei are identified by thresholding to create a mask and then comparing the morphological descriptors of the mask with a set of user defined descriptor values. Each non-nucleus image (or "cytoplasmic image") is then processed separately. The original cytoplasm image can be thresholded, creating a cytoplasmic mask image. Local regions containing cells are defined around the nuclei. The limits of the cells in those regions are then defined by a local dynamic threshold operation on the same region in the fluorescent antibody image. A sequence of erosions and dilations is used to separate slightly touching cells and a second set of morphological descriptors is used to identify single cells. The area of the individual cells is tabulated in order to define the distribution of cell sizes for comparison with size data from normal and hypertrophic cells.

Responses from entire 96-well plates (measured as average cytoplasmic area/cell) were analyzed by the above methods, and the results demonstrated that the assay will perform the same on a well-to-well, plate-to-plate, and day-to-day basis (below a 15% cov for maximum signal). The data showed very good correlation for each day, and that there was no variability due to well position in the plate.

The following totals can be computed for the field. The aggregate whole nucleus area is the number of nonzero pixels in the nuclear mask. The average whole nucleus area is the aggregate whole nucleus area divided by the total number of nuclei. For each cytoplasm image several values can be computed. These are the total cytoplasmic area, which is the count of nonzero pixels in the cytoplasmic mask. The aggregate cytoplasm intensity is the sum of the intensities of all pixels in the cytoplasmic mask. The cytoplasmic area per nucleus is the total cytoplasmic area divided by the total nucleus count. The cytoplasmic intensity per nucleus is the aggregate cytoplasm intensity divided by the total nucleus count. The average cytoplasm intensity is the aggregate cytoplasm intensity divided by the cytoplasm area. The cytoplasm nucleus ratio is the total cytoplasm area divided by the total nucleus area.

Additionally, one or more fluorescent antibodies to other cellular proteins, such as the major muscle proteins actin or myosin, can be included. Images of these additional labeled proteins can be acquired and stored with the above images, for later review, to identify anomalies in the distribution and morphology of these proteins in hypertrophic cells. This example of a multi-parametric screen allows for simultaneous analysis of cellular hypertrophy and changes in actin or myosin distribution.

One of skill in the art will recognize that while the example analyzes myocyte hypertrophy, the methods can be applied to analyzing hypertrophy, or general morphological changes in any cell type.

Cell Morphology Assays for Prostate Carcinoma

Cell spreading is a measure of the response of cell surface receptors to substrate attachment ligands. Spreading is proportional to the ligand concentration or to the concentration of compounds that reduce receptor-ligand function. One example of selective cell-substrate attachment is prostate carcinoma cell adhesion to the extracellular matrix protein collagen. Prostate carcinoma cells metastasize to bone via selective adhesion to collagen.

Compounds that interfere with metastasis of prostate carcinoma cells were screened as follows. PC3 human prostate carcinoma cells were cultured in media with appropriate stimulants and are passaged to collagen coated 96 well plates. Ligand concentration can be varied or inhibitors of cell spreading can be added to the wells. Examples of compounds that can affect spreading are receptor antagonists such as integrin- or proteoglycan-blocking antibodies, signaling inhibitors including phosphatidyl inositol-3 kinase inhibitors, and cytoskeletal inhibitors such as cytochalasin D. After two hours, cells were fixed and stained with ALEXA™ 488 phalloidin (Molecular Probes) and Hoechst 33342 as per the protocol for cellular hypertrophy. The size of cells under these various conditions, as measured by cytoplasmic staining, can be distinguished above background levels. The number of cells per field is determined by measuring the number of nuclei stained with the Hoechst DNA dye. The area per cell is found by dividing the cytoplasmic area (phalloidin image) by the cell number (Hoechst image). The size of cells is proportional to the ligand-receptor function. Since the area is determined by ligand concentration and by the resultant function of the cell, drug efficacy, as well as drug potency, can be determined by this cell-based assay. Other measurements can be made as discussed above for cellular hypertrophy.

The methods for analyzing cellular morphology can be used in a combined high throughput-high content screen. In one example, the high throughput mode scans the whole well for an increase in fluorescent phalloidin intensity. A threshold is set above which both nuclei (Hoechst) and cells (phalloidin) are measured in a high content mode. In another example, an environmental biosensor (examples include, but are not limited to, those biosensors that are sensitive to calcium and pH changes) is added to the cells, and the cells are contacted with a compound. The cells are scanned in a high throughput mode, and those wells that exceed a pre-determined threshold for luminescence of the biosensor are scanned in a high content mode.

In a further aspect, kits are provided for analyzing cellular morphology, comprising a luminescent compound that can be used to specifically label the cell cytoplasm, membrane, or cytoskeleton (such as those described above), and instructions for using the luminescent compound to identify test stimuli that induce or inhibit changes in cellular morphology according to the above methods. In a preferred embodiment, the kit further comprises a luminescent marker for cell nuclei. In a further preferred embodiment, the kit comprises at least one compound that is known to modify cellular morphology, including, but not limited to integrin- or proteoglycan-blocking antibodies, signaling inhibitors including phosphatidyl inositol-3 kinase inhibitors, and cytoskeletal inhibitors such as cytochalasin D.

In another aspect, the present invention comprises a machine readable storage medium comprising a program containing a set of instructions for causing a cell screening system to execute the disclosed methods for analyzing cellular morphology, wherein the cell screening system comprises an optical system with a stage adapted for holding a plate containing cells, a digital camera, a means for directing fluorescence or luminescence emitted from the cells to the digital camera, and a computer means for receiving and processing the digital data from the digital camera.

Example 3

Dual Mode High Throughput and High-Content Screen

The following example is a screen for activation of a G-protein coupled receptor (GPCR) as detected by the translocation of the GPCR from the plasma membrane to a proximal nuclear location. This example illustrates how a high throughput screen can be coupled with a high-content screen in the dual mode System for Cell Based Screening.

G-protein coupled receptors are a large class of 7 transmembrane domain cell surface receptors. Ligands for these receptors stimulate a cascade of secondary signals in the cell, which may include, but are not limited to, $Ca^{++}$ transients, cyclic AMP production, inositol triphosphate ($IP_3$) production and phosphorylation. Each of these signals are rapid, occurring in a matter of seconds to minutes, but are also generic. For example, many different GPCRs produce a secondary $Ca^{++}$ signal when activated. Stimulation of a GPCR also results in the transport of that GPCR from the cell surface membrane to an internal, proximal nuclear compartment. This internalization is a much more receptor-specific indicator of activation of a particular receptor than are the secondary signals described above.

Figure 19:
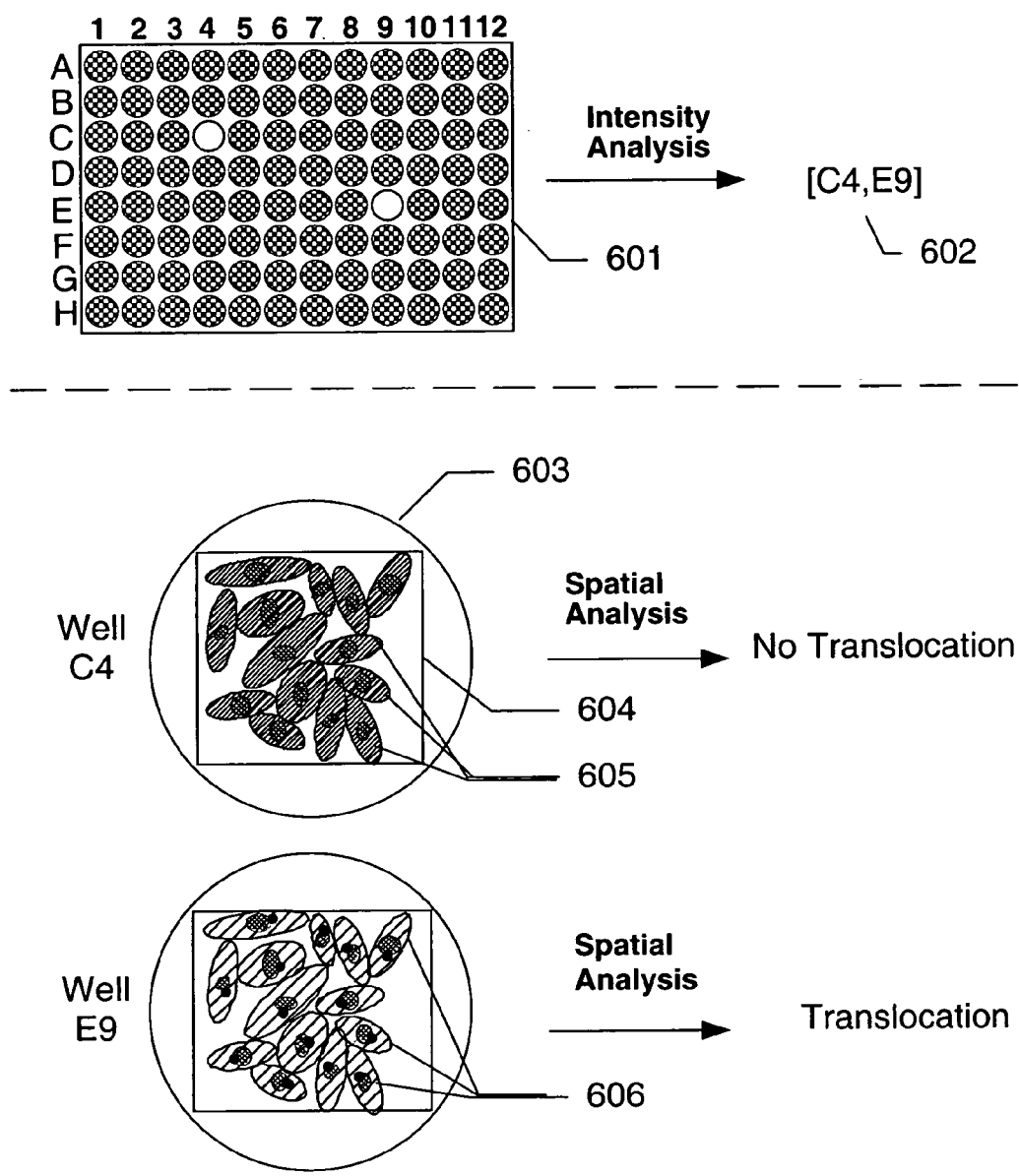
FIG. 19 is an illustration of the data from the High Throughput mode of the System for Cell Based Screening, an example of the data passed to the High Content mode, the data acquired in the high content mode, and the results of the analysis of that data.

FIG. 19 illustrates a dual mode screen for activation of a GPCR. Cells carrying a stable chimera of the GPCR with a blue fluorescent protein (BFP) would be loaded with the acetoxymethylester form of Fluo-3, a cell permeable calcium indicator (green fluorescence) that is trapped in living cells by the hydrolysis of the esters. They would then be deposited into the wells of a microtiter plate 601. The wells would then be treated with an array of test compounds using a fluid delivery system, and a short sequence of Fluo-3 images of the whole microtiter plate would be acquired and analyzed for wells exhibiting a calcium response (i.e., high throughput mode). The images would appear like the illustration of the microtiter plate 601 in FIG. 19. A small number of wells, such as wells C4 and E9 in the illustration, would fluoresce more brightly due to the $Ca^{++}$ released upon stimulation of the receptors. The locations of wells containing compounds that induced a response 602, would then be transferred to the HCS program and the optics switched for detailed cell by cell analysis of the blue fluorescence for evidence of GPCR translocation to the perinuclear region. The bottom of FIG. 19 illustrates the two possible outcomes of the analysis of the high resolution cell data. The camera images a sub-region 604 of the well area 603, producing images of the fluorescent cells 605. In well C4, the uniform distribution of the fluorescence in the cells indicates that the receptor has not internalized, implying that the $Ca^{++}$ response seen was the result of the stimulation of some other signalling system in the cell. The cells in well E9 606 on the other hand, clearly indicate a concentration of the receptor in the perinuclear region clearly indicating the full activation of the receptor. Because only a few hit wells have to be analyzed with high resolution, the overall throughput of the dual mode system can be quite high, comparable to the high throughput system alone.

Example 4

Kinetic High Content Screen

The following is an example of a screen to measure the kinetics of internalization of a receptor. As described above, the stimulation of a GPCR, results in the internalization of the receptor, with a time course of about 15 min. Simply detecting the endpoint as internalized or not, may not be sufficient for defining the potency of a compound as a GPCR agonist or antagonist. However, 3 time points at 5 min intervals would provide information not only about potency during the time course of measurement, but would also allow extrapolation of the data to much longer time periods. To perform this assay, the sub-region would be defined as two rows, the sampling interval as 5 minutes and the total number of time points 3. The system would then start by scanning two rows, and then adding reagent to the two rows, establishing the time=0 reference. After reagent addition, the system would again scan the two row sub-region acquiring the first time point data. Since this process would take about 250 seconds, including scanning back to the beginning of the sub-region, the system would wait 50 seconds to begin acquisition of the second time point. Two more cycles would produce the three time points and the system would move on to the second 2 row sub-region. The final two 2-row sub-regions would be scanned to finish all the wells on the plate, resulting in four time points for each well over the whole plate. Although the time points for the wells would be offset slightly relative to time=0, the spacing of the time points would be very close to the required 5 minutes, and the actual acquisition times and results recorded with much greater precision than in a fixed-cell screen.

Example 5

High-Content Screen of Human Glucocorticoid Receptor Translocation

One class of HCS involves the drug-induced dynamic redistribution of intracellular constituents. The human glucocorticoid receptor (hGR), a single "sensor" in the complex environmental response machinery of the cell, binds steroid molecules that have diffused into the cell. The ligand-receptor complex translocates to the nucleus where transcriptional activation occurs (Htun et al., *Proc. Natl. Acad. Sci.* 93:4845, 1996).

In general, hormone receptors are excellent drug targets because their activity lies at the apex of key intracellular signaling pathways. Therefore, a high-content screen of hGR translocation has distinct advantage over in vitro ligand-receptor binding assays. The availability of up to two more channels of fluorescence in the cell screening system of the present invention permits the screen to contain two additional parameters in parallel, such as other receptors, other distinct targets or other cellular processes.

Plasmid construct. A eukaryotic expression plasmid containing a coding sequence for a green fluorescent protein—human glucocorticoid receptor (GFP-hGR) chimera was prepared using GFP mutants (Palm et al., *Nat. Struct. Biol.* 4:361 (1997). The construct was used to transfect a human cervical carcinoma cell line (HeLa).

Cell preparation and transfection. HeLa cells (ATCC CCL-2) were trypsinized and plated using DMEM containing 5% charcoal/dextran-treated fetal bovine serum (FBS) (HyClone) and 1% penicillin-streptomycin (C-DMEM) 12-24 hours prior to transfection and incubated at 37° C. and 5% $CO_2$. Transfections were performed by calcium phosphate co-precipitation (Graham and Van der Eb, *Virology* 52:456, 1973; Sambrook et al., (1989). *Molecular Cloning: A Laboratory Manual*, Second ed. Cold Spring Harbor Laboratory Press, Cold Spring Harbor, 1989) or with Lipofectamine (Life Technologies, Gaithersburg, Md.). For the calcium phosphate transfections, the medium was replaced, prior to transfection, with DMEM containing 5% charcoal/dextran-treated FBS. Cells were incubated with the calcium phosphate-DNA precipitate for 4-5 hours at 37° C. and 5% $CO_2$, washed 3-4 times with DMEM to remove the precipitate, followed by the addition of C-DMEM.

Lipofectamine transfections were performed in serum-free DMEM without antibiotics according to the manufacturer's instructions (Life Technologies, Gaithersburg, Md.). Following a 2-3 hour incubation with the DNA-liposome complexes, the medium was removed and replaced with C-DMEM. All transfected cells in 96-well microtiter plates were incubated at 33° C. and 5% $CO_2$ for 24-48 hours prior to drug treatment. Experiments were performed with the receptor expressed transiently in HeLa cells.

Dexamethasone induction of GFP-hGR translocation. To obtain receptor-ligand translocation kinetic data, nuclei of transfected cells were first labeled with 5 µg/ml Hoechst 33342 (Molecular Probes) in C-DMEM for 20 minutes at 33° C. and 5% $CO_2$. Cells were washed once in Hank's Balanced Salt Solution (HBSS) followed by the addition of 100 nM dexamethasone in HBSS with 1% charcoal/dextran-treated FBS. To obtain fixed time point dexamethasone titration data, transfected HeLa cells were first washed with DMEM and then incubated at 33° C. and 5% $CO_2$ for 1 h in the presence of 0-1000 nM dexamethasone in DMEM containing 1% charcoal/dextran-treated FBS. Cells were analyzed live or they were rinsed with HBSS, fixed for 15 min with 3.7% formaldehyde in HBSS, stained with Hoechst 33342, and washed before analysis. The intracellular GFP-hGR fluorescence signal was not diminished by this fixation procedure.

Image acquisition and analysis. Kinetic data were collected by acquiring fluorescence image pairs (GFP-hGR and Hoechst 33342-labeled nuclei) from fields of living cells at 1 min intervals for 30 min after the addition of dexamethasone. Likewise, image pairs were obtained from each well of the fixed time point screening plates 1 h after the addition of dexamethasone. In both cases, the image pairs obtained at each time point were used to define nuclear and cytoplasmic regions in each cell. Translocation of GFP-hGR was calculated by dividing the integrated fluorescence intensity of GFP-hGR in the nucleus by the integrated fluorescence intensity of the chimera in the cytoplasm or as a nuclear-cytoplasmic difference of GFP fluorescence. In the fixed time point screen this translocation ratio was calculated from data obtained from at least 200 cells at each concentration of dexamethasone tested. Drug-induced translocation of GFP-hGR from the cytoplasm to the nucleus was therefore correlated with an increase in the translocation ratio.

Figures 20, 20A, 20B:
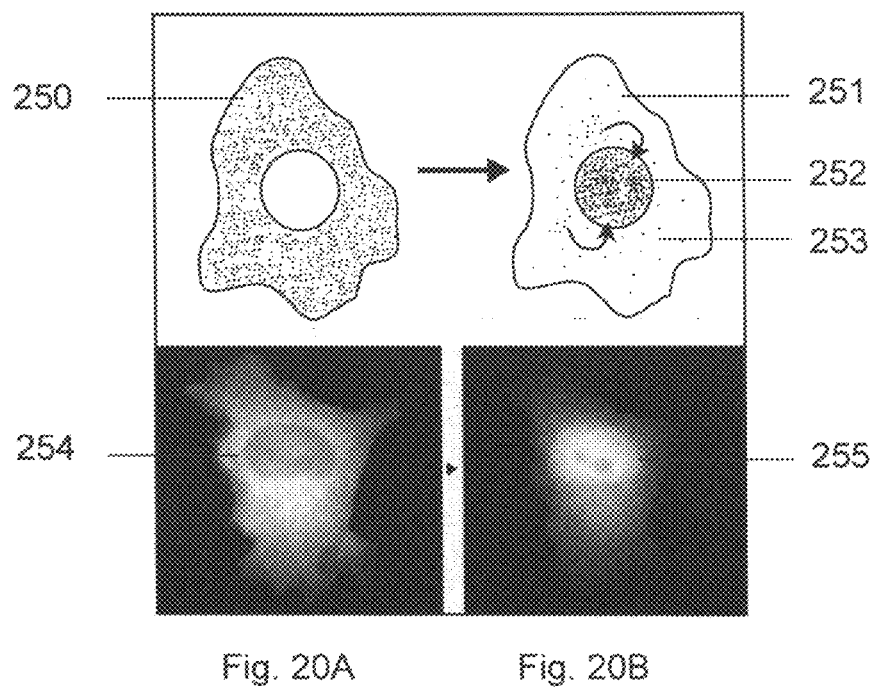
FIG. 20 shows the measurement of a drug-induced cytoplasm to nuclear translocation.

Results. FIG. 20 schematically displays the drug-induced cytoplasm 253 to nucleus 252 translocation of the human glucocorticoid receptor. The upper pair of schematic diagrams depicts the localization of GFP-hGR within the cell before 250 (A) and after 251 (B) stimulation with dexamethasone. Under these experimental conditions, the drug induces a large portion of the cytoplasmic GFP-hGR to translocate into the nucleus. This redistribution is quantified by determining the integrated intensities ratio of the cytoplasmic and nuclear fluorescence in treated 255 and untreated 254 cells. The lower pair of fluorescence micrographs show the dynamic redistribution of GFP-hGR in a single cell, before 254 and after 255 treatment. The HCS is performed on wells containing hundreds to thousands of transfected cells and the translocation is quantified for each cell in the field exhibiting GFP fluorescence. Although the use of a stably transfected cell line would yield the most consistently labeled cells, the heterogeneous levels of GFP-hGR expression induced by transient transfection did not interfere with analysis by the cell screening system of the present invention.

Figure 21:
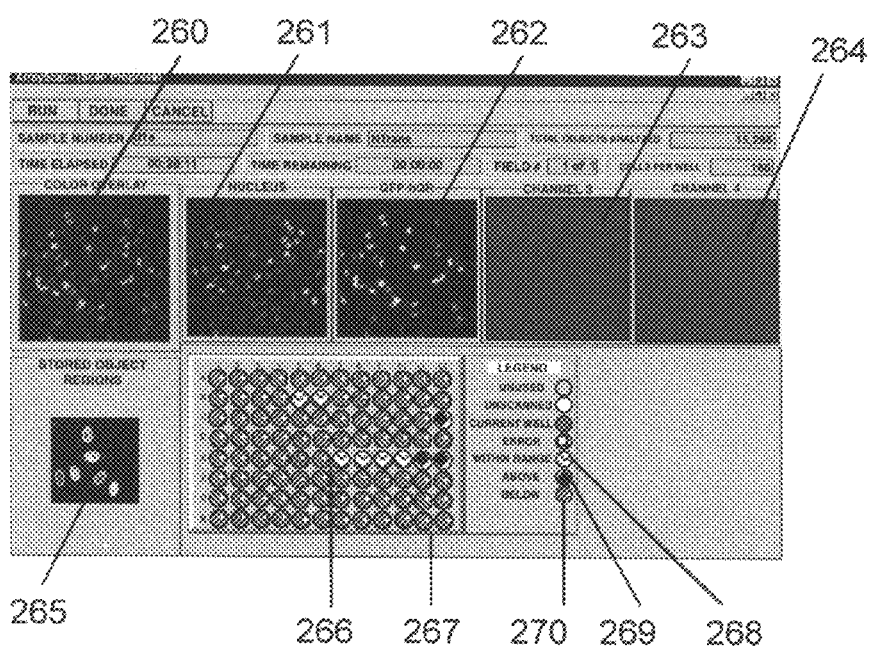
FIG. 21 illustrates a graphical user interface of the measurement shown in FIG. 20.

To execute the screen, the cell screening system scans each well of the plate, images a population of cells in each, and analyzes cells individually. Here, two channels of fluorescence are used to define the cytoplasmic and nuclear distribution of the GFP-hGR within each cell. Depicted in FIG. 21 is the graphical user interface of the cell screening system near the end of a GFP-hGR screen. The user interface depicts the parallel data collection and analysis capability of the system. The windows labeled "Nucleus" 261 and "GFP-hGR" 262 show the pair of fluorescence images being obtained and analyzed in a single field. The window labeled "Color Overlay" 260 is formed by pseudocoloring the above images and merging them so the user can immediately identify cellular changes. Within the "Stored Object Regions" window 265, an image containing each analyzed cell and its neighbors is presented as it is archived. Furthermore, as the HCS data are being collected, they are analyzed, in this case for GFP-hGR translocation, and translated into an immediate "hit" response. The 96 well plate depicted in the lower window of the screen 267 shows which wells have met a set of user-defined screening criteria For example, a white-colored well 269 indicates that the drug-induced translocation has exceeded a predetermined threshold value of 50%. On the other hand, a black-colored well 270 indicates that the drug being tested induced less than 10% translocation. Gray-colored wells 268 indicate "hits" where the translocation value fell between 10% and 50%. Row "E" on the 96 well plate being analyzed 266 shows a titration with a drug known to activate GFP-hGR translocation, dexamethasone. This example screen used only two fluorescence channels. Two additional channels (Channels 3 263 and 4 264) are available for parallel analysis of other specific targets, cell processes, or cytotoxicity to create multiple parameter screens.

Figure 22:
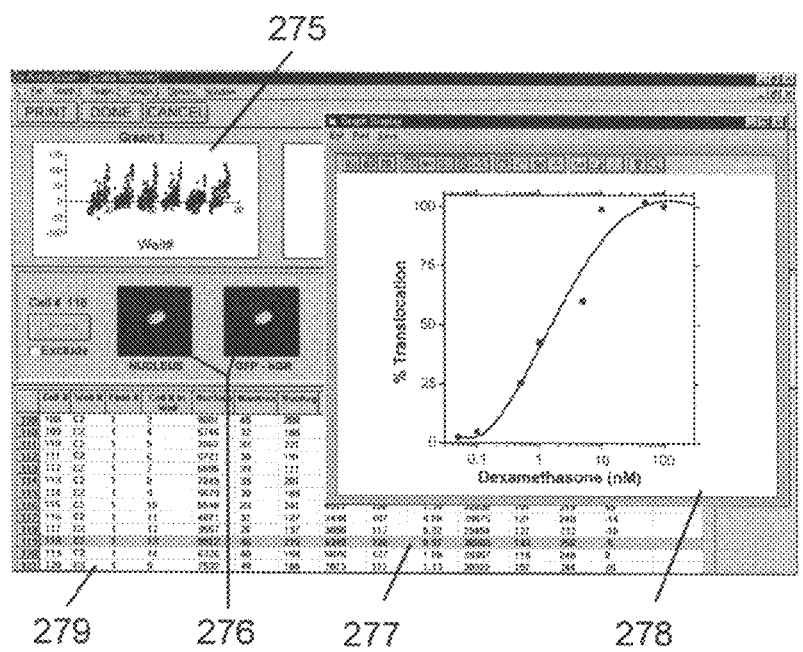
FIG. 22 illustrates a graphical user interface, with data presentation, of the measurement shown in FIG. 20.

There is a link between the image database and the information database that is a powerful tool during the validation process of new screens. At the completion of a screen, the user has total access to image and calculated data (FIG. 22). The comprehensive data analysis package of the cell screening system allows the user to examine HCS data at multiple levels. Images 276 and detailed data in a spread sheet 279 for individual cells can be viewed separately, or summary data can be plotted. For example, the calculated results of a single parameter for each cell in a 96 well plate are shown in the panel labeled Graph 1 275. By selecting a single point in the graph, the user can display the entire data set for a particular cell that is recalled from an existing database. Shown here are the image pair 276 and detailed fluorescence and morphometric data from a single cell (Cell #118, gray line 277). The large graphical insert 278 shows the results of dexamethasone concentration on the translocation of GFP-hGR. Each point is the average of data from at least 200 cells. The calculated $EC_{50}$ for dexamethasone in this assay is 2 nM.

Figure 23:
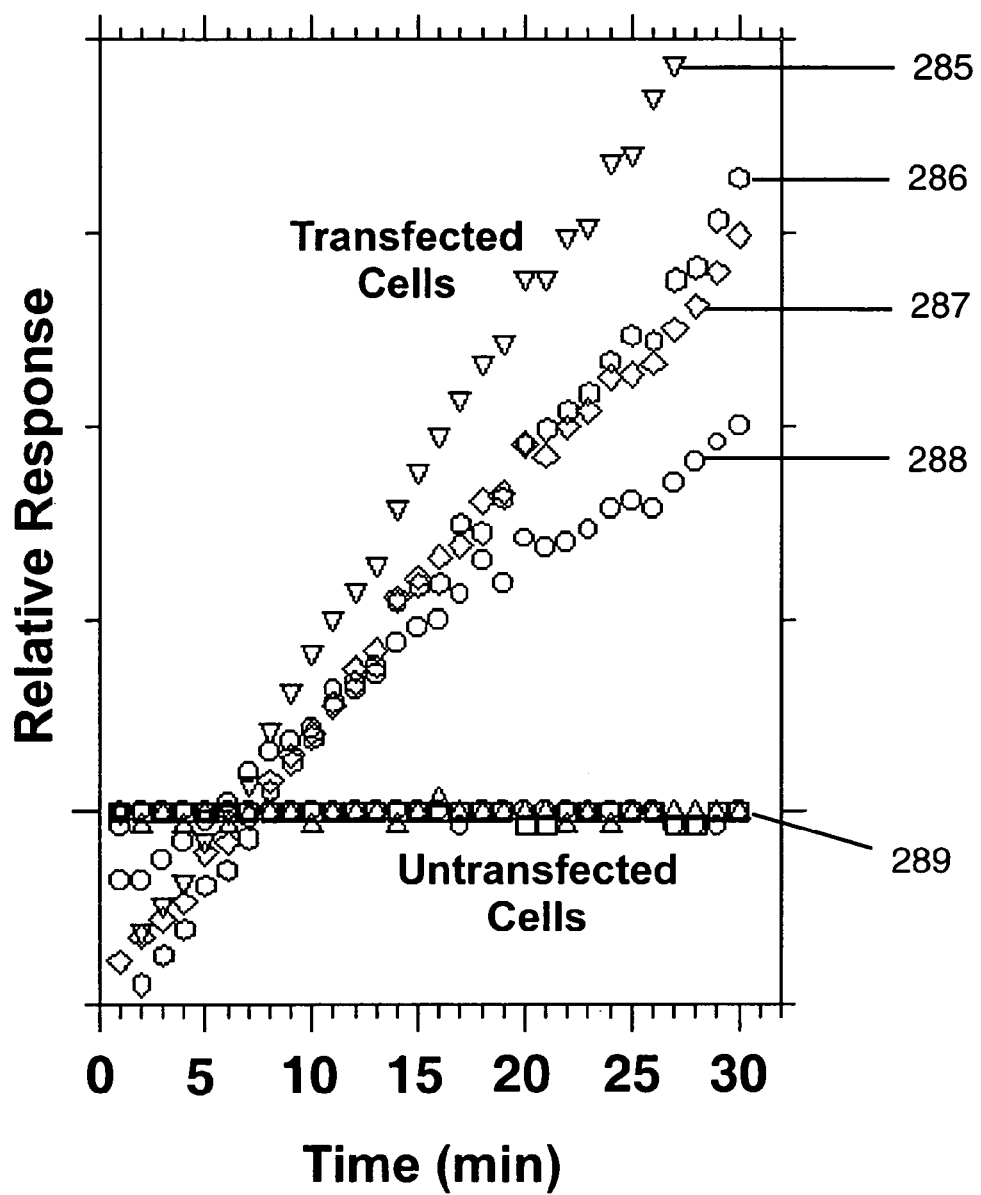
FIG. 23 is a graph representing the kinetic data obtained from the measurements depicted in FIG. 20.

A powerful aspect of HCS with the cell screening system is the capability of kinetic measurements using multicolor fluorescence and morphometric parameters in living cells. Temporal and spatial measurements can be made on single cells within a population of cells in a field. FIG. 23 shows kinetic data for the dexamethasone-induced translocation of GFP-hGR in several cells within a single field. Human HeLa cells transfected with GFP-hGR were treated with 100 nM dexamethasone and the translocation of GFP-hGR was measured over time in a population of single cells. The graph shows the response of transfected cells 285, 286, 287, and 288 and non-transfected cells 289. These data also illustrate the ability to analyze cells with different expression levels.

Example 6

High-Content Screen of Drug-Induced Apoptosis

Apoptosis is a complex cellular program that involves myriad molecular events and pathways. To understand the mechanisms of drug action on this process, it is essential to measure as many of these events within cells as possible with temporal and spatial resolution. Therefore, an apoptosis screen that requires little cell sample preparation yet provides an automated readout of several apoptosis-related parameters would be ideal. A cell-based assay designed for the cell screening system has been used to simultaneously quantify several of the morphological, organellar, and macromolecular hallmarks of paclitaxel-induced apoptosis.

Cell preparation. The cells chosen for this study were mouse connective tissue fibroblasts (L-929; ATCC CCL-1) and a highly invasive glioblastoma cell line (SNB-19; ATCC CRL-2219) (Welch et al., In Vitro Cell. Dev. Biol. 31:610, 1995). The day before treatment with an apoptosis inducing drug, 3500 cells were placed into each well of a 96-well plate and incubated overnight at 37° C. in a humidified 5% $CO_2$ atmosphere. The following day, the culture medium was removed from each well and replaced with fresh medium containing various concentrations of paclitaxel (0-50 µM) from a 20 mM stock made in DMSO. The maximal concentration of DMSO used in these experiments was 0.25%. The cells were then incubated for 26 h as above. At the end of the paclitaxel treatment period, each well received fresh medium containing 750 nM MITOTRACKER® Red (Molecular Probes; Eugene, Oreg.) and 3 µg/ml Hoechst 33342 DNA-binding dye (Molecular Probes) and was incubated as above for 20 min. Each well on the plate was then washed with HESS and fixed with 3.7% formaldehyde in HBSS for 15 min at room temperature. The formaldehyde was washed out with HBSS and the cells were permeabilized for 90 s with 0.5% (v/v) Triton X-100, washed with HBSS, incubated with 2 U ml$^{-1}$ BODIPY® FL phallacidin (Molecular Probes) for 30 min, and washed with HESS. The wells on the plate were then filled with 200 µl HBSS, sealed, and the plate stored at 4° C. if necessary. The fluorescence signals from plates stored this way were stable for at least two weeks after preparation. As in the nuclear translocation assay, fluorescence reagents can be designed to convert this assay into a live cell high-content screen.

Image acquisition and analysis on the ArrayScan System. The fluorescence intensity of intracellular MITOTRACKER® Red, Hoechst 33342, and BODIPY® FL phallacidin was measured with the cell screening system as described supra. Morphometric data from each pair of images obtained from each well was also obtained to detect each object in the image field (e.g., cells and nuclei), and to calculate its size, shape, and integrated intensity.

Calculations and output. A total of 50-250 cells were measured per image field. For each field of cells, the following calculations were performed: (1) The average nuclear area (µm$^2$) was calculated by dividing the total nuclear area in a field by the number of nuclei detected. (2) The average nuclear perimeter (µm) was calculated by dividing the sum of the perimeters of all nuclei in a field by the number of nuclei detected in that field. Highly convoluted apoptotic nuclei had the largest nuclear perimeter values. (3) The average nuclear brightness was calculated by dividing the integrated intensity of the entire field of nuclei by the number of nuclei in that field. An increase in nuclear brightness was correlated with increased DNA content. (4) The average cellular brightness was calculated by dividing the integrated intensity of an entire field of cells stained with MITOTRACKER® dye by the number of nuclei in that field. Because the amount of MITOTRACKER® dye that accumulates within the mitochondria is proportional to the mitochondrial potential, an increase in the average cell brightness is consistent with an increase in mitochondrial potential. (5) The average cellular brightness was also calculated by dividing the integrated intensity of an entire field of cells stained with BODIPY® FL phallacidin dye by the number of nuclei in that field. Because the phallotoxins bind with high affinity to the polymerized form of actin, the amount of BODIPY® FL phallacidin dye that accumulates within the cell is proportional to actin polymerization state. An increase in the average cell brightness is consistent with an increase in actin polymerization.

Figure 24:
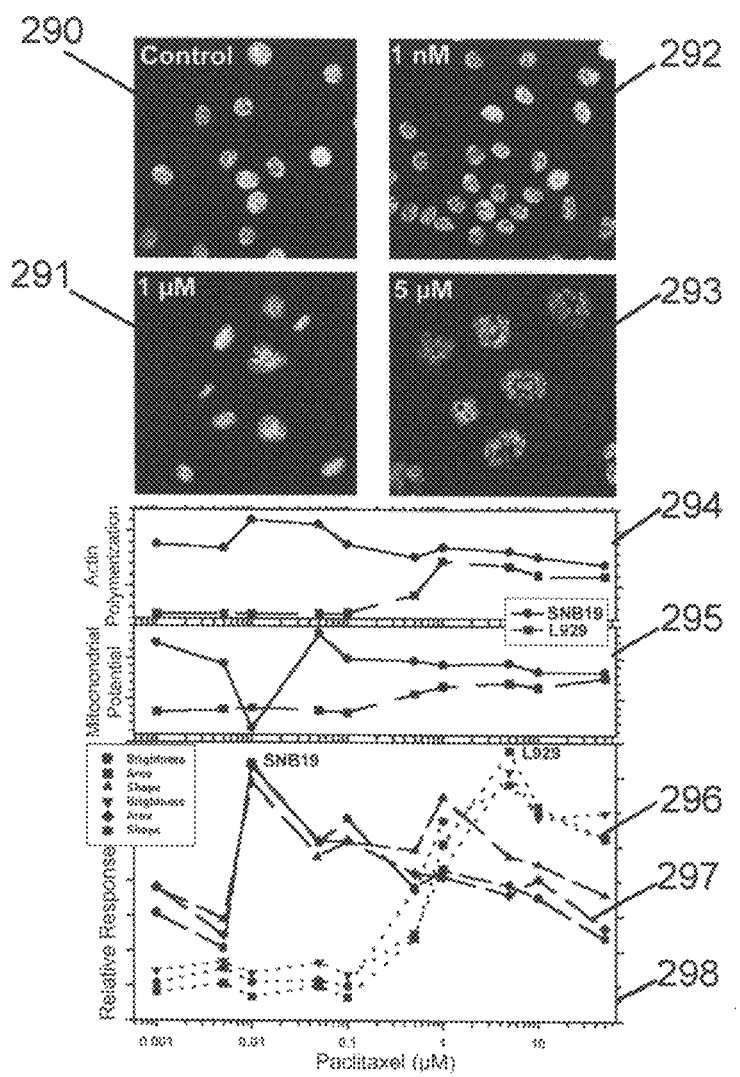
FIG. 24 details a high-content screen of drug-induced apoptosis.

Results. FIG. 24 (top panels) shows the changes paclitaxel induced in the nuclear morphology of L-929 cells. Increasing amounts of paclitaxel caused nuclei to enlarge and fragment 293, a hallmark of apoptosis. Quantitative analysis of these and other images obtained by the cell screening system is presented in the same figure. Each parameter measured showed that the L-929 cells 296 were less sensitive to low concentrations of paclitaxel than were SNB-19 cells 297. At higher concentrations though, the L-929 cells showed a response for each parameter measured. The multiparameter approach of this assay is useful in dissecting the mechanisms of drug action. For example, the area, brightness, and fragmentation of the nucleus 298 and actin polymerization values 294 reached a maximum value when SNB-19 cells were treated with 10 nM paclitaxel (FIG. 24; top and bottom graphs). However, mitochondrial potential 295 was minimal at the same concentration of paclitaxel (FIG. 24; middle graph). The fact that all the parameters measured approached control levels at increasing paclitaxel concentrations (>10 nM) suggests that SNB-19 cells have low affinity drug metabolic or clearance pathways that are compensatory at sufficiently high levels of the drug. Contrasting the drug sensitivity of SNB-19 cells 297, L-929 showed a different response to paclitaxel 296. These fibroblastic cells showed a maximal response in many parameters at 5 µM paclitaxel, a 500-fold higher dose than SNB-19 cells. Furthermore, the L-929 cells did not show a sharp decrease in mitochondrial potential 295 at any of the paclitaxel concentrations tested. This result is consistent with the presence of unique apoptosis pathways between a normal and cancer cell line. Therefore, these results indicate that a relatively simple fluorescence labeling protocol can be coupled with the cell screening system of the present invention to produce a high-content screen of key events involved in programmed cell death.

Example 7

Protease Induced Translocation of a Signaling Enzyme Containing a Disease-Associated Sequence from Cytoplasm to Nucleus Plasmid construct. A eukaryotic expression plasmid containing a coding sequence for a green fluorescent protein—caspase (Cohen (1997), *Biochemical J.* 326:1-16; Liang et al. (1997), *J. of Molec. Biol.* 274:291-302) chimera is prepared using GFP mutants. The construct is used to transfect eukaryotic cells.

Cell preparation and transfection. Cells are trypsinized and plated 24 h prior to transfection and incubated at 37° C. and 5% $CO_2$. Transfections are performed by methods including, but not limited to calcium phosphate coprecipitation or lipofection. Cells are incubated with the calcium phosphate-DNA precipitate for 4-5 hours at 37° C. and 5% $CO_2$, washed 3-4 times with DMEM to remove the precipitate, followed by the addition of C-DMEM. Lipofectamine transfections are performed in serum-free DMEM without antibiotics according to the manufacturer's instructions. Following a 2-3 hour incubation with the DNA-liposome complexes, the medium is removed and replaced with C-DMEM Apoptotic induction of Caspase-GFP translocation. To obtain Caspase-GFP translocation kinetic data, nuclei of transfected cells are first labeled with 5 µg/ml Hoechst 33342 (Molecular Probes) in C-DMEM for 20 minutes at 37° C. and 5% $CO_2$. Cells are washed once in Hank's Balanced Salt Solution (HBSS) followed by the addition of compounds that induce apoptosis. These compounds include, but are not limited to paclitaxel, staurosporine, ceramide, and tumor necrosis factor. To obtain fixed time point titration data, transfected cells are first washed with DMEM and then incubated at 37° C. and 5% $CO_2$ for 1 h in the presence of 0-1000 nM compound in DMEM. Cells are analyzed live or they are rinsed with HBSS, fixed for 15 min with 3.7% formaldehyde in HBSS, stained with Hoechst 33342, and washed before analysis.

Image acquisition and analysis. Kinetic data are collected by acquiring fluorescence image pairs (Caspase-GFP and Hoechst 33342-labeled nuclei) from fields of living cells at 1 min intervals for 30 min after the addition of compound. Likewise, image pairs are obtained from each well of the fixed time point screening plates 1 h after the addition of compound. In both cases, the image pairs obtained at each time point are used to define nuclear and cytoplasmic regions in each cell. Translocation of Caspase-GFP is calculated by dividing the integrated fluorescence intensity of Caspase-GFP in the nucleus by the integrated fluorescence intensity of the chimera in the cytoplasm or as a nuclear-cytoplasmic difference of GFP fluorescence. In the fixed time point screen this translocation ratio is calculated from data obtained from at least 200 cells at each concentration of compound tested. Drug-induced translocation of Caspase-GFP from the cytoplasm to the nucleus is therefore correlated with an increase in the translocation ratio. Molecular interaction libraries including, but not limited to those comprising putative activators or inhibitors of apoptosis-activated enzymes are use to screen the indicator cell lines and identify a specific ligand for the DAS, and a pathway activated by compound activity.

Example 8

Identification of Novel Steroid Receptors from DAS

Two sources of material and/or information are required to make use of this embodiment, which allows assessment of the function of an uncharacterized gene. First, disease associated sequence bank(s) containing cDNA sequences suitable for transfection into mammalian cells can be used. Because every RADE or differential expression experiment generates up to several hundred sequences, it is possible to generate an ample supply of DAS. Second, information from primary sequence database searches can be used to place DAS into broad categories, including, but not limited to, those that contain signal sequences, seven trans-membrane motifs, conserved protease active site domains, or other identifiable motifs. Based on the information acquired from these sources, method types and indicator cell lines to be transfected are selected. A large number of motifs are already well characterized and encoded in the linear sequences contained within the large number genes in existing genomic databases.

In one embodiment, the following steps are taken:
1) Information from the DAS identification experiment (including database searches) is used as the basis for selecting the relevant biological processes. (for example, look at the DAS from a tumor line for cell cycle modulation, apoptosis, metastatic proteases, etc.)
2) Sorting of DNA sequences or DAS by identifiable motifs (ie. signal sequences, 7-transmembrane domains, conserved protease active site domains, etc.) This initial grouping will determine fluorescent tagging strategies, host cell lines, indicator cell lines, and banks of bioactive molecules to be screened, as described supra.
3) Using well established molecular biology methods, ligate DAS into an expression vector designed for this purpose. Generalized expression vectors contain promoters, enhancers, and terminators for which to deliver target sequences to the cell for transient expression. Such vectors may also contain antibody tagging sequences, direct association sequences, chromophore fusion sequences like GFP, etc. to facilitate detection when expressed by the host.
4) Transiently transfect cells with DAS containing vectors using standard transfection protocols including: calcium phosphate co-precipitation, liposome mediated, DEAE dextran mediated, polycationic mediated, viral mediated, or electroporation, and plate into microtiter plates or microwell arrays. Alternatively, transfection can be done directly in the microtiter plate itself.
5) Carry out the cell screening methods as described supra.

In this embodiment, DAS shown to possess a motif(s) suggestive of transcriptional activation potential (for example, DNA binding domain, amino terminal modulating domain, hinge region, or carboxy terminal ligand binding domain) are utilized to identify novel steroid receptors.

Defining the fluorescent tags for this experiment involves identification of the nucleus through staining, and tagging the DAS by creating a GFP chimera via insertion of DAS into an expression vector, proximally fused to the gene encoding GFP. Alternatively, a single chain antibody fragment with high affinity to some portion of the expressed DAS could be constructed using technology available in the art (Cambridge Antibody Technologies) and linked to a fluorophore (FITC) to tag the putative transcriptional activator/receptor in the cells. This alternative would provide an external tag requiring no DNA transfection and therefore would be useful if distribution data were to be gathered from the original primary cultures used to generate the DAS.

Plasmid construct. A eukaryotic expression plasmid containing a coding sequence for a green fluorescent protein—DAS chimera is prepared using GFP mutants. The construct is used to transfect HeLa cells. The plasmid, when transfected into the host cell, produces a GFP fused to the DAS protein product, designated GFP-DASpp.

Cell preparation and transfection. HeLa cells are trypsinized and plated using DMEM containing 5% charcoal/dextran-treated fetal bovine serum (FBS) (Hyclone) and 1% penicillin-streptomycin (C-DMEM) 12-24 hours prior to transfection and incubated at 37° C. and 5% $CO_2$. Transfections are performed by calcium phosphate coprecipitation or with Lipofectamine (Life Technologies). For the calcium phosphate transfections, the medium is replaced, prior to transfection, with DMEM containing 5% charcoal/dextran-treated FBS. Cells are incubated with the calcium phosphate-DNA precipitate for 4-5 hours at 37° C. and 5% $CO_2$, and washed 3-4 times with DMEM to remove the precipitate, followed by the addition of C-DMEM. Lipofectamine transfections are performed in serum-free DMEM without antibiotics according to the manufacturer's instructions. Following a 2-3 hour incubation with the DNA-liposome complexes, the medium is removed and replaced with C-DMEM. All transfected cells in 96-well microtiter plates are incubated at 33° C. and 5% $CO_2$ for 24-48 hours prior to drug treatment. Experiments are performed with the receptor expressed transiently in HeLa cells.

Localization of expressed GFP-DASpp inside cells. To obtain cellular distribution data, nuclei of transfected cells are first labeled with 5 µg/ml Hoechst 33342 (Molecular Probes) in C-DMEM for 20 minutes at 33° C. and 5% $CO_2$. Cells are washed once in Hank's Balanced Salt Solution (HBSS). The cells are analyzed live or they are rinsed with HBSS, fixed for 15 min with 3.7% formaldehyde in HBSS, stained with Hoechst 33342, and washed before analysis.

In a preferred embodiment, image acquisition and analysis are performed using the cell screening system of the present invention. The intracellular GFP-DASpp fluorescence signal is collected by acquiring fluorescence image pairs (GFP-DASpp- and Hoechst 33342-labeled nuclei) from field cells. The image pairs obtained at each time point are used to define nuclear and cytoplasmic regions in each cell. Data demonstrating dispersed signal in the cytoplasm would be consistent with known steroid receptors that are DNA transcriptional activators.

Screening for induction of GFP-DASpp translocation. Using the above construct, confirmed for appropriate expression of the GFP-DASpp, as an indicator cell line, a screen of various ligands is performed using a series of steroid type ligands including, but not limited to: estrogen, progesterone, retinoids, growth factors, androgens, and many other steroid and steroid based molecules. Image acquisition and analysis are performed using the cell screening system of the invention. The intracellular GFP-DASpp fluorescence signal is collected by acquiring fluorescence image pairs (GFP-DASpp and Hoechst 33342-labeled nuclei) from fields cells. The image pairs obtained at each time point are used to define nuclear and cytoplasmic regions in each cell. Translocation of GFP-DASpp is calculated by dividing the integrated fluorescence intensity of GFP-DASpp in the nucleus by the integrated fluorescence intensity of the chimera in the cytoplasm or as a nuclear-cytoplasmic difference of GFP fluorescence. A translocation from the cytoplasm into the nucleus indicates a ligand binding activation of the DASpp thus identifying the potential receptor class and action. Combining this data with other data obtained in a similar fashion using known inhibitors and modifiers of steroid receptors, would either validate the DASpp as a target, or more data would be generated from various sources.

Example 9

Intracellular Microtubule Stability

In another aspect of the invention, an automated method for identifying compounds that modify microtubule structure is provided. In this embodiment, indicator cells are treated with test compounds and the distribution of luminescent microtubule-labeling molecules is measured in space and time using a cell screening system, such as the one disclosed above. The luminescent microtubule-labeling molecules may be expressed by or added to the cells either before, together with, or after contacting the cells with a test compound.

In one embodiment of this aspect of the invention, living cells express a luminescently labeled protein biosensor of microtubule dynamics, comprising a protein that labels microtubules fused to a luminescent protein. Appropriate microtubule-labeling proteins for this aspect of the invention include, but are not limited to α and β tubulin isoforms, and MAP4. Preferred embodiments of the luminescent protein include, but are not limited to green fluorescent protein (GFP) and GFP mutants. In a preferred embodiment, the method involves transfecting cells with a microtubule labeling luminescent protein, wherein the microtubule labeling protein can be, but is not limited to, α-tubulin, β-tubulin, or microtubule-associated protein 4 (MAP4). The approach outlined here enables those skilled in the art to make live cell measurements to determine the effect of lead compounds on tubulin activity and microtubule stability in vivo.

In a most preferred embodiment, MAP4 is fused to a modified version of the *Aequorea Victoria* green fluorescent protein (GFP). A DNA construct has been made which consists of a fusion between the EGFP coding sequence (available from Clontech) and the coding sequence for mouse MAP4. (Olson et al., (1995), J. Cell Biol. 130(3): 639-650). MAP4 is a ubiquitous microtubule-associated protein that is known to interact with microtubules in interphase as well as mitotic cells (Olmsted and Murofushi, (1993), MAP4. In "Guidebook to the Cytoskeleton and Motor Proteins." Oxford University Press. T. Kreis and R. Vale, eds.) Its localization, then, can serve as an indicator of the localization, organization, and integrity of microtubules in living (or fixed) cells at all stages of the cell cycle for cell-based HCS assays. While MAP2 and tau (microtubule associated proteins expressed specifically in neuronal cells) have been used to form GFP chimeras (Kaech et al., (1996) Neuron. 17: 1189-1199; Hall et al., (1997), Proc. Nat. Acad. Sci. 94: 4733-4738) their restricted cell type distribution and the tendency of these proteins to bundle microtubules when overexpressed make these proteins less desirable as molecular reagents for analysis in live cells originating from varied tissues and organs. Moderate overexpression of GFP-MAP4 does not disrupt microtubule function or integrity (Olson et al., 1995). Similar constructs can be made using β-tubulin or α-tubulin via standard techniques in the art. These chimeras will provide a means to observe and analyze microtubule activity in living cells during all stages of the cell cycle.

In another embodiment, the luminescently labeled protein biosensor of microtubule dynamics is expressed, isolated, and added to the cells to be analyzed via bulk loading techniques, such as microinjection, scrape loading, and impact-mediated loading. In this embodiment, there is not an issue of overexpression within the cell, and thus α and β tubulin isoforms, MAP4, MAP2 and/or tau can all be used.

In a further embodiment, the protein biosensor is expressed by the cell, and the cell is subsequently contacted with a luminescent label, such as a labeled antibody, that detects the protein biosensor, endogenous levels of a protein antigen, or both. In this embodiment, a luminescent label that detects α and β tubulin isoforms, MAP4, MAP2 and/or tau, can be used.

A variety of GFP mutants are available, all of which would be effective in this invention, including, but not limited to, GFP mutants which are commercially available (Clontech, California).

The MAP4 construct has been introduced into several mammalian cell lines (BHK-21, Swiss 3T3, HeLa, HEK 293, LLCPK) and the organization and localization of tubulin has been visualized in live cells by virtue of the GFP fluorescence as an indicator of MAP4 localization. The construct can be expressed transiently or stable cell lines can be prepared by standard methods. Stable HeLa cell lines expressing the EGFP-MAP4 chimera have been obtained, indicating that expression of the chimera is not toxic and does not interfere with mitosis.

Possible selectable markers for establishment and maintenance of stable cell lines include, but are not limited to the neomycin resistance gene, hygromycin resistance gene, zeocin resistance gene, puromycin resistance gene, bleomycin resistance gene, and blasticadin resistance gene.

The utility of this method for the monitoring of microtubule assembly, disassembly, and rearrangement has been demonstrated by treatment of transiently and stably transfected cells with microtubule drugs such as paclitaxel, nocodazole, vincristine, or vinblastine.

The present method provides high-content and combined high throughput-high content cell-based screens for anti-microtubule drugs, particularly as one parameter in a multi-parametric cancer target screen. The EGFP-MAP4 construct used herein can also be used as one of the components of a high-content screen that measures multiple signaling pathways or physiological events. In a preferred embodiment, a combined high throughput and high content screen is employed, wherein multiple cells in each of the locations containing cells are analyzed in a high throughput mode, and only a subset of the locations containing cells are analyzed in a high content mode. The high throughput screen can be any screen that would be useful to identify those locations containing cells that should be further analyzed, including, but not limited to, identifying locations with increased luminescence intensity, those exhibiting expression of a reporter gene, those undergoing calcium changes, and those undergoing pH changes.

In addition to drug screening applications, the present invention may be applied to clinical diagnostics, the detection of chemical and biological warfare weapons, and the basic research market since fundamental cell processes, such as cell division and motility, are highly dependent upon microtubule dynamics.

Image Acquisition and Analysis

Image data can be obtained from either fixed or living indicator cells. To extract morphometric data from each of the images obtained the following method of analysis is used:
1. Threshold each nucleus and cytoplasmic image to produce a mask that has value=0 for each pixel outside a nucleus or cell boundary.
2. Overlay the mask on the original image, detect each object in the field (i.e., nucleus or cell), and calculate its size, shape, and integrated intensity.
3. Overlay the whole cell mask obtained above on the corresponding luminescent microtubule image and apply one or more of the following set of classifiers to determine the micrtotubule morphology and the effect of drugs on microtubule morphology.

Microtubule morphology is defined using a set of classifiers to quantify aspects of microtubule shape, size, aggregation state, and polymerization state. These classifiers can be based on approaches that include co-occurrence matrices, texture measurements, spectral methods, structural methods, wavelet transforms, statistical methods, or combinations thereof. Examples of such classifiers are as follows:
1. A classifier to quantify microtubule length and width using edge detection methods such as that discussed in Kolega et al. ((1993). *BioImaging* 1:136-150), which discloses a non-automated method to determine edge strength in individual cells), to calculate the total edge strength within each cell. To normalize for cell size, the total edge strength can be divided by the cell area to give a "microtubule morphology" value. Large microtubule morphology values are associated with strong edge strength values and are therefore maximal in cells containing distinct microtubule structures. Likewise, small microtubule morphology values are associated with weak edge strength and are minimal in cells with depolymerized microtubules. The physiological range of microtubule morphology values is set by treating cells with either the microtubule stabilizing drug paclitaxel (10 µM) or the microtubule depolymerizing drug nocodazole (10 µg/ml).
2. A classifier to quantify microtubule aggregation into punctate spots or foci using methodology from the receptor internalization methods discussed supra.
3. A classifier to quantify microtubule depolymerization using a measure of image texture.
4. A classifier to quantify apparent interconnectivity, or branching (or both), of the microtubules.
5. Measurement of the kinetics of microtubule reorganization using the above classifiers on a time series of images of cells treated with test compounds.

In a further aspect, kits are provided for analyzing microtubule stability, comprising an expression vector comprising a nucleic acid that encodes a microtubule labeling protein and instructions for using the expression vector for carrying out the methods described above. In a preferred embodiment, the expression vector further comprises a nucleic acid that encodes a luminescent protein, wherein the microtubule binding protein and the luminescent protein thereof are expressed as a fusion protein. Alternatively, the kit may contain an antibody that specifically binds to the microtubule-labeling protein. In a further embodiment, the kit includes cells that express the microtubule labeling protein. In a preferred embodiment, the cells are transfected with the expression vector. In another preferred embodiment, the kits further contain a compound that is known to disrupt microtubule structure, including but not limited to curacin, nocodazole, vincristine, or vinblastine. In another preferred embodiment, the kits further comprise a compound that is known to stabilize microtubule structure, including but not limited to taxol (paclitaxel), and discodermolide.

In another aspect, the present invention comprises a machine readable storage medium comprising a program containing a set of instructions for causing a cell screening system to execute the disclosed methods for analyzing microtubule stability, wherein the cell screening system comprises an optical system with a stage adapted for holding a plate containing cells, a digital camera, a means for directing fluorescence or luminescence emitted from the cells to the digital camera, and a computer means for receiving and processing the digital data from the digital camera.

Example 10

Neurite Outgrowth

A major interest for drug discovery is the identification of compounds that affect the growth of neurites from neurons. Drugs that promote nerve growth will be of use for treating a wide variety of diseases and trauma that result in neuropathy and nerve injury, including but not limited to spinal cord injury, neuropathy resulting from diseases such as diabetes and stroke, Parkinson's disease, and other forms of dementia including Alzheimer's disease.

Thus, in another aspect, the present invention provides automated methods, kits, and computer readable media for analyzing neurite outgrowth. The methods of this embodiment comprise providing an array of locations comprising cells, wherein the cells possess at least a first luminescently labeled reporter molecule that reports on cell number, and at least a second luminescently labeled reporter molecule that reports on neurite outgrowth, wherein the cells comprise neurons;

imaging or scanning multiple cells in each of the locations containing multiple cells to obtain luminescent signals from the first and second luminescently-labeled reporter molecule;

converting the luminescent signals into digital data; and utilizing the digital data to automatically make measurements, wherein the measurements are used to automatically calculate changes in the distribution, environment or activity of the first and second luminescently labeled reporter molecules on or within the cells, wherein the calculated changes provide a measure of neurite outgrowth.

As used herein, the term "neurons" or "neuronal cells" includes any cell population that includes neurons of any type, including, but not limited to, primary cultures of brain cells that contain neurons, isolated cell cultures comprising primary neuronal cells, neuronal precursor cells, tissue culture cells that are used as models of neurons (such as PC12 cells, which are a neoplastic neuronal cell line cloned from rat pheochromocytoma), or mixtures thereof.

As used herein, the term "neurite" refers to any processes and/or structures that grow from a neuron's cell body including but not limited to axons, dendrites, neurites, intermediate segments, terminal segments, filopodia and growth cones.

As used herein, the phrase "neurite outgrowth" includes positive neurite outgrowth, neurite outgrowth inhibition, neurite outgrowth degradation, and other changes in neurite morphology.

As used herein, the phrase "the cells possess one or more luminescent reporter molecules" means that the luminescent reporter molecule may be expressed as a luminescent reporter molecule by the cells, added to the cells as a luminescent reporter molecule, or luminescently labeled by contacting the cell with a luminescently labeled molecule that binds to the reporter molecule, such as a dye or antibody, that binds to the reporter molecule. The luminescent reporter molecule can be expressed or added to the cell either before, simultaneously with, or after treatment with the test substance.

In another embodiment, the method further comprises contacting the neurons with a test compound, and wherein the calculated changes indicate whether the test compound has modified neurite outgrowth in the neurons. If a mixed cell culture is used, and the nuclei of the other cells in the mixed culture are to be identified, such as the astrocytes, oligodendrocytes, or microglia, then fluorescent probes that are specific to those cell types and are labeled with a different fluorophore are used, and sufficient images per field (i.e. more than two) are acquired to identify astrocytes, oligodendrocytes, or microglia. This embodiment of the invention can be used to discover compounds that affect (positively or negatively) neurite outgrowth from neuronal cells, as well to identify conditions that are toxic to neurons and affect their neurites' morphology, including without limitation neurite length, number, and branching. For such neurotoxicity studies, the method would comprise identifying compounds that degrade neurites, or identifying test compounds that inhibit the activity of known neurotoxins.

In a preferred embodiment, the first luminescently labeled reporter molecule comprises a DNA binding compound. In a further preferred embodiment, the second luminescently labeled reporter molecule comprises a compound that selectively detects a cell component selected from the group consisting of cytoplasm, membrane, and cellular proteins. In a further embodiment, the second luminescently labeled reporter molecule is neuron-specific. In another embodiment, the cells comprise at least a third luminescently labeled reporter molecule that is neuron-specific, or specific to other cell types of interest, including but not limited to microglia, oligodendrocytes, and astrocytes.

In another embodiment, the method further comprises contacting the cells with a control compound known to modify neurite outgrowth, and utilizing the calculated changes to determine whether the test stimulus inhibited the control compound from modifying neurite outgrowth in the neurons. Alternatively, no test stimulus is added, and the measurements and calculated changes are made after removal of the control compound, to determine the effects of such removal on neurite outgrowth.

In a further embodiment, sub-regions of the array of locations are sampled multiple times at intervals to provide kinetic measurement changes in the distribution, environment or activity of the luminescent reporter molecules on or within the cells In addition, other high content or high throughput assays, including without limitation those described throughout the application, can be used in combination with the present assay, to measure the physiological state of the same neurons upon compound treatment. Preferred assays for use in a multiparametric assay with the present method are cell viability assays, apoptosis assays, and G-protein coupled receptor (GPCR) and other receptor internalization assays.

This aspect of the invention provides a way to automatically scan arrays of cell populations treated with different compounds and automatically quantify the neurite outgrowth of the neuronal cells both collectively and individually. The neurons do not have to be isolated from a mixture of different cell types or different neuronal cell types to be used in this embodiment, and thus the method can be applied to primary brain cultures.

The present invention further provides computer readable storage media comprising a program containing a set of instructions for causing a cell screening system to execute the methods of this aspect of the invention, wherein the cell screening system comprises an optical system with a stage adapted for holding a plate containing cells, a means for moving the stage or the optical system, a digital camera, a means for directing light emitted from the cells to the digital camera, and a computer means for receiving and processing the digital data from the digital camera. In a preferred embodiment, the cell screening system is that disclosed above.

The invention further provides kits for analyzing neurite outgrowth, or for identifying compounds that modify neurite outgrowth, comprising at least one neuron-specific luminescent reporter molecule; at least one nucleus-specific luminescent reporter molecule; and instructions for using the neuron-specific luminescent reporter molecule and the nucleus-specific luminescent reporter molecule to analyze neurite outgrowth, or to identify compounds that modify neurite outgrowth.

Identification of Neurons

In one embodiment, all cells in the sample are labeled with a luminescent reporter molecule marker to identify their locations. Once the cell locations are identified, a cell count can be made. Typically, the nucleic acid dye Hoechst 33342 is used as a luminescent reporter molecule to identify the nuclei of all the cells. However, other nuclear labels can also be used. Nucleic acid fluorescent stains are of two kinds: those that can cross the plasma membrane of live cells, and those that are membrane impermeant. Examples of membrane permeant nucleic acid stains include DAPI, dihydroethidium, hexidium iodide, Hoechst 33258, and the SYTO® dye series (Molecular Probes). To label nuclei with membrane-impermeant dyes, the plasma membrane has to be permeabilized. Examples of membrane-impermeant nucleic acid dyes include cyanine nucleic acid labels such as TOTO®, YOYO®, BOBO™, POPO™, TO-PRO®, YO-PRO®, BO-PRO™ and PO-PRO™ (Molecular Probes), ethidium analogs such as ethidium-acridine heterodimer, ethidium bromide, ethidium diazide and ethidium homodimers 1 and 2, propidium iodide, and the green nucleic acid stain SYTOX® (Molecular Probes). In addition, other components of the cells, such as the cytoplasm, can be labeled to identify all of the cells in the culture if the neurons are sparsely plated. In a preferred embodiment, a nuclear label is used. Examples of some cytoplasmic stains are given below.

If the sample consists of a mixture of brain cells (including cell types other than neurons), the luminescently labeled nuclei that belong to neurons are identified. The neurons are distinguished from the other cells by a neuronal specific luminescent reporter molecule with luminescence of a different wavelength from the nuclei marker and any other cell markers or other luminescent reporter molecules that are being used. The nuclei that coincide with the neuron-specific marker are identified as those nuclei in the mixed cell population that belong to neurons. There are many different neuron-specific labeling markers that can be used. Some examples of neuron specific labeling strategies include, but are not limited to: indirect immunofluorescence against neurofilaments, indirect immunofluorescence against βIII-tubulin, and indirect immunofluorescence against neurotrophic factors such as the ciliary neurotrophic factor (CNTF), all being neuron-specific antigens and proteins.

The cells are luminescently labeled so all of their processes can be visualized, whether the culture consists only of neurons or neuronal-like cells, or neurons in a mixed cell culture. There are several targets on neurons that can be luminescently labeled to allow visualization of the processes:

(1) Cytoplasmic Staining: The cytoplasm can be stained with any standard cytoplasmic stain. Examples of such stains are CMFDA (chloromethyl fluorescein diacetate), or CMTMR (chloromethyl tetramethylrhodamine) (Molecular Probes). Alternatively, the cells can be engineered to express an autofluorescent protein such as Green Fluorescent Protein (GFP). The expressed GFP in the cytoplasm will allow the neuron's processes to be visualized.

(2) Membrane Staining: The membrane stain can either be a standard lipid dye such as diI (dioctadecylindocarbocyanine) (Molecular Probes), or can be a fluorescently labeled protein that is on the cell's membrane. To fluorescently label proteins, one can use either immunofluorescence against cell surface proteins (using standard immunofluorescent staining techniques) or a fluorescent ligand that binds a membrane protein. This strategy can serve a dual purpose in that, in addition to identifying the neuron shape and processes, it can also be used to specifically and selectively identify neurons from a mixed brain culture. Examples of neuron specific markers that are on the membrane are the various neurotrophic factors. For example, indirect immunofluorescence against the ciliary neurotrophic factor CNTF on the surface of neurons can delineate the architecture of the neuron.

(3) Staining of Cellular Proteins: Certain cytoplasmic stains label cellular proteins, some of which are specific to neurons. This category includes cytoskeletal proteins that help delineate neurons. Example of this include, but are not limited to: indirect immunofluorescence against neurofilaments, or against βIII-tubulin, both which are neuron-specific cytoskeletal proteins.

(4) A combination of all of these staining strategies can be used to better identify the neuronal processes and outgrowing neurites.

Identification of Compounds that Stimulate Neurite Outgrowth

Cells are plated onto a substrate, which can be made of any optically clear material, including but not limited to glass, plastic, or silicon wafer, such as a conventional light microscope coverslip. In certain situations, a plastic substrate is sufficient for good attachment of the cells. However, for some cell types, the substrate needs to be coated with specific extracellular matrices for good attachment and growth. For example, PC12 cells need to be grown on a collagen substrate. The compound(s) to be tested are then added to the cells. After the appropriate amount of time the neuronal cells are luminescently labeled (if they were not previously labeled) and then images are acquired and analyzed automatically to quantify neurite outgrowth, as described below. In some experiments done with PC12 cells treated with Nerve Growth Factor (NGF), the cells were luminescently labeled, imaged, and analyzed two to seven days after NGF treatment.

Identification of Compounds that Inhibit Neurite Outgrowth

The neuronal cells are first plated onto a substrate as above. The cells are treated with the compound to be tested and with a control compound (such as Nerve Growth Factor (NGF)) that is known to stimulate neurite outgrowth, wherein treatment with the control compound is done either before, after, or simultaneously with test compound treatment. After an appropriate time period, images are acquired and analyzed automatically to quantify neurite outgrowth, as described below.

Identification of Conditions that are Toxic to Neurons and Neurites

The neuronal cells are first plated onto a substrate as above, and treated to allow neurite outgrowth. For example, the cells could be contacted with NGF, as described above. After neurite outgrowth occurs, the cells are treated with the condition to be tested for toxicity towards neurons and neurites. Examples of such conditions could be addition of a concentration range of a potentially toxic compound, alteration of a physical parameter critical to the cells' growth, or in some cases, withdrawal of the factor that stimulates neurite outgrowth, such as NGF. After an appropriate time period images are acquired and analyzed automatically, as described below, to quantify the neurite outgrowth.

Image Acquisition and Analysis

When neuronal cells are sparse or do not have a large degree of neurite outgrowth, individual cells can be easily identified. However, as neurites start to grow and the cells start putting out numerous processes, these processes may intersect and the neuronal cells become part of a large cluster of cells. Thus, the entire cell cluster becomes a single connected luminescent entity. The different processes and structures that grow from a neuron's cell body include axons, dendrites, neurites, intermediate segments, terminal segments, filopodia and growth cones. For image acquisition and analysis, all of the processes and structures are classified into two groups: (1) the cell body (also known as soma), and (2) the neurites. The cell body is the central part of the neuron that contains the nucleus and has a roughly compact, round morphology. All of the outgrowths and processes emerging from the cell body are classified as neurites. A neurite may branch, intersect other neurites or have smaller processes growing from it, all of which are considered as part of their parent neurite for the purpose of image analyses. Thus, a neurite has one origin, which is in the cell body, but may have multiple end points if it branches. The results obtained from applying the present method allow the user to define and classify the neurites according to their classification guidelines. For example, in one publication, axons are defined as the longest continuous neurite from the cell body, neurite segments between 0.7 µm and 5.1 µm in length are defined as filopodia, and those longer than 5.1 µm are called neurites if emerging from the cell body or terminal segments if an end is attached to a neurite (Ramakers et al, 1998, Developmental Brain Research, 108:205-216.

The neurite outgrowth methods of the present invention perform the following types of analyses:

a. Identify the cells' nuclei. If the sample is a mixed culture of cells, it identifies the nuclei which belong to neurons. The nuclei are used to identify and keep count of the neurons, and also to determine the number of cell bodies in a cluster of neurons;

b. Identify the degree of neurite outgrowth in the well and for the individual cell clusters (if the cells are sparse or neurite outgrowth is limited, the cell clusters would only consist of one cell). This is achieved by measuring the morphology of the neuronal cells (or cell clusters), which includes the cell body and the neurites extending from them;

c. Measure specific properties and morphological features of the neurites such as their lengths, number, and branch points;

d. Measure which and how many of the neurons can be considered positive for neurite outgrowth; and/or e. Combine the analysis with other HCS analyses on the same cells or cell clusters. Examples of other HCS assays that can be applied include, but are not limited to assays for cell viability, apoptosis, or GPCR and other receptor internalization.

For example, in one embodiment of the method, the following features of the cells, neurons and neurites are measured and reported:

In addition, the above features can be combined (such as to normalize one feature with the other, or to correlate two or more features) to be reported as new features.

A preferred method to quantify neurite outgrowth and measure these features is described below. As used therein, the following terms have the given meaning:

"Image" refers to a display of pixels that have intensities.

"Pixel" refers to an (x,y) coordinate location within the array, along with the associated intensity value.

"Binary Image" refers to an image in which each pixel has an intensity of either 0 or 1. This is usually derived from an image whose pixels have a full intensity range. Binarization assigns those pixels with an intensity above a threshold to have an intensity of 1 in the binary image. The pixels that have intensities less than or equal to the threshold have intensity 0 in the binary image. The pixels "contained in" a binary image are considered merely to be the pixels that have value 1. The binarized image can also be used as a mask to be applied to other images to measure the intensities of the pixels that are colocalized with the binary masked structures.

"Thresholding" refers to the process of selecting those pixels of an image whose intensity lie above a value termed a threshold. The result of thresholding is stored within a binary image wherein pixels above the threshold have value 1 and the others have value 0.

"Autohresholding" refers to the process of automatically selecting and applying a suitable threshold value for an image by considering the brightness distribution present in the image. A variety of different methods of selecting the threshold are known; the one used in this assay is known as the "isodata method", but other autothresholding schemes can be used.

Connected Component: Any pixel (whose location is not along the image boundary) has 8 neighboring pixels (4 pixels with which it shares a side, and 4 others with which it shares a corner). A pixel is said to be 8-connected to each of its 8 neighboring pixels. "8-connected components" is a method

TABLE 2

List Of Output Features Reported By The Current Version Of The Neurite Outgrowth Method.

| Parameter | Units | Description |
| --- | --- | --- |
| Neurite Outgrowth Index | % | Percentage of neurons that are positive for neuiite outgrowth (i.e. percentage of neurons whose summed neurite lengths are greater than a user entered minimum length threshold). |
| Degree of Outgrowth | Number | The neuron's form factor is used as a measure of the degree of neurite outgrowth. The form factor is the square of the cell's perimeter divided by 4π times its area. It is 1 for a circle, a little larger than 1 for cells without outgrowth, and much larger for cells with significant outgrowth and branching. This parameter is influenced by the number of neurites, their lengths, as well as their branching. The reported parameter is the mean form factor for all identified neurons and unresolved neuronal clusters. |
| Total Cells Counted | Number | Total number of cells determined from the nuclear stain (such as Hoechst 33342) |
| Number of Neurons | Number | Number of neurons. A cell is identified as a neuron if the intensity of the neuronal stain colocalized with a dilated nuclear mask is greater than a user entered minimum intensity threshold. |
| Number of Positive Neurons | Number | Number of positive neurons. Positive neurons are neurons whose summed neurite lengths are greater than a user entered minimum length threshold. |
| Number of Neurites per Positive Neuron | Number | Number of neurites from positive neurons normalized by the number of positive neurons. |
| Neurite Length per Positive Neuron | µm | Neurite length per positive neuron. Sum of neurite lengths from positive neurons normalized by the number of positive neurons. |
| Neurite Length per Neurite | µm | Neurite length per neurite. Sum of neurite lengths from positive neurons normalized by the number of neurites from positive neurons | of determining which of the pixels that have intensities above an intensity threshold are connected and belong to the same object. In an 8-connected component scheme, if any of the 8 pixels surrounding the pixel of interest have intensities above the intensity threshold, it is identified as part of the same object as the central pixel. Consider the pixels which have intensity 1 in a binary image. These pixels may be divided into separate groups where the separate groups satisfy certain properties: 1) no group contains a pixel that is 8-connected to any pixel of any other group. 2) any two pixels within a group contain a path connecting them that passes through only pixels of that group. The groups satisfying these properties are termed connected components of the image.

The "Form-Factor" can be used as a quantitative measure of neurite outgrowth. It consists of the square of the image object's (e.g. cell or cell cluster) perimeter divided by four times π times the area of the object. (i.e. FF=perimeter$^2$/(4π Area))

If no neurite outgrowth has occurred and the neuronal cell's shape is similar to a circle, the Form Factor will be close to 1. As neurite outgrowth occurs and the cell or cell cluster becomes more branched, the value of this FF measure increases. The average FF over the entire imaged field can be computed to give the degree of neurite outgrowth over the whole well. In addition, the degree of neurite outgrowth for individual neurons or neuronal-cell clusters can also be determined by their individual FF.

Background Compensation: In order to avoid sensitivity from uneven fluorescence distribution, a background compensation filter can be applied to the image. This stage removes low spatial frequency variations from the image. One strategy of doing this is to subtract the background intensity from a neighborhood around each pixel. In order to estimate the background intensity in the neighborhood of a pixel, we average the intensity within a square region centered upon the pixel. Since we do not want to use very bright pixels to form this estimate (very bright pixels are clearly foreground pixels and should not be included in an estimate of the background), we include only pixels lying below some intensity threshold to form the average. Having obtained the background intensity estimate, we subtract this intensity from the pixel intensity. The result, when this operation is performed over the entire image, is a background compensated image.

Branch Identification: A branch is a point when a neurite growing from the main cell body splits into more than one (usually two) neurite segments growing from the neurites. The branch-point or triple-point is the junction where a single branch splits into two or multiple branches. The image is analyzed to find and count branch points.

Figure 25A:
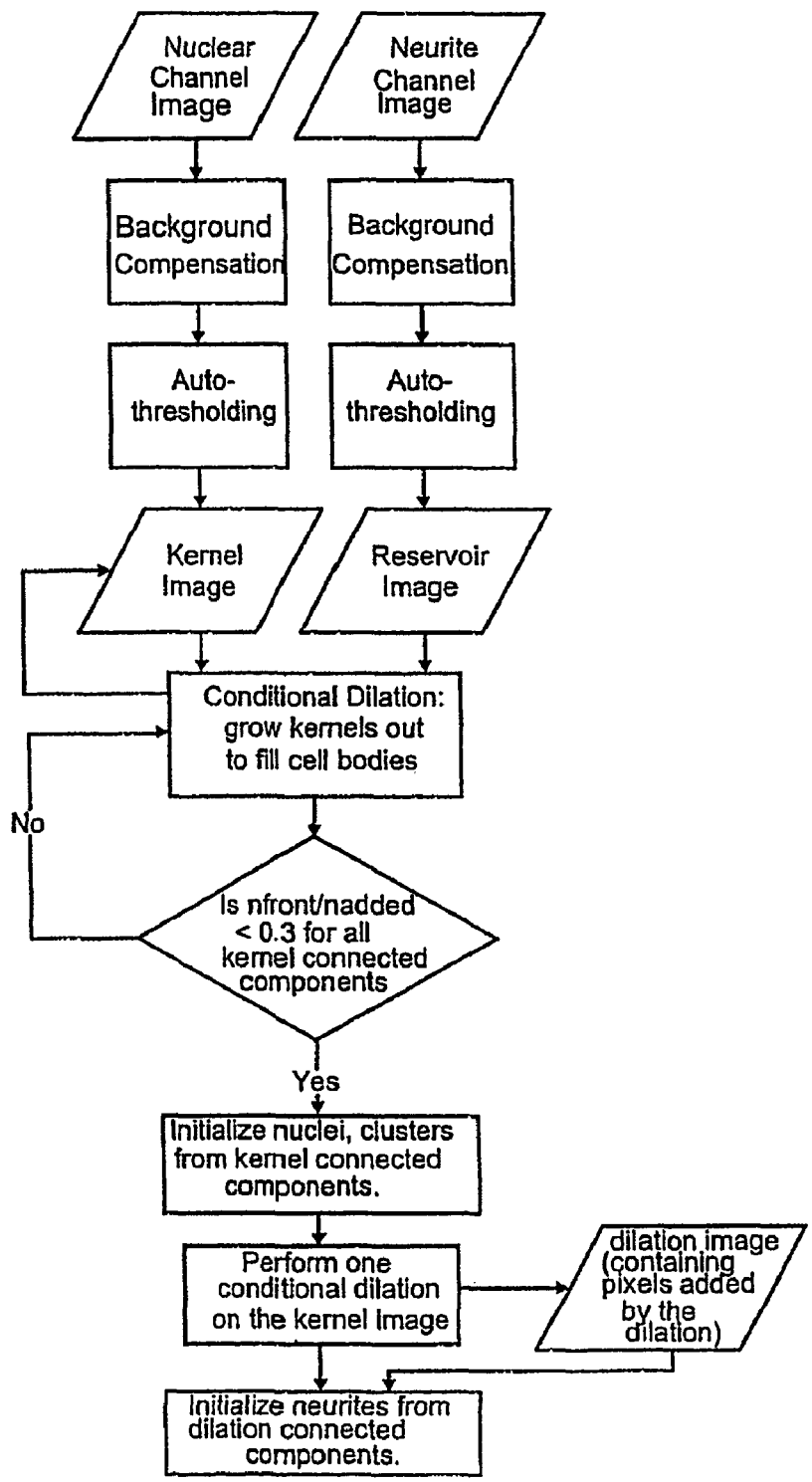
FIG. 25 (A) Flowchart of image acquisition initialization phase; (B) Flowchart of image acquisition iteration phase.
Figure 25B:
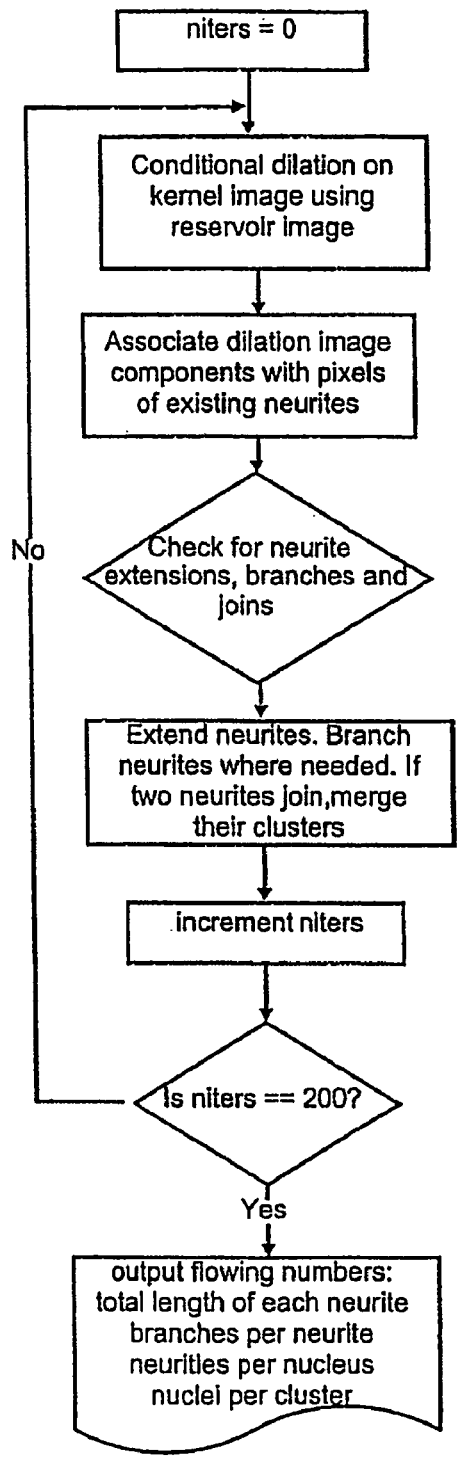

Image Acquisition a. Preferred Embodiment (See FIG. 25A-B)

Inputs to the Method:

Two images are provided as input to the method: a nuclear channel image and a neurite channel image. In the nuclear channel image, the cells' nuclei are labeled with Hoechst 33342 or some other fluorescent or luminescent nuclear stain. In the neurite channel image, the neuronal cell body, and its attached neurites are fluorescently or luminescently labeled.

Initialization Phase:

The initialization phase commences with an optional background compensation on both the nucleus and neuron images. The background compensation stage is applied in order to reduce the effect of uneven illumination and to improve detection.

A binary image is generated for both the nuclear channel image and the neurite channel image by application of a threshold; auto-thresholding is the preferred method as it does not require user input.

Nuclear Channel:

A binary image is generated from the nuclear channel image by the application of an auto-threshold. One connected component is present in this kernel image per neuronal nucleus or nuclear clump. The location coordinate of each nucleus is determined by first applying the binary kernel image as a mask over the background-compensated nuclear image, and then using a peak-detection routine to select the pixel which has the peak maximum intensity. This pixel is tagged as the position coordinate for each nucleus.

Neurite Channel:

A binary reservoir image is generated from the neurite channel image by the application of an auto-threshold. The pixels in this reservoir image will generally be a superset of the pixels in the nuclear kernel image.

Identification of Cell Bodies

The neurons consist of cell bodies with neurites extending from them. Each cell body contains one nucleus, and the cell body covers a larger area than the nucleus. Before starting to quantify neurite outgrowth, the cell bodies, which are the source of the neurites, need to be identified. Thus, a series of dilations are performed from each nuclei's peak pixel until the connected components of the kernel image (which correspond to neuronal nuclei) expand to fill out the associated neuronal cell bodies. The dilations performed are termed conditional dilations; each time the dilation is applied, a layer of one pixel is added to the kernel on the condition that the pixels in that layer are present in the neuron reservoir image. This means that the increase in area due to the dilation has still not extended beyond the cell body's boundaries. During each dilation, the numbers nfront and nadded are measured for each connected component in the kernel image. Nfront is the number of pixels that would be added to the connected component by a simple (unconditional) dilation, which is just dilation by an additional pixel. Nfront can be thought of as the new perimeter, measured in number of pixels, of the object due to the latest dilation. Nadded is the number of pixels that are actually added by the conditional dilation—conditional because after a one pixel dilation, only those pixels in the new perimeter which are positive in the reservoir image are counted. Thus, nadded is the number of pixels in the new perimeter which has an intensity of 1 in the binary reservoir image. If the ratio nadded/nfront is computed to be less than some user-defined number threshold in the course of a dilation (we find that a range from 0.05 to 0.3 empirically works with our test images), no more dilations are performed on that connected component. This means that the extent of the cell body has been reached, and no more dilations are required. The additional pixels in subsequent dilations that are positive in the binary reservoir image belong to actual neurites growing out from the cell body. The extent of the cell body can be reported as the cell body area. When all connected components have reached this stage (i.e. all the individual nuclei have been processed to this stage), then the next step of the method is initiated.

At this point, the kernel image contains one connected component (i.e. one entity) for each neuronal cell body.

Iteration Phase:

The next step is to identify the neurites extending from each cell body. For this, one conditional dilation is performed on the kernel image in order to identify each neurite stub. The term dilation image describes the image containing only the positive binary pixels added by a dilation. Each connected component in the dilation image is termed a node. Each node is used to initialize a one-node neurite data structure. A neurite data structure is intended to represent the physical neurite as it extends outward from the neuronal cell body, potentially containing multiple branches and potentially joining with other neurites.

Next, conditional dilations are successively performed upon the kernel image until no further pixels from the reservoir image remain that are contiguous to pixels of the kernel image. In the dilation image produced by each such dilation, the set of nodes is computed. Each node represents either the continuation of a neurite object, a branching of a neurite object, or the joining of two neurite objects. An association is formed between a node and an existing neurite object if one or more pixels of a node are adjacent to the pixels of the neurite object. If a node is associated with more than one neurite object, then it represents a join point. If multiple nodes are associated with a neurite object, then it represents a branch point. If a node is associated with just one neurite object and that neurite object is associated only with the said node, then the node is an extension of the neurite object. The extension, branch or join is recorded. In the case of joins, the neurite objects involved are merged.

The entire neurite is identified by linking together its set of connected nodes, and then the neurite's length is measured. Length threshold criteria may be applied to classify the different neurites. One application of such criteria would be to reject neurites that are too short. Each neurite origin is associated with the neuron it originated from. One way of doing this is to link the neurite's origin node with either the nearest cell body or nuclear peak. In certain cell types (e.g. PC12 cells), the neurons form clusters and only a subset of cells within the cluster extend neurites. This association of neurites with their originating neurons identifies the neurites and their originating cells within a cluster of cells.

Output Features:

A variety of different quantities can be measured by this method. First, the number of cells and the number of neurons can be measured and reported. For each neurite, the total length (measured as the sum of the lengths of all its branches) and number of branches can be measured. For each nucleus, the number of neurites that emerge from it can be measured. For each cluster, the form-factor (perimeter$^2$÷(4$\pi$×area)) is measured and reported as the degree of neurite outgrowth. In addition, the neurite lengths from each nuclei are summed, and if greater than a length threshold, the nuclei are identified as being positive for neurite outgrowth. These measures can be combined in different ways to give the output features reported in Table 2.

Validation of Preferred Embodiment

1. Measurement of Neurite Outgrowth in PC6-3 Cells

PC6-3 cells (a sub-clone of PC12 cells) were grown on 96-well microplates whose wells had been coated with collagen. The wells contained different concentrations of NGF (nerve growth factor) (0-1000 ng/ml) to stimulate neurite outgrowth. A control population did not contain NGF. After two days, the cells were fixed and indirect immunofluorescence was performed against βIII-tubulin, using a rabbit anti-βIII-tubulin primary antibody and an ALEXAFLUOR™ 488 conjugated goat anti-rabbit secondary antibody (Molecular Probes). The cells were then fixed in 3.7% formaldehyde for 20 minutes, and the fixative solution also contained 10 µg/ml Hoechst 33342 to label their nuclei. The cells were imaged on the cell screening system of the present invention and then analyzed with a prototype method described above. Results given below are for the form-factor and mean neurite length as a function of NGF concentration:

| NGF Concentration (ng/ml) | Mean Neurite Length (µm) | Mean Form Factor |
|---|---|---|
| 0 | 3.8 | 2.5 |
| 62.5 | 27.8 | 16.3 |
| 250 | 47.6 | 41.5 |
| 1000 | 64.4 | 51.7 |

2. Measurement of Dopamine Toxicity to Neurites from PC12 Cells

PC12 cells were grown for 7 days in the presence of 1 µg/ml NGF on 96 well microplates with collagen-IV coated wells. Varying concentrations of dopamine were added for 3 hours before the cells were fixed in 3.7% formaldehyde for 20 minutes; the fixative solution also contained 10 µg/ml Hoechst 33342. The cells were stained by indirect immunofluorescence using a rabbit primary antibody against βIII-tubulin, and an ALEXAFLUOR™ 488 conjugated goat anti-rabbit secondary antibody. The cells were imaged on the cell screening system of the present invention, and then analyzed with the prototype method described above. Results given below are for the Neurite Outgrowth Index (see Table 2) as a function of dopamine concentration. Each data point is the mean result from 8 wells, and error bars are the standard deviations. The $IC_{50}$ (50% inhibitory concentration) for dopamine toxicity to neurites from this data is 0.46 mM.

Figure 26:
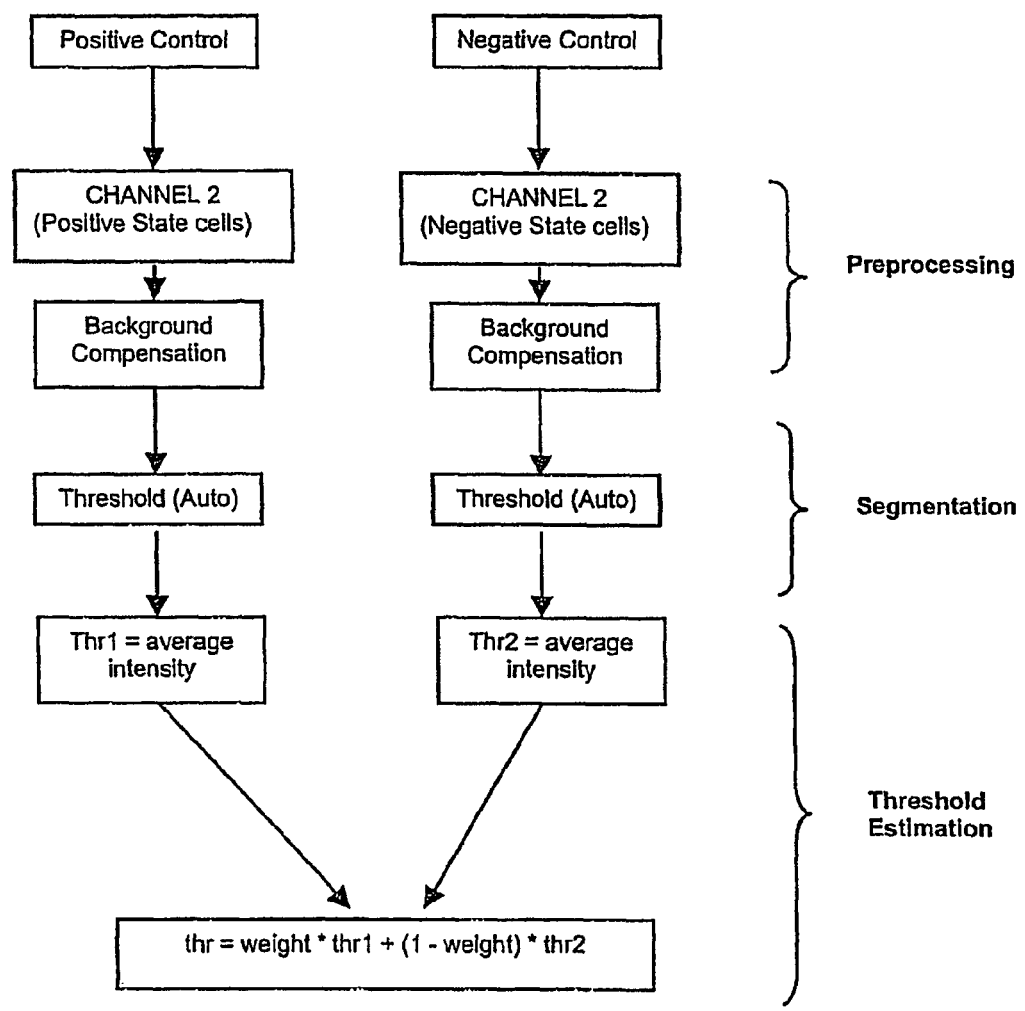
FIG. 26 is a flowchart of the Positive State Detection Threshold Computation.
Figure 27A:
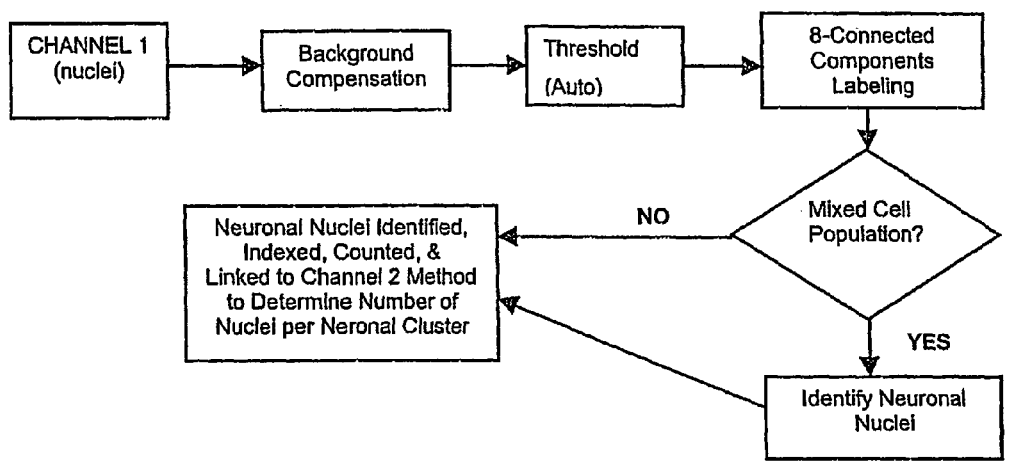
FIG. 27 is a flowchart of Neurite Outgrowth Alternative Quantification Method. (A) Neuronal Nuclei Identification; (B) Neurite Outgrowth Quantification.
Figure 27B:
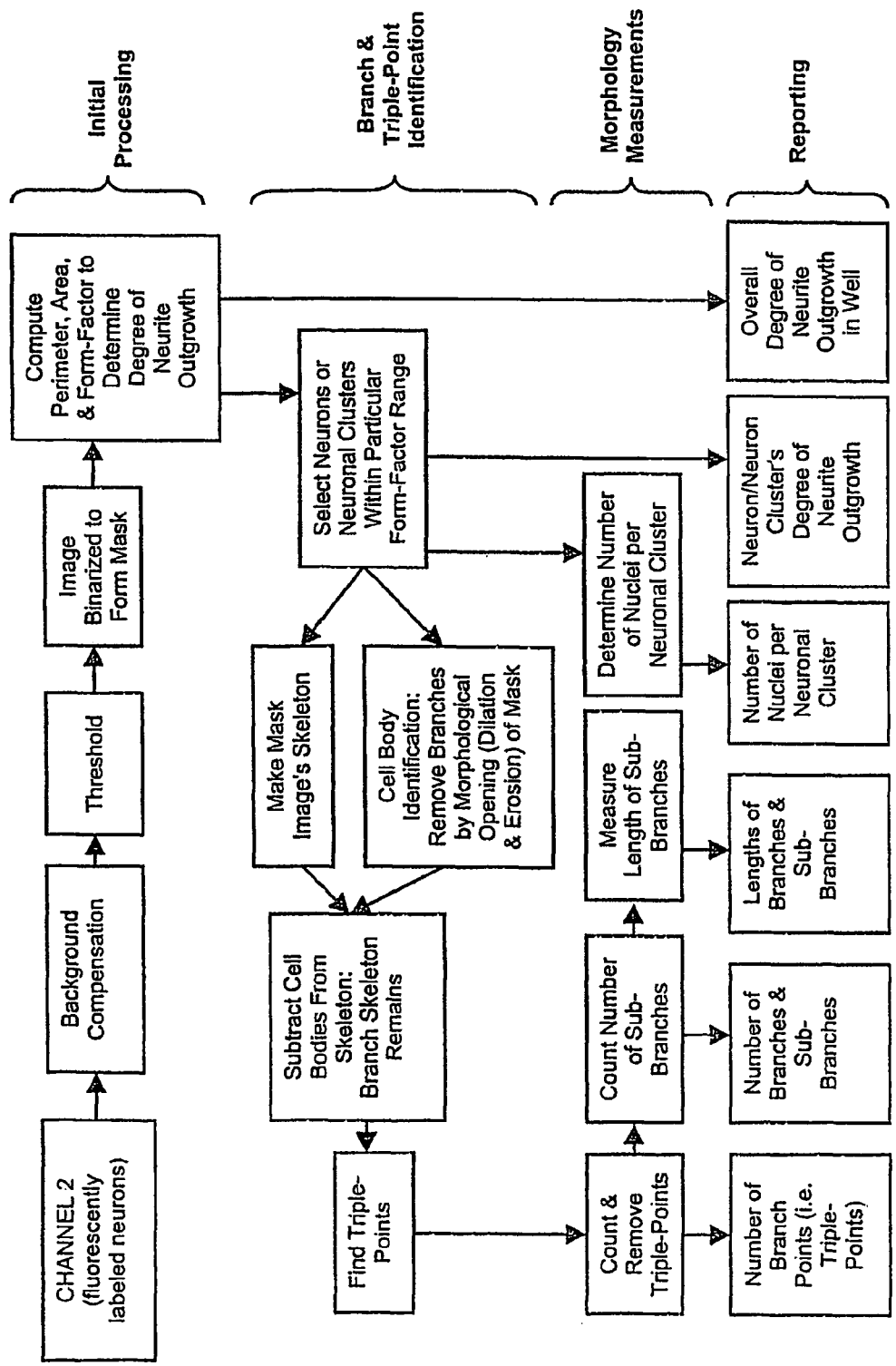

| Dopamine Concentration (mM) | Neurite Outgrowth Index (%) (mean +/− standard deviation) |
|---|---|
| 0.0 | 46 +/− 5 |
| 0.05 | 43 +/− 4 |
| 0.1 | 37 +/− 3 |
| 0.2 | 37 +/− 3 |
| 0.4 | 25 +/− 3 |
| 0.8 | 17 +/− 2 |
| 1.6 | 11 +/− 2 | b. Alternative Image Acquisition Embodiment (See FIGS. 26 and 27A-B)

In an alternative embodiment, the method measures the percentage of cells in a field that are in a particular state, in this case, those that are neurons in a culture containing a mixed population of cell types. A Positive State means that the cell is brightly fluorescent, and a Negative State means that the cell has little or no fluorescence. When a neuron-specific reporter molecule is used, a Positive State occurs for every neuronal cell, and a Negative State for all other cells. To identify neurons, two images are captured per field as discussed above. The number of cells in a Positive State is compared to the total number of all cells to obtain the percentage of Positive State cells in a field.

Furthermore, a mixture of different types of neurons can be assayed for neurite outgrowth. Each neuronal sub-population to be analyzed is identified by a distinct reporter molecule. Such a method can be used, for example, to distinguish GABAnergic neurons from cholinergic neurons in a mixed population, by immunofluorescence against the specific neurotransmitters' receptor.

This alternative embodiment can be summarized as follows:

Detection Threshold Computation

Two control wells are used: a sample where all the cells are in the Positive State, and a sample where all cells are in the Negative State. The Positive State cells are brightly labeled and the Negative State cells are not. In order to improve cell segmentation, all images can be background compensated by subtracting the local average intensity over a user determined area. For the negative control, a threshold is set to minimize the variance of the intensity distributions of the non-cell background and the cells. For the positive control, a threshold is set to minimize the variance of the intensity distributions of the non-cell background and the cells. The Positive State detection threshold is set as a weighted sum of the thresholds computed from the control images.

Detection and Counting of Nuclei (Hoechst Labeled)

The nuclear image is background compensated by subtraction of local average. A threshold is applied to the image. The image has a bimodal intensity distribution due to the dim pixels from the non-cell background and the brighter pixels associated with cells. The threshold is set to minimize the variance of these two distributions. 8-Connected components are labeled and counted. This identifies the area covered by each nucleus, and sets each individual nucleus's mask.

Detection and Count of Positive State

Figure 28:
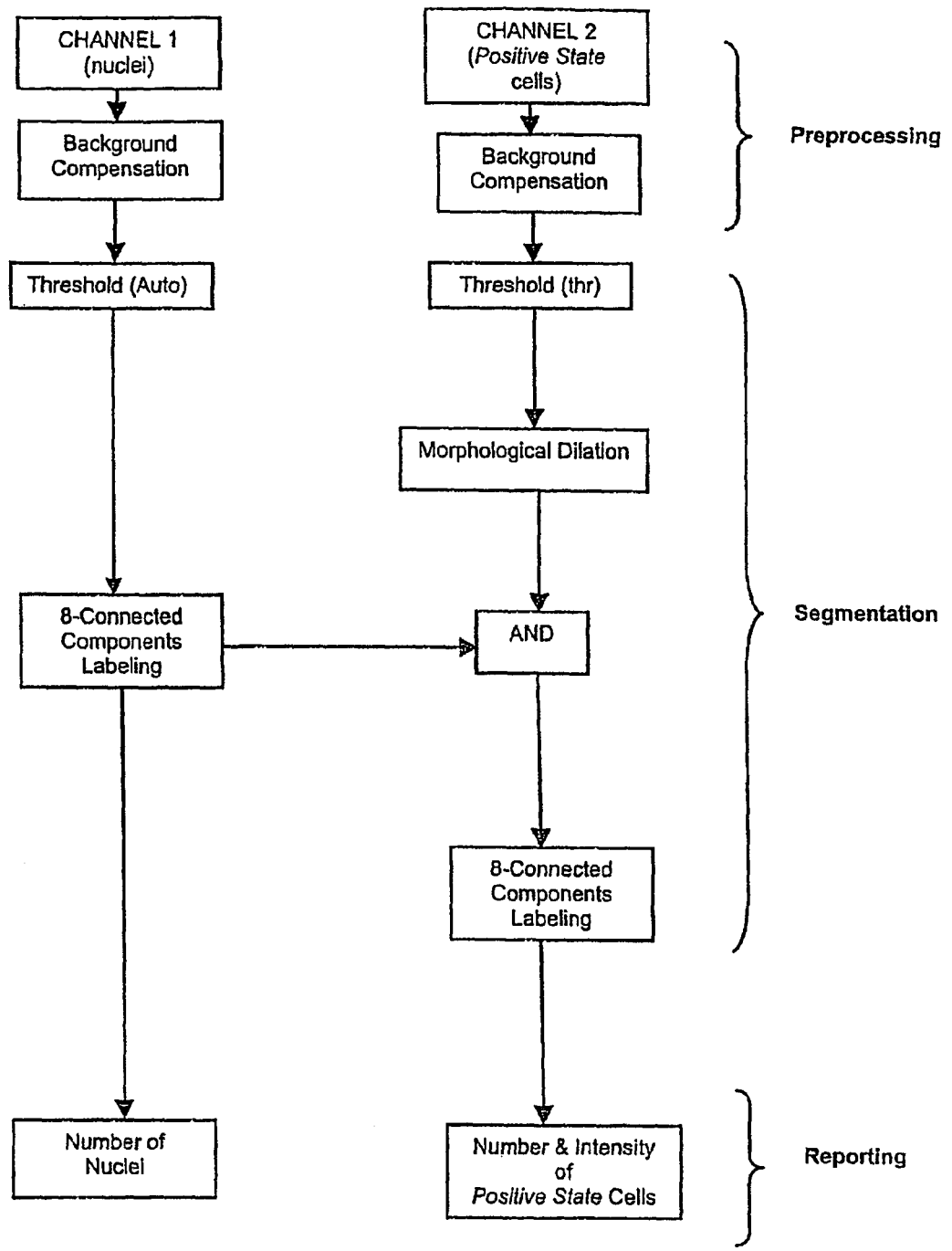
FIG. 28 is a flowchart of the Cell State Detection Method (Morphological Method).
Figure 29:
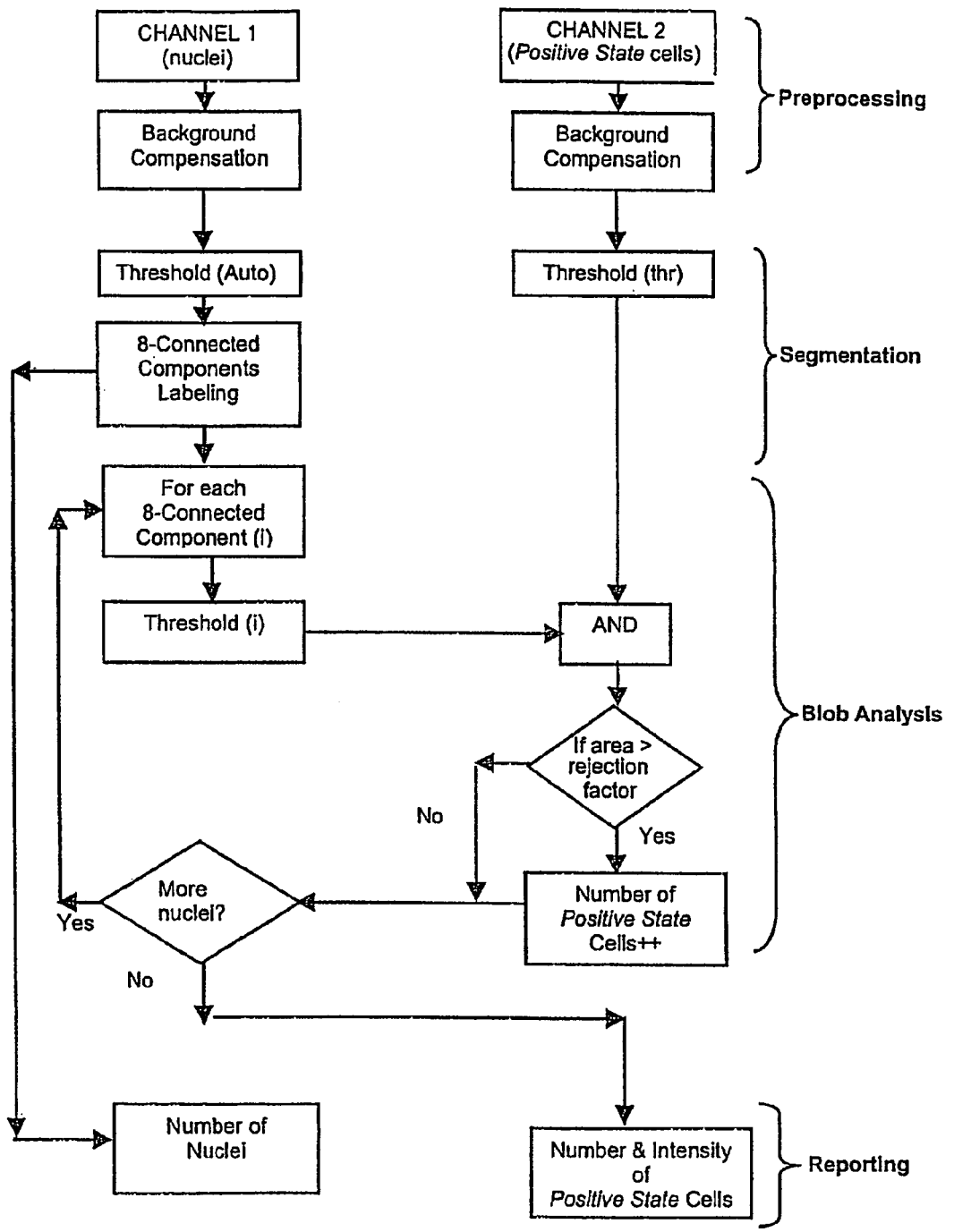
FIG. 29 is a flowchart of the Cell State Detection Method (Blob Analysis Method).

The 8-connected components of the nucleus mask image are labeled. The image where Positive State cells are luminescently labeled is background compensated by subtraction of the local average. Positive State cells are then selected by means of a fixed or autothresholding (selection of pixels above Positive State detection threshold). The positive cells are then identified by either the "Morphological" or "Blob Analysis" method:

a. Morphological method (FIG. 28): A morphological dilation (of 5 pixels for example) is applied to the selected areas. The selected area is logically "AND"ed with the nucleus mask and then the 8-connected components of the resulting area are labeled and counted.
   b. Blob Analysis Method (FIG. 29): The selected area is logically "AND"ed with each separate 8-connected component of the nucleus mask. The area of the resulting image is compared with a threshold (rejection threshold), and if larger, the cell is counted as Positive State.

Linking Positive State Cells (e.g. Neurons) to Neurite Outgrowth Assays

For each well the number of detected nuclei and the number of nuclei in the Positive State (i.e. that are neurons) are saved and reported. The total integrated intensity and the average intensity per pixel can also be reported. Next, the neurite outgrowth methods are applied to the Positive State neuronal cells to quantify and characterize their neurite outgrowth. The Positive State nuclei are used to index and track the Positive State cells.

Measuring Degree of Neurite Outgrowth

To measure the degree of neurite outgrowth, both the perimeter and the area of the neuronal cell or cell cluster are measured. To quantify the degree of neurite outgrowth, we use the Form Factor (FF), as discussed above. A summary of the series of steps involved is as follows:

1. Background Compensation: Same as in preferred embodiment.
2. Image Binarization: The image is then binarized to generate a mask image with all the selected cells. The skeleton of the mask is then also computed.
3. Degree of Outgrowth: Connected components in the binarized image are labeled, each of them representing an individual cell or a cell cluster. The perimeter, area, and form factor of each component is computed.
4. Branch Identification: To compute all the branches, first the cell branches are removed by applying a morphological opening (e.g. an image processing erosion of the image) to the original mask image. Then, from the skeletonized mask image (computed above) the region's main cell bodies are subtracted. This leaves only the skeleton of cell branches.
5. Triple-Point Identification: A triple point is the junction where a single branch splits into two or multiple branches, or different neurite branches intersect. This image is analyzed to find and count triple points. These points are then removed from the image, thus separating each branch and its sub-branches. A connected components labeling is used to count the number of branches and sub-branches and, by counting the number of pixels of each object (branch), the length of each separate branch is also computed.

Triple Point Characterization: Image acquisition can be expanded to include a feature that further characterizes the triple points. As mentioned above, the triple points may be places where neurites from different cells intersect. If a connection is made between these different neurites, certain proteins that are characteristic of these connections may be expressed. Examples may be synaptic vesicle proteins such as synaptobrevin. Immunofluorescence against these proteins using a fluorophore with a spectra distinguishable from other used in the assay allows determination of whether a connection has been made. Comparison with the neuronal luminescent label to determine whether a triple point is indeed co-localized with the immunofluorescence against the protein characterizes the triple point and measures and quantifies whether inter-neurite connections are being made.

Validation Data Using the Alternative Image Acquisition Embodiment

1. Measurement of Neurite Outgrowth in PC12 Cells

PC12 cells were grown on 96-well microplates whose wells had been coated with collagen. Some of the wells contained NGF (nerve growth factor) (0.5-1 µg/ml) to stimulate neurite outgrowth. A control population did not contain NGF. After two days, the cells were labeled with CMFDA according to the manufacturer's instructions. The cells were then fixed in 3.7% formaldehyde for 10 minutes, and the fixative solution also contained 10 µg/ml Hoechst 33342 to label their nuclei. The cells were imaged on the cell screening system of the present invention and then analyzed with a prototype method described above. First, the cells From Factors were calculated.

| Condition | Mean form factor +/− sem |
|---|---|
| +NGF | 18.43 +/− 1 4.57 |
| −NGF | 1.33 +/− 0.05 |

The results from applying the neurite-outgrowth method to a cluster of cells that had been treated with NGF returned the following analysis for on cell cluster:

| Property | Result |
|---|---|
| Number of cell bodies | 3 |
| Degree of neurite outgrowth (form factor) | 70.24 |
| # neurites and neurite segments | 5 |
| # branch points (i.e.: triple points) | 5 |
| Neurite segment length (in µm) | 29, 44, 67, 78, and 92 |

Example 11

Additional Screens

Translocation Between the Plasma Membrane and the Cytoplasm:

Profilactin complex dissociation and binding of profilin to the plasma membrane. In one embodiment, a fluorescent protein biosensor of profilin membrane binding is prepared by labeling purified profilin (Federov et al. (1994), *J. Molec. Biol.* 241:480-482; Lanbrechts et al. (1995), *Eur. J. Biochem.* 230:281-286) with a probe possessing a fluorescence lifetime in the range of 2-300 ns. The labeled profilin is introduced into living indicator cells using bulk loading methodology and the indicator cells are treated with test compounds. Fluorescence anisotropy imaging microscopy (Gough and Taylor (1993), *J. Cell Biol.* 121:1095-1107) is used to measure test-compound dependent movement of the fluorescent derivative of profilin between the cytoplasm and membrane for a period of time after treatment ranging from 0.1 s to 10 h.

Rho-RhoGDI complex translocation to the membrane. In another embodiment, indicator cells are treated with test compounds and then fixed, washed, and permeabilized. The indicator cell plasma membrane, cytoplasm, and nucleus are all labeled with distinctly colored markers followed by immunolocalization of Rho protein (Self et al. (1995), *Methods in Enzymology* 256:3-10; Tanaka et al. (1995), *Methods in Enzymology* 256:41-49) with antibodies labeled with a fourth color. Each of the four labels is imaged separately using the cell screening system, and the images used to calculate the amount of inhibition or activation of translocation effected by the test compound. To do this calculation, the images of the probes used to mark the plasma membrane and cytoplasm are used to mask the image of the immunological probe marking the location of intracellular Rho protein. The integrated brightness per unit area under each mask is used to form a translocation quotient by dividing the plasma membrane integrated brightness/area by the cytoplasmic integrated brightness/area. By comparing the translocation quotient values from control and experimental wells, the percent translocation is calculated for each potential lead compound.

β-Arrestin Translocation to the Plasma Membrane Upon G-Protein Receptor Activation.

In another embodiment of a cytoplasm to membrane translocation high-content screen, the translocation of β-arrestin protein from the cytoplasm to the plasma membrane is measured in response to cell treatment. To measure the translocation, living indicator cells containing luminescent domain markers are treated with test compounds and the movement of the β-arrestin marker is measured in time and space using the cell screening system of the present invention. In a preferred embodiment, the indicator cells contain luminescent markers consisting of a green fluorescent protein β-arrestin (GFP-β-arrestin) protein chimera (Barak et al. (1997), *J. Biol. Chem.* 272:27497-27500; Daaka et al. (1998), *J. Biol. Chem.* 273: 685-688) that is expressed by the indicator cells through the use of transient or stable cell transfection and other reporters used to mark cytoplasmic and membrane domains. When the indicator cells are in the resting state, the domain marker molecules partition predominately in the plasma membrane or in the cytoplasm. In the high-content screen, these markers are used to delineate the cell cytoplasm and plasma membrane in distinct channels of fluorescence. When the indicator cells are treated with a test compound, the dynamic redistribution of the GFP-β-arrestin is recorded as a series of images over a time scale ranging from 0.1 s to 10 h. In a preferred embodiment, the time scale is 1 h. Each image is analyzed by a method that quantifies the movement of the GFP-β-arrestin protein chimera between the plasma membrane and the cytoplasm. To do this calculation, the images of the probes used to mark the plasma membrane and cytoplasm are used to mask the image of the GFP-β-arrestin probe marking the location of intracellular GFP-β-arrestin protein. The integrated brightness per unit area under each mask is used to form a translocation quotient by dividing the plasma membrane integrated brightness/area by the cytoplasmic integrated brightness/area. By comparing the translocation quotient values from control and experimental wells, the percent translocation is calculated for each potential lead compound. The output of the high-content screen relates quantitative data describing the magnitude of the translocation within a large number of individual cells that have been treated with test compounds of interest.

Translocation Between the Endoplasmic Reticulum and the Golgi:

In one embodiment of an endoplasmic reticulum to Golgi translocation high-content screen, the translocation of a VSVG protein from the ts045 mutant strain of vesicular stomatitis virus (Ellenberg et al. (1997), *J. Cell Biol.* 138:1193-1206; Presley et al. (1997) *Nature* 389:81-85) from the endoplasmic reticulum to the Golgi domain is measured in response to cell treatment. To measure the translocation, indicator cells containing luminescent reporters are treated with test compounds and the movement of the reporters is measured in space and time using the cell screening system of the present invention. The indicator cells contain luminescent reporters consisting of a GFP-VSVG protein chimera that is expressed by the indicator cell through the use of transient or stable cell transfection and other domain markers used to measure the localization of the endoplasmic reticulum and Golgi domains. When the indicator cells are in their resting state at 40° C., the GFP-VSVG protein chimera molecules are partitioned predominately in the endoplasmic reticulum. In this high-content screen, domain markers of distinct colors used to delineate the endoplasmic reticulum and the Golgi domains in distinct channels of fluorescence. When the indicator cells are treated with a test compound and the temperature is simultaneously lowered to 32° C., the dynamic redistribution of the GFP-VSVG protein chimera is recorded as a series of images over a time scale ranging from 0.1 s to 10 h. Each image is analyzed by a method that quantifies the movement of the GFP-VSVG protein chimera between the endoplasmic reticulum and the Golgi domains. To do this calculation, the images of the probes used to mark the endoplasmic reticulum and the Golgi domains are used to mask the image of the GFP-VSVG probe marking the location of intracellular GFP-VSVG protein. The integrated brightness per unit area under each mask is used to form a translocation quotient by dividing the endoplasmic reticulum integrated brightness/area by the Golgi integrated brightness/area. By comparing the translocation quotient values from control and experimental wells, the percent translocation is calculated for each potential lead compound. The output of the high-content screen relates quantitative data describing the magnitude of the translocation within a large number of individual cells that have been treated with test compounds of interest at final concentrations ranging from $10^{-12}$ M to $10^{-3}$ M for a period ranging from 1 min to 10 h.

High-Content Screens Involving the Functional Localization of Macromolecules

Within this class of high-content screen, the functional localization of macromolecules in response to external stimuli is measured within living cells.

Glycolytic enzyme activity regulation. In a preferred embodiment of a cellular enzyme activity high-content screen, the activity of key glycolytic regulatory enzymes are measured in treated cells. To measure enzyme activity, indicator cells containing luminescent labeling reagents are treated with test compounds and the activity of the reporters is measured in space and time using cell screening system of the present invention.

In one embodiment, the reporter of intracellular enzyme activity is fructose-6-phosphate, 2-kinase/fructose-2,6-bisphosphatase (PFK-2), a regulatory enzyme whose phosphorylation state indicates intracellular carbohydrate anabolism or catabolism (Deprez et al. (1997) *J. Biol. Chem.* 272:17269-17275; Kealer et al. (1996) *FEBS Letters* 395:225-227; Lee et al. (1996), *Biochemistry* 35:6010-6019). The indicator cells contain luminescent reporters consisting of a fluorescent protein biosensor of PFK-2 phosphorylation. The fluorescent protein biosensor is constructed by introducing an environmentally sensitive fluorescent dye near to the known phosphorylation site of the enzyme (Deprez et al. (1997), supra; Giuliano et al. (1995), supra). The dye can be of the ketocyanine class (Kessler and Wolfbeis (1991), *Spectrochimica Acta* 47A:187-192) or any class that contains a protein reactive moiety and a fluorochrome whose excitation or emission spectrum is sensitive to solution polarity. The fluorescent protein biosensor is introduced into the indicator cells using bulk loading methodology.

Living indicator cells are treated with test compounds, at final concentrations ranging from $10^{-12}$ M to $10^{-3}$ M for times ranging from 0.1 s to 10 h. In a preferred embodiment, ratio image data are obtained from living treated indicator cells by collecting a spectral pair of fluorescence images at each time point. To extract morphometric data from each time point, a ratio is made between each pair of images by numerically dividing the two spectral images at each time point, pixel by pixel. Each pixel value is then used to calculate the fractional phosphorylation of PFK-2. At small fractional values of phosphorylation, PFK-2 stimulates carbohydrate catabolism. At high fractional values of phosphorylation, PFK-2 stimulates carbohydrate anabolism.

Protein kinase A activity and localization of subunits. In another embodiment of a high-content screen, both the domain localization and activity of protein kinase A (PKA) within indicator cells are measured in response to treatment with test compounds.

The indicator cells contain luminescent reporters including a fluorescent protein biosensor of PKA activation. The fluorescent protein biosensor is constructed by introducing an environmentally sensitive fluorescent dye into the catalytic subunit of PKA near the site known to interact with the regulatory subunit of PKA (Harootunian et al. (1993), *Mol. Biol. of the Cell* 4:993-1002; Johnson et al. (1996), *Cell* 85:149-158; Giuliano et al. (1995), supra). The dye can be of the ketocyanine class (Kessler, and Wolfbeis (1991), *Spectrochimica Acta* 47A:187-192) or any class that contains a protein reactive moiety and a fluorochrome whose excitation or emission spectrum is sensitive to solution polarity. The fluorescent protein biosensor of PKA activation is introduced into the indicator cells using bulk loading methodology.

In one embodiment, living indicator cells are treated with test compounds, at final concentrations ranging from $10^{-12}$ M to $10^{-3}$ M for times ranging from 0.1 s to 10 h. In a preferred embodiment, ratio image data are obtained from living treated indicator cells. To extract biosensor data from each time point, a ratio is made between each pair of images, and each pixel value is then used to calculate the fractional activation of PKA (e.g., separation of the catalytic and regulatory subunits after cAMP binding). At high fractional values of activity, PFK-2 stimulates biochemical cascades within the living cell.

To measure the translocation of the catalytic subunit of PKA, indicator cells containing luminescent reporters are treated with test compounds and the movement of the reporters is measured in space and time using the cell screening system. The indicator cells contain luminescent reporters consisting of domain markers used to measure the localization of the cytoplasmic and nuclear domains. When the indicator cells are treated with a test compounds, the dynamic redistribution of a PKA fluorescent protein biosensor is recorded intracellularly as a series of images over a time scale ranging from 0.1 s to 10 h. Each image is analyzed by a method that quantifies the movement of the PKA between the cytoplasmic and nuclear domains. To do this calculation, the images of the probes used to mark the cytoplasmic and nuclear domains are used to mask the image of the PKA fluorescent protein biosensor. The integrated brightness per unit area under each mask is used to form a translocation quotient by dividing the cytoplasmic integrated brightness/area by the nuclear integrated brightness/area. By comparing the translocation quotient values from control and experimental wells, the percent translocation is calculated for each potential lead compound. The output of the high-content screen relates quantitative data describing the magnitude of the translocation within a large number of individual cells that have been treated with test compound in the concentration range of $10^{-12}$ M to $10^{-3}$ M.

High-Content Screens Involving the Induction or Inhibition of Gene Expression

RNA-Based Fluorescent Biosensors

Cytoskeletal protein transcription and message localization. Regulation of the general classes of cell physiological responses including cell-substrate adhesion, cell-cell adhesion, signal transduction, cell-cycle events, intermediary and signaling molecule metabolism, cell locomotion, cell-cell communication, and cell death can involve the alteration of gene expression. High-content screens can also be designed to measure this class of physiological response.

In one embodiment, the reporter of intracellular gene expression is an oligonucleotide that can hybridize with the target mRNA and alter its fluorescence signal. In a preferred embodiment, the oligonucleotide is a molecular beacon (Tyagi and Kramer (1996) *Nat. Biotechnol.* 14:303-308), a luminescence-based reagent whose fluorescence signal is dependent on intermolecular and intramolecular interactions. The fluorescent biosensor is constructed by introducing a fluorescence energy transfer pair of fluorescent dyes such that there is one at each end (5' and 3') of the reagent. The dyes can be of any class that contains a protein reactive moiety and fluorochromes whose excitation and emission spectra overlap sufficiently to provide fluorescence energy transfer between the dyes in the resting state, including, but not limited to, fluorescein and rhodamine (Molecular Probes, Inc.). In a preferred embodiment, a portion of the message coding for β-actin (Kislauskis et al. (1994), *J. Cell Biol.* 127:441-451; McCann et al. (1997), *Proc. Natl. Acad. Sci.* 94:5679-5684; Sutoh (1982), *Biochemistry* 21:3654-3661) is inserted into the loop region of a hairpin-shaped oligonucleotide with the ends tethered together due to intramolecular hybridization. At each end of the biosensor a fluorescence donor (fluorescein) and a fluorescence acceptor (rhodamine) are covalently bound. In the tethered state, the fluorescence energy transfer is maximal and therefore indicative of an unhybridized molecule. When hybridized with the mRNA coding for β-actin, the tether is broken and energy transfer is lost. The complete fluorescent biosensor is introduced into the indicator cells using bulk loading methodology.

In one embodiment, living indicator cells are treated with test compounds, at final concentrations ranging from $10^{-12}$ M to $10^{-3}$ M for times ranging from 0.1 s to 10 h. In a preferred embodiment, ratio image data are obtained from living treated indicator cells. To extract morphometric data from each time point, a ratio is made between each pair of images, and each pixel value is then used to calculate the fractional hybridization of the labeled nucleotide. At small fractional values of hybridization little expression of β-actin is indicated. At high fractional values of hybridization, maximal expression of β-actin is indicated. Furthermore, the distribution of hybridized molecules within the cytoplasm of the indicator cells is also a measure of the physiological response of the indicator cells.

Cell Surface Binding of a Ligand

Labeled insulin binding to its cell surface receptor in living cells. Cells whose plasma membrane domain has been labeled with a labeling reagent of a particular color are incubated with a solution containing insulin molecules (Lee et al. (1997), *Biochemistry* 36:2701-2708; Martinez-Zaguilan et al. (1996), *Am. J. Physiol.* 270:C1438-C1446) that are labeled with a luminescent probe of a different color for an appropriate time under the appropriate conditions. After incubation, unbound insulin molecules are washed away, the cells fixed and the distribution and concentration of the insulin on the plasma membrane is measured. To do this, the cell membrane image is used as a mask for the insulin image. The integrated intensity from the masked insulin image is compared to a set of images containing known amounts of labeled insulin. The amount of insulin bound to the cell is determined from the standards and used in conjunction with the total concentration of insulin incubated with the cell to calculate a dissociation constant or insulin to its cell surface receptor.

Labeling of Cellular Compartments

Whole Cell Labeling

Whole cell labeling is accomplished by labeling cellular components such that dynamics of cell shape and motility of the cell can be measured over time by analyzing fluorescence images of cells.

In one embodiment, small reactive fluorescent molecules are introduced into living cells. These membrane-permeant molecules both diffuse through and react with protein components in the plasma membrane. Dye molecules react with intracellular molecules to both increase the fluorescence signal emitted from each molecule and to entrap the fluorescent dye within living cells. These molecules include reactive chloromethyl derivatives of aminocoumarins, hydroxycoumarins, eosin diacetate, fluorescein diacetate, some BODIPY® dye derivatives, and tetramethylrhodamine. The reactivity of these dyes toward macromolecules includes free primary amino groups and free sulfhydryl groups.

In another embodiment, the cell surface is labeled by allowing the cell to interact with fluorescently labeled antibodies or lectins (Sigma Chemical Company, St. Louis, Mo.) that react specifically with molecules on the cell surface. Cell surface protein chimeras expressed by the cell of interest that contain a green fluorescent protein, or mutant thereof, component can also be used to fluorescently label the entire cell surface. Once the entire cell is labeled, images of the entire cell or cell array can become a parameter in high content screens, involving the measurement of cell shape, motility, size, and growth and division.

Plasma Membrane Labeling

In one embodiment, labeling the whole plasma membrane employs some of the same methodology described above for labeling the entire cells. Luminescent molecules that label the entire cell surface act to delineate the plasma membrane.

In a second embodiment subdomains of the plasma membrane, the extracellular surface, the lipid bilayer, and the intracellular surface can be labeled separately and used as components of high content screens. In the first embodiment, the extracellular surface is labeled using a brief treatment with a reactive fluorescent molecule such as the succinimidyl ester or iodoacetamde derivatives of fluorescent dyes such as the fluoresceins, rhodamines, cyanines, and BODIPYS®.

In a third embodiment, the extracellular surface is labeled using fluorescently labeled macromolecules with a high affinity for cell surface molecules. These include fluorescently labeled lectins such as the fluorescein, rhodamine, and cyanine derivatives of lectins derived from jack bean (Con A), red kidney bean (erythroagglutinin PHA-E), or wheat germ.

In a fourth embodiment, fluorescently labeled antibodies with a high affinity for cell surface components are used to label the extracellular region of the plasma membrane. Extracellular regions of cell surface receptors and ion channels are examples of proteins that can be labeled with antibodies.

In a fifth embodiment, the lipid bilayer of the plasma membrane is labeled with fluorescent molecules. These molecules include fluorescent dyes attached to long chain hydrophobic molecules that interact strongly with the hydrophobic region in the center of the plasma membrane lipid bilayer. Examples of these dyes include the PKH series of dyes (U.S. Pat. Nos. 4,783,401, 4,762,701, and 4,859,584; available commercially from Sigma Chemical Company, St. Loius, Mo.), fluorescent phospholipids such as nitrobenzoxadiazole glycerophosphoethanolamine and fluorescein-derivatized dihexadecanoylglycerophosphoetha-nolamine, fluorescent fatty acids such as 5-butyl-4,4-difluoro-4-bora-3a,4a-diazas-indacene-3-nonanoic acid and 1-pyrenedecanoic acid (Molecular Probes, Inc.), fluorescent sterols including cholesteryl 4,4-difluoro-5,7-dimethyl-4-bora-3a,4a-diaza-s-indacene-3-dodecanoate and cholesteryl 1-pyrenehexanoate, and fluorescently labeled proteins that interact specifically with lipid bilayer components such as the fluorescein derivative of annexin V (Caltag Antibody Co, Burlingame, Calif.).

In another embodiment, the intracellular component of the plasma membrane is labeled with fluorescent molecules. Examples of these molecules are the intracellular components of the trimeric G-protein receptor, adenylyl cyclase, and ionic transport proteins. These molecules can be labeled as a result of tight binding to a fluorescently labeled specific antibody or by the incorporation of a fluorescent protein chimera that is comprised of a membrane-associated protein and the green fluorescent protein, and mutants thereof.

Endosome Fluorescence Labeling

In one embodiment, ligands that are transported into cells by receptor-mediated endocytosis are used to trace the dynamics of endosomal organelles. Examples of labeled ligands include BODIPY® FL-labeled low density lipoprotein complexes, tetramethylrhodamine transferrin analogs, and fluorescently labeled epidermal growth factor (Molecular Probes, Inc.)

In a second embodiment, fluorescently labeled primary or secondary antibodies (Sigma Chemical Co. St. Louis, Mo.; Molecular Probes, Inc. Eugene, Oreg.; Caltag Antibody Co.) that specifically label endosomal ligands are used to mark the endosomal compartment in cells.

In a third embodiment, endosomes are fluorescently labeled in cells expressing protein chimeras formed by fusing a green fluorescent protein, or mutants thereof, with a receptor whose internalization labels endosomes. Chimeras of the EGF, transferrin, and low density lipoprotein receptors are examples of these molecules.

Lysosome Labeling

In one embodiment, membrane permeant lysosome-specific luminescent reagents are used to label the lysosomal compartment of living and fixed cells. These reagents include the luminescent molecules neutral red, N-(3-((2,4-dinitrophenyl)amino)propyl)-N-(3-aminopropyl)methylamine, and the LYSOTRACKER® probes which report intralysosomal pH as well as the dynamic distribution of lysosomes (Molecular Probes, Inc.)

In a second embodiment, antibodies against lysosomal antigens (Sigma Chemical Co.; Molecular Probes, Inc.; Caltag Antibody Co.) are used to label lysosomal components that are localized in specific lysosomal domains. Examples of these components are the degradative enzymes involved in cholesterol ester hydrolysis, membrane protein proteases, and nucleases as well as the ATP-driven lysosomal proton pump.

In a third embodiment, protein chimeras consisting of a lysosomal protein genetically fused to an intrinsically luminescent protein such as the green fluorescent protein, or mutants thereof, are used to label the lysosomal domain. Examples of these components are the degradative enzymes involved in cholesterol ester hydrolysis, membrane protein proteases, and nucleases as well as the ATP-driven lysosomal proton pump.

Cytoplasmic Fluorescence Labeling

In one embodiment, cell permeant fluorescent dyes (Molecular Probes, Inc.) with a reactive group are reacted with living cells. Reactive dyes including monobromobimane, 5-chloromethylfluorescein diacetate, carboxy fluorescein diacetate succinimidyl ester, and chloromethyl tetramethylrhodamine are examples of cell permeant fluorescent dyes that are used for long term labeling of the cytoplasm of cells.

In a second embodiment, polar tracer molecules such as Lucifer yellow and cascade blue-based fluorescent dyes (Molecular Probes, Inc.) are introduced into cells using bulk loading methods and are also used for cytoplasmic labeling.

In a third embodiment, antibodies against cytoplasmic components (Sigma Chemical Co.; Molecular Probes, Inc.; Caltag Antibody Co.) are used to fluorescently label the cytoplasm. Examples of cytoplasmic antigens are many of the enzymes involved in intermediary metabolism. Enolase, phosphofructokinase, and acetyl-CoA dehydrogenase are examples of uniformly distributed cytoplasmic antigens.

In a fourth embodiment, protein chimeras consisting of a cytoplasmic protein genetically fused to an intrinsically luminescent protein such as the green fluorescent protein, or mutants thereof, are used to label the cytoplasm. Fluorescent chimeras of uniformly distributed proteins are used to label the entire cytoplasmic domain. Examples of these proteins are many of the proteins involved in intermediary metabolism and include enolase, lactate dehydrogenase, and hexokinase.

In a fifth embodiment, antibodies against cytoplasmic antigens (Sigma Chemical Co.; Molecular Probes, Inc.; Caltag Antibody Co.) are used to label cytoplasmic components that are localized in specific cytoplasmic sub-domains. Examples of these components are the cytoskeletal proteins actin, tubulin, and cytokeratin. A population of these proteins within cells is assembled into discrete structures, which in this case, are fibrous. Fluorescence labeling of these proteins with antibody-based reagents therefore labels a specific sub-domain of the cytoplasm.

In a sixth embodiment, non-antibody-based fluorescently labeled molecules that interact strongly with cytoplasmic proteins are used to label specific cytoplasmic components. One example is a fluorescent analog of the enzyme DNAse I (Molecular Probes, Inc.) Fluorescent analogs of this enzyme bind tightly and specifically to cytoplasmic actin, thus labeling a sub-domain of the cytoplasm. In another example, fluorescent analogs of the mushroom toxin phalloidin or the drug paclitaxel (Molecular Probes, Inc.) are used to label components of the actin- and microtubule-cytoskeletons, respectively.

In a seventh embodiment, protein chimeras consisting of a cytoplasmic protein genetically fused to an intrinsically luminescent protein such as the green fluorescent protein, or mutants thereof, are used to label specific domains of the cytoplasm. Fluorescent chimeras of highly localized proteins are used to label cytoplasmic sub-domains. Examples of these proteins are many of the proteins involved in regulating the cytoskeleton. They include the structural proteins actin, tubulin, and cytokeratin as well as the regulatory proteins microtubule associated protein 4 and $\alpha$-actinin.

Nuclear Labeling

In one embodiment, membrane permeant nucleic-acid-specific luminescent reagents (Molecular Probes, Inc.) are used to label the nucleus of living and fixed cells. These reagents include cyanine-based dyes (e.g., TOTO®, YOYO®, and BOBO™), phenanthidines and acridines (e.g., ethidium bromide, propidium iodide, and acridine orange), indoles and imidazoles (e.g., Hoechst 33258, Hoechst 33342, and 4',6-diamidino-2-phenylindole), and other similar reagents (e.g., 7-aminoactinomycin D, hydroxystilbamidine, and the psoralens).

In a second embodiment, antibodies against nuclear antigens (Sigma Chemical Co.; Molecular Probes, Inc.; Caltag Antibody Co.) are used to label nuclear components that are localized in specific nuclear domains. Examples of these components are the macromolecules involved in maintaining DNA structure and function. DNA, RNA, histones, DNA polymerase, RNA polymerase, lamins, and nuclear variants of cytoplasmic proteins such as actin are examples of nuclear antigens.

In a third embodiment, protein chimeras consisting of a nuclear protein genetically fused to an intrinsically luminescent protein such as the green fluorescent protein, or mutants thereof, are used to label the nuclear domain. Examples of these proteins are many of the proteins involved in maintaining DNA structure and function. Histones, DNA polymerase, RNA polymerase, lamins, and nuclear variants of cytoplasmic proteins such as actin are examples of nuclear proteins.

Mitochondrial Labeling

In one embodiment, membrane permeant mitochondrial-specific luminescent reagents (Molecular Probes, Inc.) are used to label the mitochondria of living and fixed cells. These reagents include rhodamine 123, tetramethyl rosamine, JC-1, and the MITOTRACKER® reactive dyes.

In a second embodiment, antibodies against mitochondrial antigens (Sigma Chemical Co.; Molecular Probes, Inc.; Caltag Antibody Co.) are used to label mitochondrial components that are localized in specific mitochondrial domains. Examples of these components are the macromolecules involved in maintaining mitochondrial DNA structure and function. DNA, RNA, histones, DNA polymerase, RNA polymerase, and mitochondrial variants of cytoplasmic macromolecules such as mitochondrial tRNA and rRNA are examples mitochondrial antigens. Other examples of mitochondrial antigens are the components of the oxidative phosphorylation system found in the mitochondria (e.g., cytochrome c, cytochrome c oxidase, and succinate dehydrogenase).

In a third embodiment, protein chimeras consisting of a mitochondrial protein genetically fused to an intrinsically luminescent protein such as the green fluorescent protein, or mutants thereof, are used to label the mitochondrial domain. Examples of these components are the macromolecules involved in maintaining mitochondrial DNA structure and function. Examples include histones, DNA polymerase, RNA polymerase, and the components of the oxidative phosphorylation system found in the mitochondria (e.g., cytochrome c, cytochrome c oxidase, and succinate dehydrogenase).

Endoplasmic Reticulum Labeling

In one embodiment, membrane permeant endoplasmic reticulum-specific luminescent reagents (Molecular Probes, Inc.) are used to label the endoplasmic reticulum of living and fixed cells. These reagents include short chain carbocyanine dyes (e.g., $DiOC_6$ and $DiOC_3$), long chain carbocyanine dyes (e.g. $DiIC_{16}$ and $DiIC_{18}$), and luminescently labeled lectins such as concanavalin A.

In a second embodiment, antibodies against endoplasmic reticulum antigens (Sigma Chemical Co.; Molecular Probes, Inc.; Caltag Antibody Co.) are used to label endoplasmic reticulum components that are localized in specific endoplasmic reticulum domains. Examples of these components are the macromolecules involved in the fatty acid elongation systems, glucose-6-phosphatase, and HMG CoA-reductase.

In a third embodiment, protein chimeras consisting of a endoplasmic reticulum protein genetically fused to an intrinsically luminescent protein such as the green fluorescent protein, or mutants thereof, are used to label the endoplasmic reticulum domain. Examples of these components are the macromolecules involved in the fatty acid elongation systems, glucose-6-phosphatase, and HMG CoA-reductase.

Golgi Labeling

In one embodiment, membrane permeant Golgi-specific luminescent reagents (Molecular Probes, Inc.) are used to label the Golgi of living and fixed cells. These reagents include luminescently labeled macromolecules such as wheat germ agglutinin and Brefeldin A as well as luminescently labeled ceramide.

In a second embodiment, antibodies against Golgi antigens (Sigma Chemical Co.; Molecular Probes, Inc.; Caltag Antibody Co.) are used to label Golgi components that are localized in specific Golgi domains. Examples of these components are N-acetylglucosamine phosphotransferase, Golgi-specific phosphodiesterase, and mannose-6-phosphate receptor protein.

In a third embodiment, protein chimeras consisting of a Golgi protein genetically fused to an intrinsically luminescent protein such as the green fluorescent protein, or mutants thereof, are used to label the Golgi domain. Examples of these components are N-acetylglucosamine phosphotransferase, Golgi-specific phosphodiesterase, and mannose-6-phosphate receptor protein.

While many of the examples presented involve the measurement of single cellular processes, this is again is intended for purposes of illustration only. Multiple parameter high-content screens can be produced by combining several single parameter screens into a multiparameter high-content screen or by adding cellular parameters to any existing high-content screen. Furthermore, while each example is described as being based on either live or fixed cells, each high-content screen can be designed to be used with both live and fixed cells.

Those skilled in the art will recognize a wide variety of distinct screens that can be developed based on the disclosure provided herein. There is a large and growing list of known biochemical and molecular processes in cells that involve translocations or reorganizations of specific components within cells. The signaling pathway from the cell surface to target sites within the cell involves the translocation of plasma membrane-associated proteins to the cytoplasm. For example, it is known that one of the src family of protein tyrosine kinases, pp60c-src (Walker et al (1993), *J. Biol. Chem.* 268:19552-19558) translocates from the plasma membrane to the cytoplasm upon stimulation of fibroblasts with platelet-derived growth factor (PDGF). Additionally, the targets for screening can themselves be converted into fluorescence-based reagents that report molecular changes including ligand-binding and post-translocational modifications.

We claim:

1. An automated method for analyzing neurite outgrowth comprising;
    (a) providing an array of locations comprising cells, wherein the cells possess at least a first luminescently labeled reporter molecule that reports on cell location, and at least a second luminescently labeled reporter molecule that reports on neurite outgrowth, and wherein the cells comprise neurons;
    (b) obtaining a nuclear image from the at least first luminescently labeled reporter molecule and a neurite image from the at least second luminescently labeled reporter molecule;
    (c) automatically identifying cell bodies from the nuclear image;
    (d) automatically identifying neurites extending from the cell bodies by identifying pixels in the neurite image that are not present in the nuclear image, wherein said pixels define neurites extending from the cell bodies; and
    (e) automatically determining one or more features of the defined neurites.

2. The method of claim 1 further comprising contacting the neurons with a test compound and determining an effect of the test compound on neurite outgrowth.

3. The method of claim 2, further comprising contacting the neurons with a neurotoxin either before, after, or simultaneously with the test compound.

4. The method of claim 1 wherein the first luminescently labeled reporter molecule comprises a DNA binding compound.

5. The method of claim 1 wherein the second luminescently labeled reporter molecule comprises a compound that selectively detects a cell component selected from the group consisting of cytoplasm, membrane, neuron-specific cell component, and cellular proteins.

6. The method of claim 2, further comprising contacting the cells with a control compound known to stimulate neurite outgrowth, and determining an effect of the control compound on test compound-induced neurite outgrowth.

7. The method of claim 1 wherein the one or more features of the defined neurites comprise conditions that are toxic to neurons and affect neurite morphology.

8. The method of claim 1 wherein the second luminescently labeled reporter molecule is neuron-specific.

9. The method of claim 1 wherein the array of locations containing cells include cells other than neurons, and wherein the neurons possess a neuron-specific luminescent reporter molecule, and wherein the neuron-specific luminescent reporter molecule is spectrally distinguishable from the first and second luminescently labeled reporter molecule.

10. The method of claim 1 wherein identifying cell bodies comprises the steps of:
    a. generating a kernel image from the nuclear image;
    b. performing conditional dilations of the kernel image to identify cell bodies.

11. The method of claim 10, wherein identifying neurites extending from cell bodies comprises the steps of:
   a. generating a reservoir image from the neurite image; and
   b. identifying positive pixels in the reservoir image that are not present in the cell bodies, wherein such positive pixels belong to neurites extending from cell bodies.

12. The method of claim 11, further comprising
   a. performing one conditional dilation of the kernel image to acquire a dilation image;
   b. determining a set of nodes from the dilation image;
   c. linking together connected nodes; and
   d. repeating steps (a)-(c) until an entire neurite length has been traced.

13. The method of claim 1, wherein sub-regions of the array of locations containing cells are sampled multiple times at intervals to provide kinetic measurement of changes in the distribution, environment or activity of the luminescent reporter molecules on or within the cells.

14. A computer readable storage medium comprising a program containing a set of instructions for causing a cell screening system to execute a method for analyzing neurite outgrowth, wherein the instructions comprise instructions causing the cell screening system to carry out procedures comprising
   (a) imaging or scanning multiple cells in a plurality of locations on an array of locations comprising cells, wherein the cells possess at least a first luminescently labeled reporter molecule that reports on cell location, and at least a second luminescently labeled reporter molecule that reports on neurite outgrowth, and wherein the cells comprise neurons;
   (b) obtaining a nuclear image from the at least first luminescently labeled reporter molecule and a neurite image from the at least second luminescently labeled reporter molecule;
   (c) automatically identifying cell bodies from the nuclear image;
   (d) automatically identifying neurites extending from the cell bodies by identifying pixels in the neurite image that are not present in the nuclear image, wherein said pixels define neurites extending from the cell bodies; and
   (e) automatically determining one or more features of the defined neurites.

15. The method of claim 1, wherein the one or more features of the defined neurites comprise one or more of the following:
   a) Number of cells;
   b) Number of neurons;
   c) Total neurite length from all cells;
   d) Total number of neurite branches from all cells;
   e) Number of neurites per cell;
   f) Number of neurites per positive neuron
   g) Neurite length from each cell;
   h) Neurite length per positive neuron
   i) Neurite length per neurite
   j) Number of cells that are positive for neurite outgrowth
   k) Percentage of cells positive for neurite outgrowth;
   l) cell body area;
   m) number of branches per neuron;
   n) number of branches per neurite; or
   o) Degree of neurite outgrowth from a neuron or neuronal cell cluster.

16. The computer readable storage medium of claim 14, wherein the instructions further comprise instructions causing the cell screening system to determine one or more features of the defined neurites selected from the group consisting of:
   a) Number of cells;
   b) Number of neurons;
   c) Total neurite length from all cells;
   d) Total number of neurite branches from all cells;
   e) Number of neurites per cell;
   f) Number of neurites per positive neuron
   g) Neurite length from each cell;
   h) Neurite length per positive neuron
   i) Neurite length per neurite
   j) Number of cells that are positive for neurite outgrowth
   k) Percentage of cells positive for neurite outgrowth;
   l) cell body area;
   m) number of branches per neuron;
   n) number of branches per neurite; or
   o) Degree of neurite outgrowth from a neuron or neuronal cell cluster.

* * * * *